(12) United States Patent
Gizewski

(10) Patent No.: US 7,953,613 B2
(45) Date of Patent: May 31, 2011

(54) HEALTH MAINTENANCE SYSTEM

(76) Inventor: Theodore M. Gizewski, Santa Barbara, CA (US)

( * ) Notice: Subject to any disclaimer, the term of this patent is extended or adjusted under 35 U.S.C. 154(b) by 1125 days.

(21) Appl. No.: 11/649,922

(22) Filed: Jan. 3, 2007

(65) Prior Publication Data

US 2008/0162352 A1 Jul. 3, 2008

(51) Int. Cl.
*G06Q 10/2006* (2006.01)
(52) U.S. Cl. .................... 705/3; 705/2
(58) Field of Classification Search ............ 705/2, 3; 600/300, 439, 485
See application file for complete search history.

(56) References Cited

U.S. PATENT DOCUMENTS

| | | | | |
|---|---|---|---|---|
| 5,534,851 | A * | 7/1996 | Russek | 340/573.4 |
| 5,710,551 | A * | 1/1998 | Ridgeway | 340/870.09 |
| 6,665,565 | B1 * | 12/2003 | Stomberg et al. | 607/31 |
| 6,955,647 | B2 * | 10/2005 | Rice | 600/300 |
| 7,286,997 | B2 * | 10/2007 | Spector et al. | 705/2 |
| 2004/0073453 | A1 * | 4/2004 | Nenov et al. | 705/2 |
| 2005/0144042 | A1 * | 6/2005 | Joffe et al. | 705/2 |
| 2005/0283380 | A1 * | 12/2005 | Garduno | 705/2 |
| 2006/0168043 | A1 * | 7/2006 | Eisenberger et al. | 709/206 |
| 2006/0200029 | A1 * | 9/2006 | Evans et al. | 600/485 |
| 2007/0243233 | A1 * | 10/2007 | Cherukuri et al. | 424/439 |
| 2008/0040151 | A1 * | 2/2008 | Moore | 705/2 |

* cited by examiner

*Primary Examiner* — Gerald J. O'Connor
*Assistant Examiner* — Teresa Woods
(74) *Attorney, Agent, or Firm* — Guy L. Cumberbatch

(57) ABSTRACT

Disclosed is a health maintenance system for comprehensive health assessment, abnormality detection, health monitoring, health pattern and trend detection, health strategy development, and health history archiving. The health maintenance system comprises a subscriber segment and a system segment, communicatively coupled. The subscriber segment acquires subscriber personal and health data from at least one subscriber, analyzing the data; identifies specific health abnormalities; prescribes at least one customized subscriber health product, instructs the subscriber on the implementation of the prescribed health product, compiles and preserves the subscriber's health history data—including abnormalities and prescribed health products, and performs monitoring of subscriber health conditions. The subscriber segment acquires subscriber data from the subscriber segment, stores and maintains the data, facilitates retrieval of data by the subscriber and emergency medical personnel analyzes subscriber patterns and trends, develops new health products and modifies existing health products, and monitors the effectiveness of health products.

78 Claims, 18 Drawing Sheets

HEALTH MAINTENANCE SYSTEM

FIELD OF THE INVENTION

The present invention relates generally to personalized health and longevity augmentation systems, and more particularly, to health maintenance systems and methods thereof based on computerized data acquisition and analysis.

BACKGROUND OF THE INVENTION

Maintaining health is a very important aspect of human life. Public awareness of health has increased but due to escalating medical costs, time restraints on physician and medical specialization, medicine has become more production oriented, impersonal and compartmentalized. Much of the administration of health services has remained qualitative and depends heavily on the knowledge and competence of a physician. However, in today's world, the availability of sophisticated technologies and compounding scientific advancements has raised the public's expectations of what the standard of health care should be. It has become unrealistic and impractical to project these expectations solely onto the current model of practicing medicine. Individuals need a means by which they can become more active and effective in the management of their health. Among other things, individuals need to be able to assess their health and understand what is normal and what is abnormal, relative to their own unique characteristics which include age, gender, physical characteristics, race, ethnicity, geographical region and so on. Also, individuals need simple and quick access to personalized health strategies that address behavioral modifications, environment optimization, nutritional optimization, physical fitness, early detection of abnormalities and disease prevention tactics that are tailored to each individual's unique characteristics and situation. As importantly, there is the need to quantitatively evaluate and diagnose a condition and gage the progression of a condition and the effectiveness of a health strategy or medical treatment.

The general public and particularly workers in certain occupations are subjected to an array of illnesses, diseases and exotic health risks which, among other things can include exposure to dangerous microbes and toxic/noxious nuclear, biological and chemical substances. The effects of these exposures can be debilitating and even lethal. There is no easily accessible, broad network of health monitoring systems available that can be sensitized to detect individual symptoms of an exposure and rapidly establish exposure type and severity or assess particular patterns and trends in order to determine the impact across small or large population group and geographical area. People need an easy to use health monitoring system that can conveniently monitor their health and alert them of possible exposures to a toxic and noxious substance. Once an exposure is detected, the system needs to advise them of appropriate intervention, decontamination and treatment options and notify the appropriate health authorities of the scale, location and extent of the exposure or exposures. With such a system, exposures could be detected early, often before other evidence of contamination is available and before the contamination can spread.

A significant portion of the population is classified as chronically ill. Many of those individuals go undiagnosed, misdiagnosed and ineffectively treated for years. They frequently suffer debilitating symptoms that affect their ability to work or even care for themselves. In many cases, these individuals exhibit a complex array of physical, physiological and behavioral abnormalities that can offer clues or pointers as to the core cause or causes of their condition. However, these individuals typically do not have access to effective and intelligent monitoring systems and have few choices but to suffer in silence. There is a clear need for a comprehensive and integrated system that could conveniently interact with the subject in order to detect, track, document and assess certain key environmental, behavioral, physical and physiological characteristics and peculiarities in order to establish meaningful correlations and to develop patterns and trends that can point to a core cause or causes of the condition.

The population is growing older, generally more prosperous and more self directed, particularly in the area of health. As they age, they are displaying an unusually strong desire to extend their youthful appearance and vitality beyond those of many previous generations. Currently there are no comprehensive and integrated systems or technologies available that would permit these individuals to pursue credible health and longevity augmentation strategies. To be effective, these strategies must take into consideration the individual's unique living environments, behaviors, physical characteristics and physiological characteristics in conjunction with credible scientific methodologies. Nor are there any comprehensive health assessment systems available that would gauge an individual's health and aging process, relative to specific population groups. Also there is a need for a system that can conveniently monitor the effectiveness of a strategy, treatment or regime in order to apply the safest and most effective approach.

The development, compilation and storage of health histories are a problem. In many cases these health histories are developed manually and are dispersed among numerous health care providers. The documents themselves are often difficult to understand, due to the volume of information, legibility issues, writing styles, obsolete data and fragmented information. In emergency situations, physicians are often left with little medical history and are forced to make important treatment decisions based on limited data There is a need for a centralized health history archive that permanently maintains health and medical data that is regularly updated by the individual and each of their various health care providers. This data could then be made available to a physician at any time; any place through the use of a communications network such as the internet. Also, the health of an individual is often the result of certain key genetic predispositions. In today's world, there is very little personal health history information permanently preserved and readily available for retrieval. Having such information would help each new generation better understand their genetic predispositions and pursue those health strategies that are most likely to benefit them.

In the past, attempts have been made to address certain specific issues in the areas relating to health condition monitoring, abnormality detection, data analysis, health strategy development, documenting health histories, and various other similar health subjects. Along with human intervention, various computerized methodologies have been used. However, these computerized methodologies have been used in isolation and do not represent a comprehensive health maintenance system with highly integrated components, widely dispersed across a broad network.

U.S. Pat. No. 6,692,436 disclose a health care information system having a health kiosk providing blood pressure testing, a health and fitness evaluation, and a medication encyclopedia. The health kiosk typically interfaces to a computer or server, such as a pharmacy computer or a remote server which compares pharmaceuticals selected by a user to information in the medication encyclopedia to determine compatibility for prescription medications and over-the-counter medications. In some systems, the kiosk also supplies one item or more of an extended health information, a weight scale constructed into the seat of the kiosk, a directory of health care service and product providers, an a directory of community health, support, and service groups.

U.S. Pat. No. 7,024,369 provides for a personal health monitoring system for balancing the comprehensive health of a user, wherein a current health profile for a user is monitored at a personal health monitoring system. The current health profile includes multiple monitored physical parameters and multiple monitored environmental parameters. Multiple actions for selection by the user are received at the personal health monitoring system. The multiple actions are prioritized according to the current health profile and designated allowances for the user at the personal health monitoring system, such that the personal health monitoring system aids the user in selecting from among the multiple actions in order to balance the comprehensive health of the user. Multiple tasks for scheduling in a user's electronic schedule are scheduled according to the current health profile and designated allowances for the user at the personal health monitoring system.

The available solutions for a health information collection and retrieval system still requires a lot of human intervention and lacks the integration and the computerized, user-friendly interface approach. The available systems fall short of providing a single, comprehensive, highly integrated health maintenance system that is capable of collecting a broad array of personal history and health data, developing and maintaining individualized health baseline profiles, identifying and tracking patterns and trends, detecting abnormalities and peculiarities, cross-correlating particular health characteristics to reference material and authoritative standards, conducting comparative analysis in order to establish a relative condition (i.e. conditions relative to those of a population norm), developing personalized health strategies, monitoring specific health conditions, monitoring drug interactions and reaction, monitoring the effectiveness of a treatment or prescribed strategy, developing and maintaining health archives, and offering a host of personalized health products through an integrated marketplace.

Accordingly, what is needed is a comprehensive, highly automated and integrated health maintenance system which is capable of offering a broad array of personalized health services and products. These include convenient access, a user-friendly interface, personal and family health history data collection, individualized health profiles, comparative assessments of health conditions (i.e. an individual's health condition relative to that of a similar population group) health patterns and trends tracking, abnormality detection, health data analysis and health assessments, personalized health strategies, health condition monitoring, drug reaction and interaction monitoring, treatment effectiveness monitoring, health history archiving and an array of personalized commercial health products.

SUMMARY OF THE INVENTION

In view of the foregoing disadvantages, inherent in the prior arts, the general purpose of the present invention is to provide a health maintenance system configured to include unique features plus the advantages of the prior arts, while overcoming the drawbacks of the prior arts.

In one aspect, the present invention provides a health maintenance system, comprising a subscriber segment and a system segment communicatively coupled to the subscriber segment. The subscriber segment is capable of acquiring subscriber data from at least one subscriber; analyzing the subscriber data; identifying specific abnormalities; developing and customizing at least one health product for the subscriber; communicating customized health product to the subscriber, compiling and preserving the acquired subscriber data along with the identified abnormalities, and customized health product; and monitoring health condition of the subscriber. The system segment is capable of acquiring subscriber data from the subscriber segment; storing and maintaining the acquired subscriber data; facilitating retrieval of the subscriber data; analyzing subscriber patterns and trends; developing new health products and modifying existing health products; and monitoring efficiency of the health products.

In another aspect, the present invention provides a health maintenance system, comprising: a plurality of personal data acquisition units, a plurality of central data processing units, a plurality of data maintenance and archiving units, and a data maintenance and archiving unit-command center. Each personal data acquisition unit is capable of interacting with at least one subscriber and acquiring subscriber data from the subscriber. Each central data processing unit is communicatively coupled to the personal data acquisition units within its designated region. The central data processing units are capable of: remotely managing interactions between the subscriber and the personal data acquisition units; systematically collecting subscriber data from the personal data acquisition units; organizing, categorizing and analyzing the subscriber data; identifying specific abnormalities; developing and customizing at least one of a health product, service, program, and/or health regime; compiling subscriber data in the form of a health history archive; and monitoring health condition of the subscriber. Each data maintenance and archiving unit is communicatively coupled to the central data processing units, within its designated region, and is capable of monitoring performance and operational availability of the central data processing units. The data maintenance and archiving unit-command center is communicatively coupled to the data maintenance and archiving units. The data maintenance and archiving unit-command center is capable of monitoring the performance and operational availability of the data maintenance and archiving units. The data maintenance and archiving units, in combination with data maintenance and archiving unit-command center, are capable of: collecting cumulative subscriber data; analyzing subscriber patterns and trends; developing at least one new health product, program, service, and/or health regime; modifying and enhancing existing health products, programs, services, and/or health regimes; and monitoring effectiveness and efficiency of the health products, programs, services, and health regimes.

In another aspect, the present invention provides a health maintenance system, comprising a plurality of personal data acquisition units, a plurality of central data processing units, and a data maintenance and archiving unit-command center. Each personal data acquisition unit is capable of acquiring subscriber data from at least one subscriber. Each central data processing unit is communicatively coupled to the personal data acquisition units within its designated region. The central data processing units are capable of collecting subscriber data from the personal data acquisition units; analyzing the subscriber data; developing and customizing at least one health product, program, service, and/or regimen for the subscriber; and monitoring health condition of the subscriber. The data maintenance and archiving unit-command center is communicatively coupled to the central data processing units. The data maintenance and archiving unit-command center is capable of monitoring performance and the operational availability of the central data processing units. The data maintenance and archiving unit-command center is capable of collecting cumulative subscriber data, analyzing subscriber patterns and trends, developing new health products and modifying existing health products, and monitoring efficiency of the health products.

These, together with other aspects of the present invention, along with the various features of novelty that characterize the invention, are pointed out with particularity in the claims annexed hereto and forming a part of this disclosure. For a better understanding of the invention, its operating advantages and the specific objects attained by its uses, reference should be made to the accompanying drawings and descriptive matter in which there are illustrated exemplary embodiments of the present invention.

BRIEF DESCRIPTION OF THE DRAWINGS

The advantages and features of the present invention will become better understood with reference to the following more detailed description and claims taken in conjunction with the accompanying drawings, wherein like elements are identified with like symbols, and in which:

Like reference numerals refer to like parts throughout the description of several views of the drawings.

DETAILED DESCRIPTION OF THE INVENTION

The exemplary embodiments described herein detail for illustrative purposes are subject to many variations in structure and design. It should be emphasized, however that the present invention is not limited to a particular health maintenance system configuration, as shown and described It is understood that various omissions, substitutions of equivalents are contemplated as circumstances may suggest or render expedient, but is intended to cover the application or implementation without departing from the spirit or scope of the claims of the present invention.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item.

Figure 1:
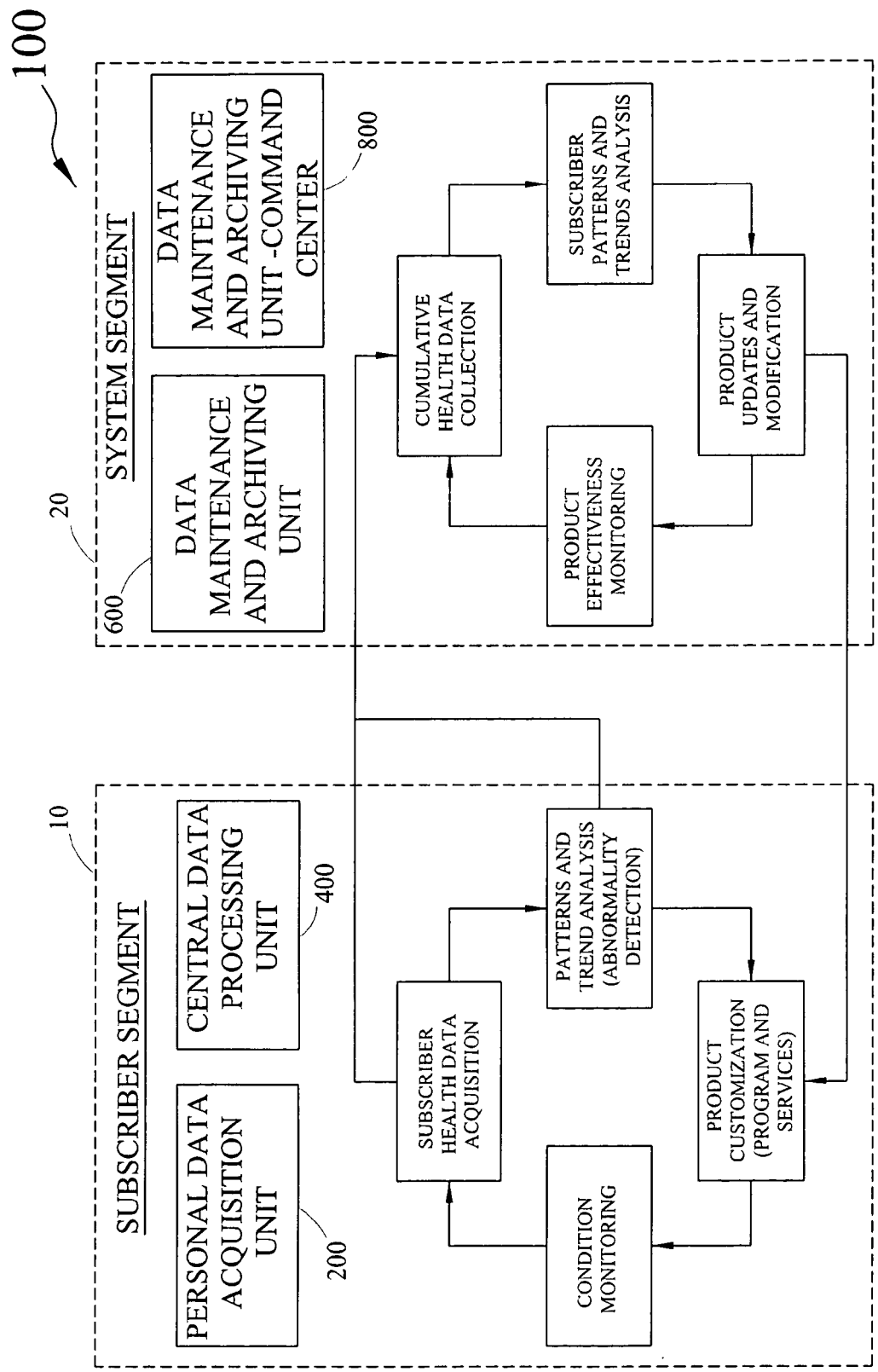
FIG. 1 illustrates a "double closed loop" structure of a health maintenance system 100 comprising a subscriber-segment 10 and a system-segment 20, according to an exemplary embodiment of the present invention.
Figure 2:
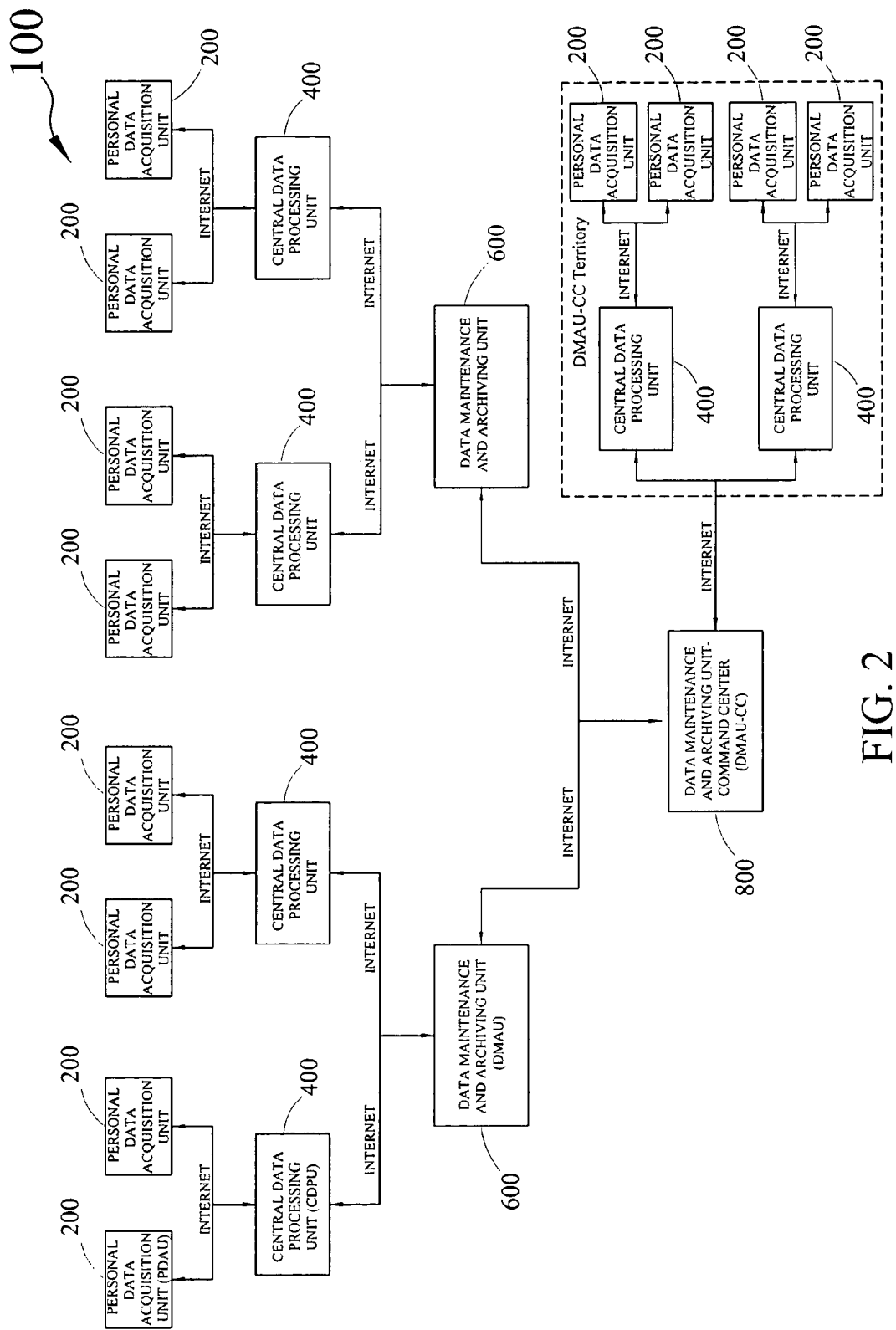
FIG. 2 is a block diagram of the health maintenance system 100, according to an exemplary embodiment of the present invention.

Referring to FIG. 1, the present invention provides a health maintenance system 100 forming a unique "double closed loop" which partitions the system into two functional segments: a subscriber-segment 10; and a system-segment 20. The health maintenance system 100 has an automated, secure and user friendly interface for communicating with one or more subscriber. In one embodiment, as shown in FIG. 2, the health maintenance system 100 comprises four sub-components: personal data acquisition unit (PDAU) 200; central data processing unit (CDPU) 400; data maintenance and archiving unit (DMAU) 600; and data maintenance and archiving unit-command center (DMAU-CC) 800. The subscriber-segment 10 requires the collaboration of the PDAU 200 and CDPU 400 to perform the following functions: data acquisition (i.e. acquiring subscriber data from at least one subscriber); data analysis (i.e. analyzing the subscriber characteristics, lifestyle, condition, and the like); identifying specific abnormalities; identifying and prescribing health products, programs, services and/or regimens development and customization (i.e., developing and customizing at least one health product for the subscribers); communicating the customized health product to the subscriber; compiling and preserving the acquired subscriber data; and condition monitoring (i.e., monitoring health condition of the subscriber, monitoring the effectiveness of a treatment, monitoring the progression of a condition, and the like). The system segment requires the collaboration of DMAU 600 and DMAU-CC 800 to perform the following functions: acquiring subscriber data from the subscriber segment; storing and maintaining the acquired subscriber data while facilitating retrieval by the subscriber; analyzing subscriber patterns and trends; developing new health products and modifying existing health products; and monitoring performance of the health products and changes in a population group. As used herein, a 'subscriber' refers to a user subscribing to the health maintenance system 100. Also, as used herein, 'subscriber data' refers to all data provided by the subscriber that may be useful in description and health analysis of the subscriber; 'cumulative subscriber data' refers to subscriber data of a plurality of subscribers accumulated over a period of time.

The four sub-components, i.e., the PDAU 200, the CDPU 400, the DMAU 600, and DMAU-CC 800 are communicatively coupled to each other through a communication network, for example, the Internet as shown in FIG. 2. Alternatively, the communication network may be a public switched telephone network (PSTN), global system for mobile communications (GSM) network, general packet radio service (GPRS) network, and the like.

Referring again to FIG. 2, the health maintenance system 100 comprises a plurality of CDPUs 400 distributed throughout a geographical territory. Each CDPU 400 supports a prescribed network of PDAUs 200 within a designated region of the CDPU 400. Under the direction of the CDPU 400, the PDAUs 200 interact with subscribers to facilitate the acquisition of health related information. More specifically, the CDPU 400 remotely manages interactions between the subscriber and the personal data acquisition units in order to: systematically collect subscriber data through the personal data acquisition units; organizing, categorizing and analyzing the subscriber data; identifying specific abnormalities; developing and customizing at least one health product, service, program or health regime for the subscriber; compiling subscriber data in the form of a health history archive; managing interactions between the subscriber and the personal data acquisition units; and monitoring the health condition of the subscriber, monitoring the effectiveness of a treatment or program, and monitoring the progression of a condition The CDPUs 400 are centrally located within their geographical territories and function as data processing and analysis hubs for their respective network of PDAUs 200. The health maintenance system 100 comprises a plurality of DMAUs 600, each DMAU 600 responsible for monitoring the operational effectiveness, performance and operational availability of the CDPUs 400 located within its designated region, of the DMAU 600, while ensuring the collaboration between the CDPUs 400 in the region. For example, a DMAU 600 in North America for monitoring the operation of CDPUs 400 in North America; another DMAU 600 in Europe for monitoring the operation of CDPUs 400 in Europe; another DMAU 600 Asia for monitoring the operation of CDPUs 400 in Asia, and the like. Also, the DMAUs 600 are capable of collecting and forwarding health history archive data and operational performance and effectiveness data to the DMAU-CC 800. In turn, the DMAU-CC 800 oversees the performance, effectiveness and operational availability of the entire network of DMAUs 600, worldwide. Also, the DMAU-CC 800 compiles and maintains the subscriber's master health history archives, controls and updates reference materials, and evaluates population patterns and trends to determine the effectiveness and adequacy, of the health maintenance system 100, and to make continuous improvements. Alternatively, or in addition, as shown in FIG. 2, the DMAU-CC 800 may function as a DMAU 600, monitoring the operational effectiveness, performance and operational availability of the CDPUs 400 within a geological proximity.

The PDAUs 200 have three major functions: supporting the interface between the subscriber and the CDPU 400; supporting data acquisition activities; and managing data security and data communication. The PDAUs 200 may be widely distributed to sponsoring entities such as clinics, employers, insurers, government organizations, institutions, and individuals with an interest in health condition monitoring, health abnormality detection, and personalized health services; and generally a hundred or more different individuals may register as subscribers per PDAU 200. In one embodiment, the PDAU 200 can be in the form of a stand-alone, full-service, computerized health station, referred to as personal data acquisition unit-health station (PDAU-HS) 200*a* (See FIG. 3). The PDAU-HS 200*a* may be compact in design, easy to use, and comes with a pre-packaged suite of hardware accessories and software that facilitates subscriber interface and accommodates the acquisition of subscriber data (for example, psychological data, physical data, physiological data, behaviors and the like). The PDAU-HS 200*a* incorporates sophisticated graphical-user-interface technologies and enhanced audio and voice recognition capabilities in order to facilitate communications, advanced data security features, and extensive data management and distribution capabilities. Also, the PDAU-HS 200*a* may have a set of test and measurement equipment, supported with enhanced graphical and audio interactive abilities.

Figure 3:
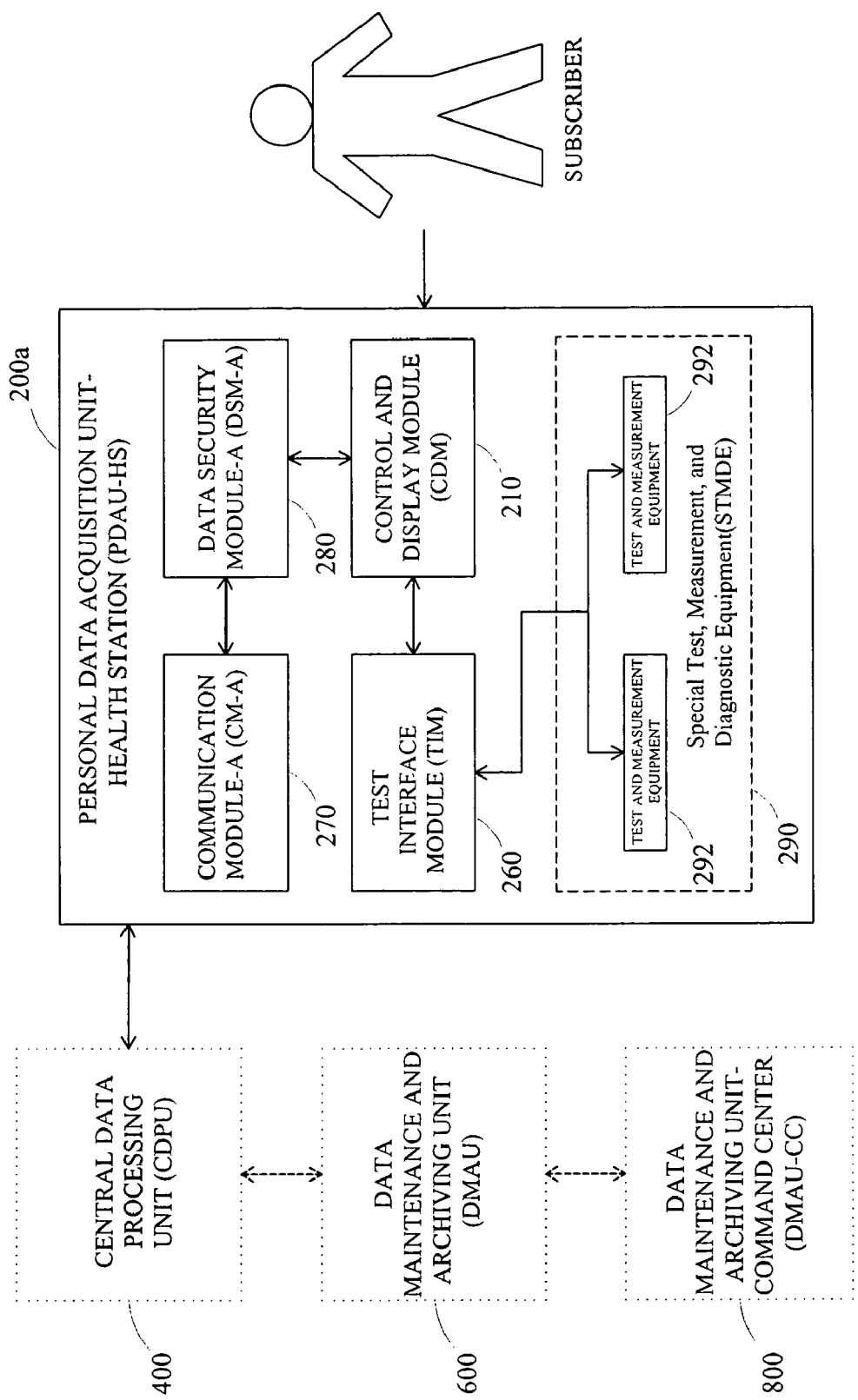
FIG. 3 is a block diagram of a personal data acquisition unit-health station 200a, according to an exemplary embodiment of the present invention.

Referring to FIG. 3, the PDAU-HS 200*a* comprises: a control and display module (CDM) 210; a first data security module coupled to the CDM 210, the first data security module referred herein as data security module-A (DSM-A) 280; a first communication module coupled to the DSM-A 280 the first communication module referred herein as communication module-A (CM-A) 270; a test interface module (TIM) 260, coupled to the CDM 210; and a plurality of test and measurement equipment 292 which is collectively referred to as scaleable components or suites of special test, measurement, and diagnostic equipment (STMDE) 290. The STMDE 290 is coupled to the TIM 260 and is capable of collecting test and measurement data from the subscribers.

Figure 4:
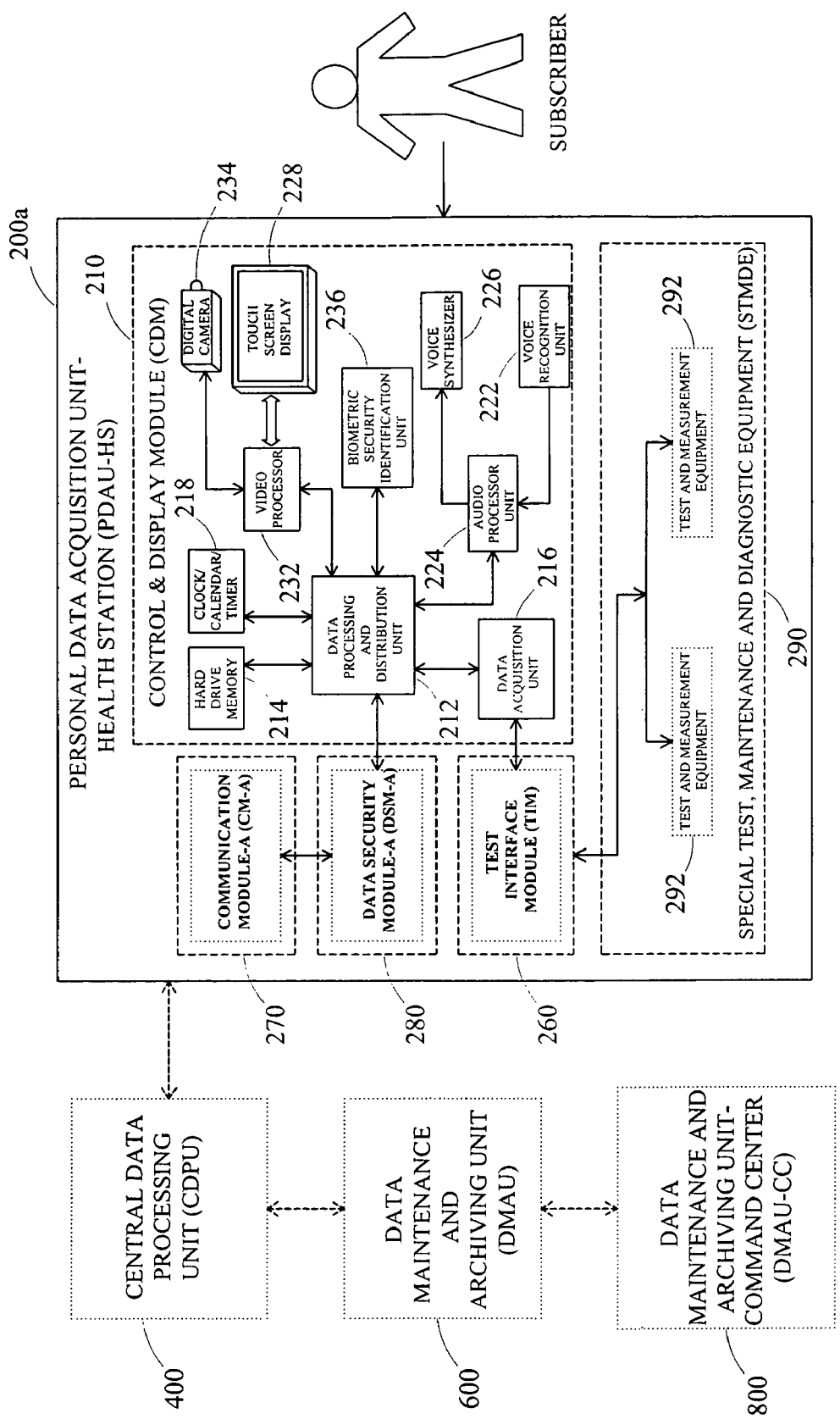
FIG. 4 is a block diagram illustrating components of a control and display module 210 of the personal data acquisition unit-health station 200a, according to an exemplary embodiment of the present invention.

The CDM 210 incorporates the software and hardware components needed to directly interact with the subscriber. As shown in FIG. 4, the CDM 210 is comprised of a data processing and data distribution unit 212 (also referred to as data processor 212); a hard drive memory 214 or memory storage device coupled to the data processing and data distribution unit 212; a data acquisition unit 216 coupled to the data processing and data distribution unit 212; a clock/calendar/timer unit 218 coupled to the data processing and data distribution unit 212; and a plurality of user interface features (software programs and hardware interfaces) for secure and effective interaction with the subscriber, the user interface features coupled to the data processing and data distribution unit 212. Preferably, the memory 214 may be any type of dynamic storage device, sufficient to hold the necessary programmable instructions and data structures for functioning of the CDM 210. The data processor 212 may be capable of executing programmable instructions for performing the operations of the CDM 210. The data acquisition unit may be capable of collecting and managing test and measurement data acquired from TIM 260.

More specifically, the user interface features include audio communication features, video communication features, data security features, and the like, for implementing sophisticated graphical-user-interface technology, enhanced audio and voice recognition facilities for advanced data security features. The user interface features interact with the subscriber at a personal level, very much the way a person would interact with a trusted advisor rather than the rigid and regimented way people typically interact with computers. To accomplish this, the CDM 210 eliminates the need for typing in most commands and it is no longer necessary to memorize passwords or unnatural instructions that use words and language that must be structured in a unique and formal way, specifically for communicating with machines.

The audio communication features include an audio processor 224 coupled to the data processing and data distribution unit 212, a voice recognition unit 222 coupled to the audio processor 224, and a voice synthesizer 226 coupled to the audio processor 224 for two way audio communication between the subscriber and the health maintenance system 100. The CDM 210 utilizes the voice recognition unit 222 to interpret what is being said and may reply using one or more resources available including voice simulation, sound effects, and the video communication features. Also, the voice messages, generated by the CDM 210, may be communicated through the use of a computer-generated moderator that can be personalized to accommodate various subscriber preferences.

The video communication features include a video processor 232 coupled to the data processing and data distribution unit 212, a touchscreen display 228 coupled to the video processor 232, and a digital camera 234 coupled to the video processor 232 for communicating images, messages, alerts, instructions, reports, and general information. The CDM 210 uses a broad array of video clips, animations, caricatures, charts, tables, illustrations, artwork, and other graphical materials. Additionally, a moderator may participate in the video communications by introducing material, presenting information, coordinating topic transitions, and responding to subscriber queries.

To ensure private and secure access to the health maintenance system 100, a biometric security identification unit 236 is employed that may include fingerprint scanners, retinal scanners, voice recognition systems (such as, the voice recognition unit 222), and the like. The biometric security identification unit 236 implements multiple tiers of subscriber identification verification processes for access to the health maintenance system 100.

To minimize the risk of data loss, corruption, unauthorized access, damage, or theft, only limited personal data resides in the PDAU-HS 200a. The subscriber information that is maintained in the PDAU-HS 200a may be stored on an encrypted partition of the memory or storage device 214 of CDM 210. Subscriber data, acquired by the CDM 210, is sent to the DSM-A 280 for encryption, and then forwarded to the CM-A 270 for transmission to the CDPU 400. The subscriber may simply and quickly locate and retrieving their data, however, before sensitive data is displayed, the subscriber's identity must be authenticated through one or more of the designated security identification devices.

For example, at initial access, the subscriber may be asked to register at least four fingerprints, including no less than two from each hand. The subscriber's voice patterns are also registered and maybe used for security screening. For follow-on access, the subscriber may activate the health maintenance system 100 by touching an ENTRY LOCK pad with one finger. A fingerprint scan may be considered a first key and a positive recognition of first key will authorize entry to a CDM ACCESS program of the CDM 210. The CDM ACCESS program includes the introduction screens and activation of the voice recognition system. Sensitive data may be still secure and not accessible through the CDM ACCESS program.

Upon entry to the CDM ACCESS program, a second key requirement may be initiated, wherein the voice recognition system may be activated and the subscriber's voice may be authenticated as the second key. Alternatively, a retinal scanner may be used as a second key, or a fingerprint from another hand may be considered as the second key. On authentication of the first key and the second key, full authorization may be granted (i.e., access to all the features and capabilities of the health maintenance system 100).

If multiple, unsuccessful, attempts are made to proceed past the CDM ACCESS program; a digital photograph, of the person attempting to access the system, will automatically be taken (using the digital camera 234) and stored for future reference. The purpose of this process is to ensure the correct subscriber is authenticated and to identify individuals that may be trying to breech the system. Additionally, the system 100 incorporates a provision that will permit a subscriber to authorize the health maintenance system 100 to allow a second person to function as an authorized representative in order to orally interact with the health maintenance system 100 on behalf of the subscriber. In this case, both voice recognition patterns of the subscriber and the subscriber's representative or assistant may be recorded and stored for future reference.

The data presentations on PDAU-HS 200a may utilize sophisticated audio and graphical user interfaces, including a synthesized moderator, depicted as a realistic looking caricature of a person. The moderator may be responsible for personalizing the system's user interface experience. It may interact with the subscriber and convey interest, concern, patience, encouragement, confidence, professionalism, and like positive factors. The video and audio materials may be presented to the subscriber utilizing the touchscreen display 228 and the audio communication features. Verbal responses, from a subscriber, may be interpreted by the voice recognition unit 222, while other responses may be communicated via the touchscreen display 228. Queries generated by the PDAU-HS 200a incorporate multi-sensory outputs which may integrate audio, graphical, and narrative data simultaneously.

The speed, font style and size, vocabulary, and syntax of data presentations on PDAU-HS 200a may be subjected to an automated calibration process as well as some manual tailoring options. Such calibration process of data presentations on PDAU-HS 200a may automatically set up certain presentation parameters based on known subscriber characteristics, particularly visual and/or hearing impairments, mental acuity, age, and educational level. The presentation parameters may be then further refined in response to the subscriber's repeat-requests and error rates. Also, the subscriber may be given the option to tailor some of cosmetic features of the interface.

The audio and video interface of CDM 120 includes various display screens enabling effective interaction of the subscriber with the health maintenance system 100. At the very beginning, with the activation of the ON switch, a 'START' screen appears with some musical notes sound and small audio/video introductory greeting. The greeting may include legal rights and disclaimer messages as well as brief instructions on how to operate the biometric security identification unit 236. There is extensive collaboration occurring between the PDAU-HS 200a and the CDPU 400. This collaboration is transparent to the subscriber, as they view the various CDM 210 screens being presented. However, the collaborative interactions between the two units (i.e. PDAU-HS and the CDPU) are responsible for every significant security authorization and analytical process.

The unlocking of the biometric security identification unit 236 lock with proper biometric authentication permits access to a 'PDAU ACCESS' screen. The 'PDAU ACCESS' screen incorporates personalized audio/video presentations that include brief introductory comments and a few identification verification queries. In the background, the voice-recognition unit 222 verifies the subscriber's voice patterns, while continuously expanding the voice recognition accuracy and vocabulary of the voice-recognition unit 222. Another function may be tuning of the audio systems acoustics, including microphones and speakers. Upon completion of the introductions and acoustical tuning activities, the PDAU-HS 200a may take up to three digital photographs of the subscriber with the digital camera 234. The subscriber may have the option to select their preferred print before a copy is time-and-date-stamped by the clock/calendar/timer unit 218 and saved by the CDPU 400 as part of current session's history.

Next, a 'PROGRAM' screen appears comprising a series of sequential modules and a market place module, Sequential modules consist of data acquisition module, data analysis module, report module, products and services module, and a monitoring module.

The data acquisition module may be designed to perform the function of collecting and compiling the data used for identifying unique personal, physical, psychological, behavioral and physiological characteristics of the subscriber. This includes personal descriptive data, health history, family health history, physical characteristics, physiological characteristics, body dimensions, mental acuteness, physical fitness, behaviors, medical conditions, allergies, injuries, disabilities, medications, medical therapies/treatments, nutrition, eating patterns, sleep patterns, and the like.

The data compiled by the data acquisition module may be sent to the data analysis module where the compiled data undergoes a plurality of analysis processes including, but not limited to, patterns and trends analysis, abnormality detection, relative comparison, centenarian comparison, behavioral comparison and prognostic assessment.

The patterns and trends analysis process continuously acquires and assesses the current and historical subscriber data in order to identify repetitive patterns and detect early evidence of peculiar deviation that could suggest an abnormality or a sequence of deviations that suggest a change in the subscriber's current condition. Repetitive variations within the subscriber's normal range can be tagged and cross-correlated to influencing factors such as hormonal swings, eating patterns, sleeping patterns, diet, medications, and the like.

Abnormality detection process compares the subscriber's psychological characteristics, physical characteristics, and physiological ranges of performance against authoritative standards and the statistical norm for a similar population group. In this way, aberrations may be detected and assessed to determine whether they represent an anomaly or a health abnormality.

Relative comparison process continuously compares the subscriber's physical, physiological, and psychological characteristics and the subscriber's behaviors, diet, and physical fitness against a similar population group to establish the subscriber's relative condition. Similar population groups include members of the same gender, age, race, physical characteristics, geographical location, and the like.

Centenarian comparison process compares the key subscriber characteristics and historical health patterns against a database of centenarians of the same gender, race, and geographical location. The data may be adjusted to reflect the centenarian's physical and physiological characteristics at an age near that of the subscriber.

Behavioral comparison process compares the subscriber's behavior against those of a similar population group to establish the subscriber's relative behavior. Behavioral aspect includes tobacco usage, alcohol usage, and non-prescription drug usage, eating patterns, sleeping patterns, exposure to sunlight, sexual activity, activity levels, and the like.

The prognostic assessment process uses subscriber health and behavioral patterns, physical characteristics, physiological performance, predisposition to disease, medical histories, physical fitness, family history, health trends, living environment, and the like to calculate the probability of condition improving or deteriorating as well as projecting the probability of a certain health event occurring in the future.

The analyzed data, developed by the data analysis module, may be sent to the report module where the analyzed data may be used for developing and presenting reports including but not limited to the following: nutritional report, condition progression report, abnormalities report, medication conflict report, relative condition report, centenarian comparison report, and prognostic report.

The nutritional report addresses the nutritional requirements of the subscriber based on any nutritional deficits that may have been detected. The condition progression report depicts the characteristic patterns and/or trends pertaining to a specific condition in order to display the changes in a condition, directions of change, and the rate of change. The abnormalities report identifies conditions, physical characteristics, physiological characteristics and behaviors that sufficiently deviate from authoritative standards and/or the norm, of a similar population group, to suggest an abnormality. The medication conflict report identifies the changes in behaviors, sensations, physical and/or physiological characteristics that can suggest an adverse response to a medication or treatment. The relative condition report depicts the relative psychological, physiological, and physical characteristics and condition of a subscriber when compared to the norm of a similar population group. The centenarian comparison report depicts the relative condition as well as behavioral and dietary/nutritional distinctions of the subscriber as compared to a population group of centenarians. The prognostic report addresses the probability that a certain health condition or physical characteristic will improve, remain static, or deteriorate in the future. It also depicts the probable rate of change.

The data in the report module may be sent to the product and services module where subscriber's physical characteristics, physiological performance, behaviors, medical history, current medical treatments, predispositions and preference may then be taken into consideration and used to construct and present a particular strategy, regimen, or service that is highly personalized to meet the specific needs of the subscriber.

Next, the monitoring module consists of monitoring processes that include but is not limited to: condition monitoring, treatment effectiveness monitoring; adverse reaction to medication monitoring, condition progression monitoring; and occupational health surveillance. Additionally, alerts are issued, when health problems are detected, and notifications and/or reminders are issued to ensure the subscriber maintains a certain regimen or follows-through with certain prescribed monitoring procedures and commitments. The condition monitoring process monitors the progression or changes in the subscriber's physical, psychological, physiological and behavioral characteristics due to a disorder or condition. The treatment effectiveness monitoring process includes the monitoring of specific psychological, physical, physiological and behavioral characteristics in order to determine the effectiveness of a prescribed treatment or the progression toward a goal or objective. Adverse reaction to medication monitoring includes the monitoring of specific psychological, physical, physiological and behavioral characteristics in order to detect adverse reactions, interactions, complications and/or adverse side-effects of a drug, medication or treatment. Occupational health surveillance involves monitoring processes sensitized to certain occupational health exposures such as toxic/noxious chemicals; pollutants; and poisons. Occupational health surveillance also includes civil defense health surveillance in regard to population exposures to certain toxic/noxious nuclear, biological and chemical substances.

The marketplace module is accessible at any time after entering the "PROGRAM" screen. The marketplace module collaborates with various programs and historical archives in order to identify, present and make available a personalized line of products to the subscriber. These include consumable goods (i.e. diapers, personal hygiene products, tissues), vitamin and mineral supplements, cosmetics and skin care products, medications (i.e. prescription and nonprescription), dietary & nutritional products, eye care products, baby care products, health related information (i.e. literature, books, videos, audio books, etc.), and the like. Each product may be selected based on the subscriber's expressed interest, past history of use, known consumption rate, proven effectiveness, and the like. The marketplace module tracks the subscriber's use of prescription drugs and may notify a subscriber when a reorder is appropriate—based on the previous quantity purchased and the recommended dosage. The marketplace module may also alert the subscriber if the consumption of a prescription medication, based on a reorder rate, appears to exceed the recommended dosage. All procurements of medicines and other substances that could have an significant effect on the health of a subscriber, may be routed to the data analysis module, report module, product and services module and monitoring module for their consideration when performing their respective tasks.

After accessing the 'PROGRAM' screen, an 'OVERVIEW' screen appears. The 'OVERVIEW' screen may be designed to present an overview of the completed and incomplete exercises or activities, as well as alerts, notifications, and reminders that were issued.

Next, an 'EXIT' screen appears for systematic shut down of certain parts of the health maintenance system 100. The health maintenance system 100 may be not completely shut down, since temperature sensing and other alarm or reminder activities continue even when the health maintenance system 100 may not be in the fully operational mode. On exit, the health maintenance system 100 may also be capable providing a continuous environmental monitoring capability and ongoing alert/reminder functions. If certain environmental parameters are exceeded an audible and visual alarm may be sounded and an alert is automatically transmitted to the CDPU 400. The CDPU 400 then automatically notifies the custodian of the PDAU 200 of the problem. After the subscriber has exited the system 100, the system 100 continues to survey alerts, advisories and notifications. If one or more of these are sufficiently critical to require the subscriber's attention, the system 100 will proceed to the next tier of notification which may include telephone voice messages, beepers, e-mails, notification of an authorized health care provider, and so on.

For maintenance purposes, of the PDAU-HS 200*a*, a built-in test (BIT) functions may be incorporated into the PDAU-HS 200*a* The BIT function enables the health maintenance system 100 to test and maintain itself. The BIT functions ensure that failures can be quickly identified and isolated. The BIT functions focus much of their attention on the CDM 210, CM-A 270, and DSM-A 280 modules as they provide the link between the CDPU 400, PDAU-HS 200*a*, and the subscriber. Once the BIT functions detect a system irregularity or malfunction, the CDM 210 may issue a 'DEGRADED SYSTEM NOTICE', and the CDPU 400 may be notified. The CDPU 400 collaborates with the built-in test equipment (BITE) of the CDM 210 to verify and repair the malfunction. If this remote intervention fails to restore the system to full operational condition, a maintenance service action may be initiated. The maintenance service action incorporates a fault description, repair procedures, automated parts ordering, and service technician notification.

The BIT functions operate in the following ways: power-on BIT, continuous BIT, and initiated BIT. Power-On BIT comprises a series of operational status tests performed every time the system is activated These tests detect the presence and value of key voltages and signals at certain system and subsystem test points. If these voltages and signals are correct, a 'SYSTEM OK' message may be momentarily displayed and the program continues. If a malfunction is detected, a 'MALFUNCTION DETECTED' message may be displayed and instructions for proceeding are provided. The CDPU 400 may be automatically notified of any malfunctions detected and begins to take action to remotely remedy the malfunction. If this action fails, the subscriber will be notified and an on-site maintenance action initiated.

Continuous BIT runs continually in the background, monitoring system and subsystem functions that facilitate communication between the CDPU 400, PDAU-HS 200*a*, and the subscriber. Also key PDAU-HS 200*a* supporting functions are monitored to ensure the PDAU-HS 200*a* is fully operational. Test-program-sets monitor prescribed test points and PASS/FAIL signals based on predetermined criteria. If a malfunction is detected, a message, identifying the failed function, may be displayed and the CDPU 400 will be notified. The CDPU 400 then takes action to remotely remedy the failure. If action fails, the subscriber will be notified and an on-site repair maintenance action initiated.

Initiated BIT may be activated, by the subscriber, when the subscriber suspects a malfunction may have occurred. The tests will verify the malfunction's symptoms and the probability-of-failure associated with the components (i.e. software and hardware) that can cause these symptoms. Once a probable cause is identified, test data in the form of software irregularities, voltages and signals may be acquired to narrow down the probable causes and finally to verify the specific malfunction. When a malfunction is detected, a "MALFUNCTION DETECTED" message may be displayed, along with instructions given to the subscriber on how to proceed, and the CDPU 400 will be notified. The CDPU 400 will take action to remotely remedy the malfunction. If this action fails, the subscriber will be notified and an on-site repair maintenance action initiated.

Figure 5:
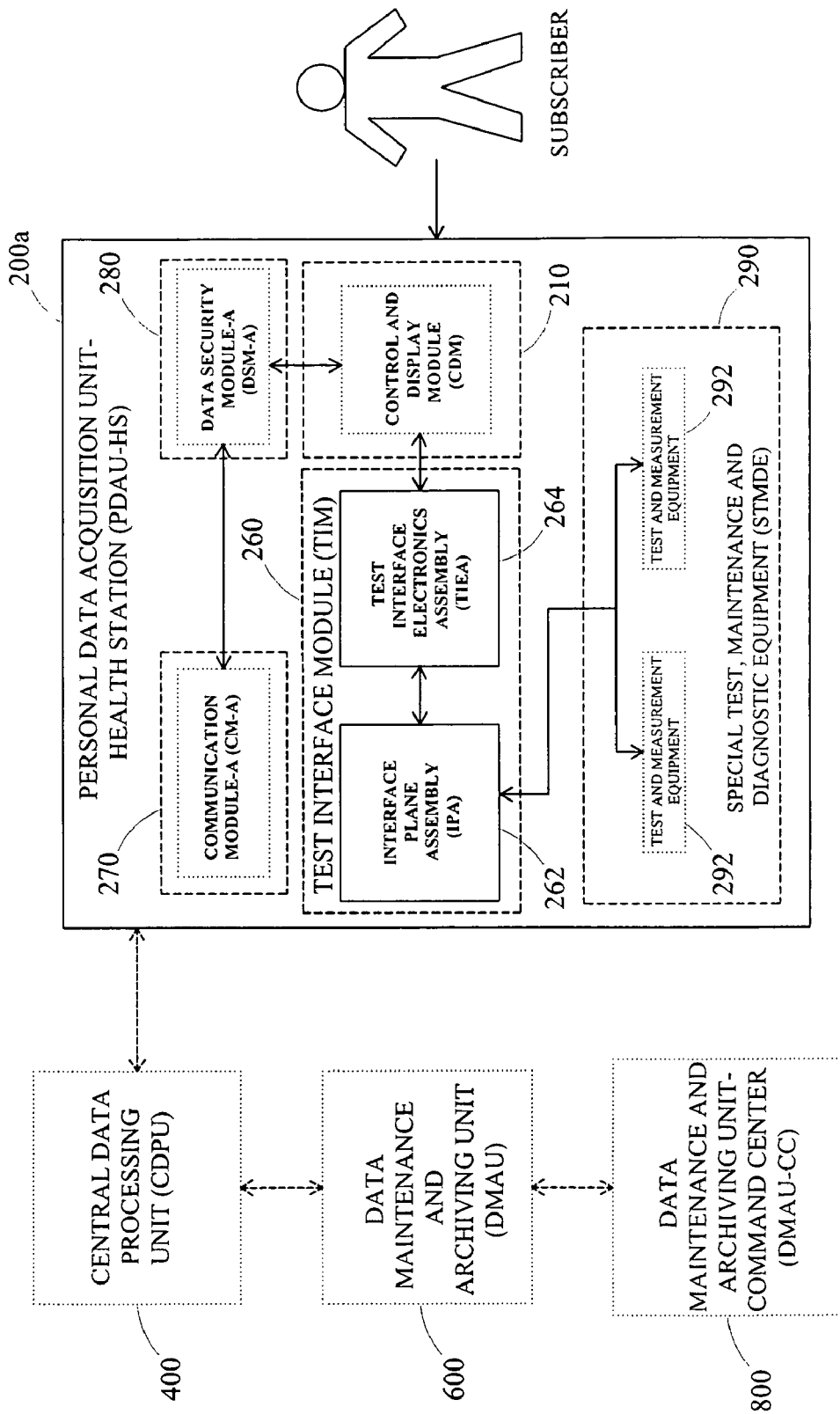
FIG. 5 is a block diagram illustrating components of a test interface module 260 of the personal data acquisition unit-health station 200a, according to an exemplary embodiment of the present invention.

In one embodiment, the TIM 260 is capable of acquiring, processing, and forwarding the test and measurement data collected by the STMDE 290. Referring to FIG. 5, the TIM 260 comprises an interface panel assembly (IPA) 262 and a test interface electronics assembly (TIEA) 264. The IPA 262 provides the electronic interface and connections (connectors, cables, wireless terminals, and the like) between the STMDE 290 and the data acquisition electronics of the TIEA 264. Also, the IPA 262 may incorporate a set of environmental sensors and a complementary set of status indicator lamps.

In detail, the IPA 262 may be designed to support advanced interface technologies and includes an environmentally sealed enclosure, break-free connectors, wiring harnesses (incorporating diagnostic test point leads), and wireless terminals for transmitting signals between sensory devices of the STMDE 290 and the data acquisition electronics of the TIEA 264. Room temperature, air quality, and humidity sensors, incorporated into the IPA 262, may collect and transmit data to the TIEA 264 at regular intervals, even when the PDAU-HS 200a may not be in the fully operational mode.

The CDPU 400, through the PDAU-HS 200a interface, oversees the activities of the TIEA 264 while the TIEA 264 controls the processes of the STMDE 290. The TIEA 264 consists of software and electronics designed to manage the acquisition of test and measurement data, process this data, and forward the processed data to the CDM 210. The CDM 210 may be responsible for interacting with the subscriber. In some cases, the CDM 210 may communicate test and/or measurement set-up procedures to the subscriber and interact with the subscriber during the test and measurement process. In other cases, the CDM 210 will present test and measurement results to the subscriber and respond to subscriber queries.

More specifically, the TIEA 264 receives, processes, and then transmits the data to the CDM 210 for display to the subscriber, and ultimately, transmits the data to the CDPU 400 for processing. Redundancy may be built into the temperature, air quality and humidity sensor package, permitting the software of the TIEA 264 to continuously compare outputs. If the outputs match within the equipment's tolerance range, the values may be considered GOOD. If they do not match, the TIEA 264 may generate an error report and direct the IPA status indicator lamps to light accordingly.

The externally mounted input/output interface devices and sensors of the IPA 262 may include at least one status indicator lamp. The lamps provide the subscriber with feedback regarding the operational status of the interconnects. Each lamp may be easily viewed by the subscriber and may be positioned adjacent to the connectors/terminals they monitor. Additionally, an automated lamp tester may be incorporated into the IPA 262 to test and identify lamp failures and minimize false indications.

Following may be the equipment indication status due to a green lamp: "blinking" of green lamp may indicate that the component may be ready for connection and/or waiting to receive/transmit a signal; green lamp being steady "on" may indicate that the component may be in a go condition, inputs and outputs are as expected and signals fall within an acceptable tolerance range; green lamp in an "off" state may indicate 'not in test mode', 'no power' or 'failed lamp'. Following may be the equipment indication status due to a red lamp: 'blinking' of red lamp may indicate that the component is not ready (cable not connected, device not connected, quality and/or strength of the signal not adequate); red lamp being steady 'on' may indicate that BIT may have detected an error or failure and an intervention may be required; red lamp in an 'off' state may indicate 'not in test mode', 'no power' or 'failed lamp'.

Optionally, the TIEA 264 may automatically register the date, time, temperature, and humidity measurements with each test/measurement reading of STMDE 290 in order to chronologically document the test and the environmental conditions.

Also, the TIEA 264 may have an audible alarm and ALERT and NOTICE capability that may be activated when a test or measurement result is determined to be critical. Critical may be applied to test and measurement readings that indicate a significant change in the subscriber's normal condition and to vital-sign measurements that represent an immediate risk to the subscriber's health. When either of these situations arises, an audible alarm may be activated and an ALERT message, with instructions, may be displayed. When authorized, an ALERT notification may be issued to at least one designated party, such as, a physician or relative. The ALERT notification may consist of an e-mail and/or a digitized voice message.

For maintenance purposes of the PDAU-HS 200a, the TIEA 264 may be designed to respond to temperature, air quality and humidity readings that exceed acceptable levels. In a first situation or level of concern, attention is given to ambient temperatures or temperature, air quality and humidity combinations that cause discomfort, physical stresses and potentially skew the test results. In such a case, the TIEA 264 will momentarily sound a low-level audible alarm, discontinue testing, and notify the CDM 210 and ultimately the CDPU 400 of the situation. The CDM 210 will display a message describing the situation and the CDPU 400 will issue a NOTICE to the parties responsible for maintaining the PDAU 200. The second situation deals with more extreme temperatures and/or air quality that represent inherent health risks. When a certain temperature/air quality thresholds are reached, a moderately loud modulating alarm may be sounded and the volume and rapidity incrementally increase as the temperature increases. At a second threshold, a significantly louder alarm may be sounded and periodically interrupted by a voice message that alerts anyone in the vicinity that high temperatures and/or dangerous air quality levels have been detected and precautionary action may be taken. At both thresholds an ALERT may be transmitted to the CDPU 400 which issues an ALERT notification to the individuals responsible for maintaining the PDAUs 200. If authorized, the CDPU 400 may also issue an ALERT to the local Emergency Services. It is to be noted that the PDAU-HS 200a may detect and respond to the extreme temperatures and air quality even if the PDAU-HS 200a is in 'stand-by' or 'sleep' mode.

The CM-A 270 may be capable of facilitating communications between the PDAU-HS 200a and the CDPU 400. To ensure optimum performance, the CM-A 270 monitors the operational status of the communications hardware and lines (Internet, Intranet, telephone, satellite telephone and the like). If failures or degraded communications are detected, the CM-A 270 may advise the CDM 210 and the CDPU 400 which, in turn, may initiate verification and fault-location procedures.

Once communications are verified to be operational, the CM-A 270 may check the incoming data to ensure it is uncorrupted and intact. When data is determined to be corrupted or incomplete, the CM-A 270 directs the CDPU 400 to resubmit. Also, the CM-A 270 may function as a checkpoint for outgoing data, verifying the messages are complete and the messages have been correctly compressed and encrypted.

The CM-A 270 may be considered as first tier of security. Incoming data may be subjected to filters and firewalls to prevent unauthorized access and to stop or neutralize infections. When unauthorized attempts to access or infect data are detected, the CM-A 270 goes into a protective mode, advising the CDPU 400 and engaging additional shields and protective procedures. Upon notification, the CDPU 400 re-scans and further encrypts their out-going data. The fresh data may be then transmitted to the PDAU-HS 200a with separately transmitted special coded instructions.

The DSM-A 280 may be responsible for the compression and encryption of data being transmitted to the CDPU 400 and for the decompression and decrypting of data transmitted from the CDPU 400 to the PDAU-HS 200a. Also, the DSM-A 280 functions as a second-tier firewall and security filter/screen, preventing unauthorized penetration of the PDAU 400 and eliminating or neutralizing infections.

The DSM-A 280 routinely scans the PDAU software for anomalies and abnormalities that may suggest infection, corruption, or an unauthorized intrusion attempt. When at least one of these situations is detected, the segment of software affected may be assessed, isolated, and if possible repaired. Software determined to be non-repairable locally may be taken off-line and an error report may be generated. In such cases, the DSM-A 280 interacts with the CDPU 400 to acquire a patch, software upgrade, or software download which may be then installed and the system rechecked. When unauthorized attempts to tamper with or access software are detected, the DSM-A 280 may direct the PDAU-HS 200a to enter a protective-mode and shut down.

The test and measurement equipments 292 include both invasive and non-invasive test and measurement equipments. The test and measurement equipments 292 include, but are not limited to, mechanical equipment, electrical equipment, electrochemical equipment, electromechanical equipment, photographic equipment, thermographic equipment, chemical equipment, and hydraulic equipment, optical, acoustic and opto-electronic devices for taking an array of physical and physiological measurements.

The test and measurement equipment 292 may incorporate mechanical, electromechanical, optical and acoustic sensors and other devices that come in contact with the body. The contact surfaces of these sensors and devices may be made of materials that are non-conducive to microbial growth. Special provisions may be made to ensure the materials used are inherently hygienic, easy to clean, and, when appropriate, protected by hygienic disposable covers. The sensors, of the test and measurement equipment 292, maybe used to quantitatively measure physical dimensions, body weight, body fat, range of motion, strength, body density, muscle endurance, skin translucence, skin elasticity, visual performance, hearing performance and the like. Specialized electronic sensors may detect various types of low-level electronic signals produced by the body as well as the body's electrical conductivity and response to external electrical stimuli. The optical, opto-electronic sensors may produce an electrical signal proportional to the amount of light incident on its active area. The digital imagery sensors have high resolution with broad spectral array sensitivity, magnification, and high frame speed, and are used to capture full body to microscopic imagery. These images may be accurately scaled, magnified, and viewed directly or subjected to digital enhancements that may detect abnormalities, color and shape changes, and dimensional measurement. In some cases, the digital imagery sensors may capture light wavelengths that are unique to inflammation, infection or secretions produced by certain microbes.

Exemplary test and measurement equipments 292 include the following: fat detectors, that monitor and measure the body fat ratio and fat distribution as quantitative values; strength detectors that utilize various measurement devices and sensors to measure quantitative values of resistance and force exerted by the bodies various muscles and muscle groups at different ranges of motion; skin analyzers that may include digital radiometric imagery and fluorescent spectroscopy which are capable of detecting, gauging and monitoring a broad range of skin conditions; breathe analyzers such as laser absorption spectroscopy capable of quantitatively identifying minute chemical markers or other traces of a condition or malady; body temperature sensors and scanners; scales that are used to measure the subscriber's weight; measuring devices used to measure the subscriber's height and body dimensions; blood pressure monitors; respiratory rate monitors; heart rate monitors; heart rhythm monitors; blood oxygen analyzers capable of calculating relative percentage of hemoglobin saturated with oxygen during the arterial pulse; saliva analyzers that detects biochemical imbalances; vision analysis capable of evaluating visual acuity, refraction, visual field and color vision; hearing analysis derived from a series of tests that include pure tone tests, speech tests and middle ear tests; hair analysis that detects the presence and concentration of drugs, chemical residues, toxins, heavy metals, and radiation present in the body as well as vitamin and mineral deficiencies; fingernail analyzers that includes fingernail scanning to detect susceptibility to bone disease (osteoporosis) and other testing to determine exposure to heavy metal toxicity, blood chemistry analysis; combinations of at least two or more of these devices that are capable of collecting quantitative measurements that support the detection and diagnosis of health conditions.

Redundancy of critical circuits and components may be incorporated into design of the STMDE 290 to minimize the effects of single-point failures and degradation. Time-synchronized sensing, which consists of operating multiple sensors simultaneously or consecutively, measuring the same feature, may be used to increase accuracy by cross-checking and normalizing readings. These readings are automatically transmitted through the IPA 262 to the TIEA 264 where they are compared, weighted, and a most-probable-value calculated. These probable values are then transmitted to the CDM 210 for display and transmission to the CDPU 400, where the probable values are recorded and subjected to various types of analysis and tracking.

Figure 6:
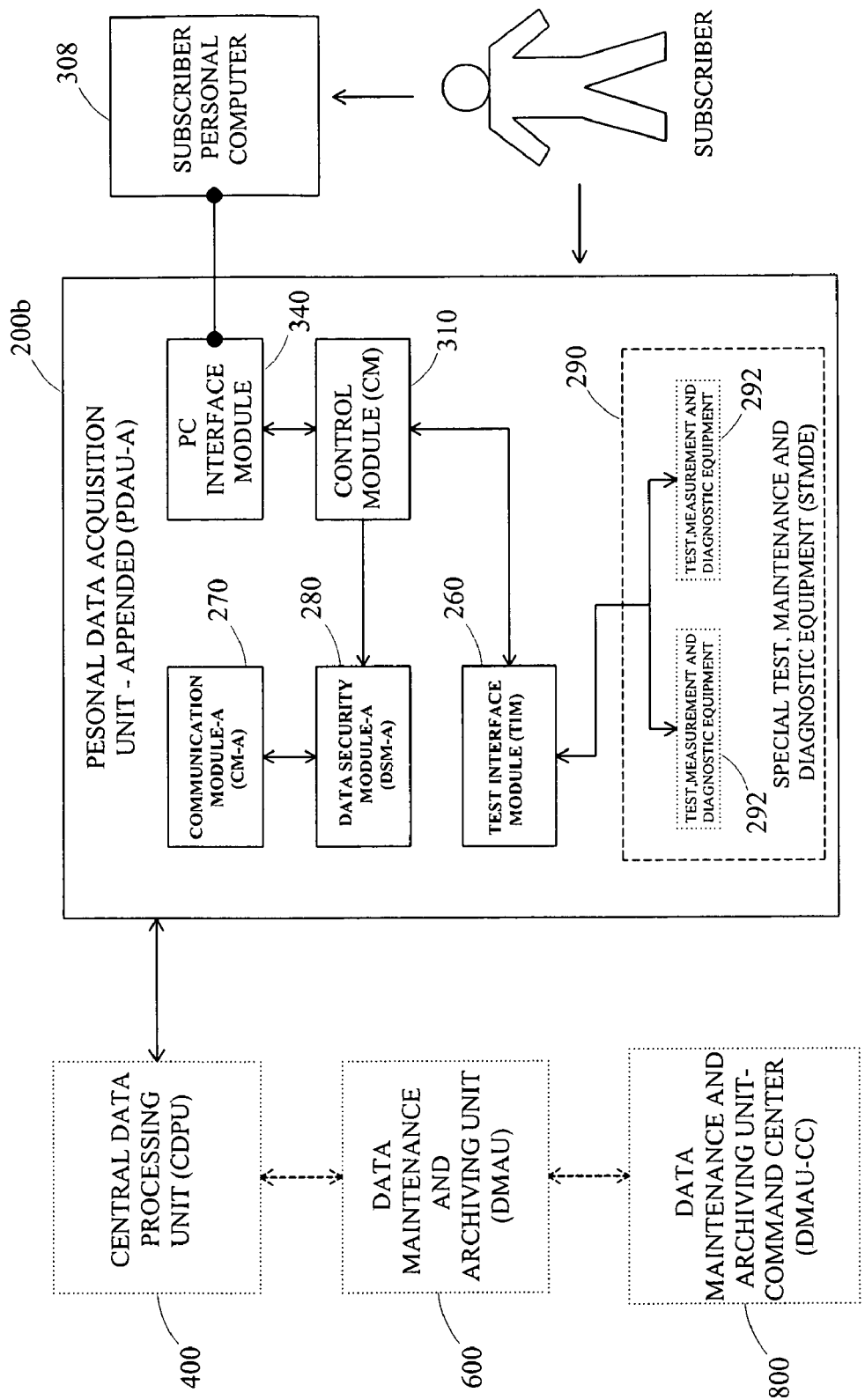
FIG. 6 is a block diagram of a personal data acquisition unit-appended 200b, according to an exemplary embodiment of the present invention.

In another embodiment, the PDAU 200 may be in the form of an appended unit to be used in combination with a subscriber's personal computer 308 (desktops, laptops, tablets, personal digital assistants, and the like). This configuration is referred to as personal data acquisition unit-appended (PDAU-A) 200b (See FIG. 6). The PDAU-A 200b comprises a package of hardware accessories and software that may be designed to work in conjunction with the subscriber's personal computer 330. Generally, the user-interface capabilities of PDAU-A 200b are limited when compared to PDAU-HS 200a, since, the PDAU-A 200b may be dependent on the capabilities and features of the subscriber's personal computer 308.

More specifically, the PDAU-A 200b (See FIG. 6) and PDAU-HS 200a (See FIG. 3) have a similar core construction, except for a control module (CM) 310 of PDAU-A 200b, which replaces the CDM 210 of the PDAU-HS 200a, and the addition of a personal computer interface module (PCIM) 340 in the PDAU-A 200b. The remaining modules of PDAU-A 200b and PDAU-HS 200a are sufficiently similar (i.e., the PDAU-A 200b may have TIM 260, CM-A 270, DSM-A 280, and STMDE 290, as described above for PDAU-HS 200a).

Figure 7:
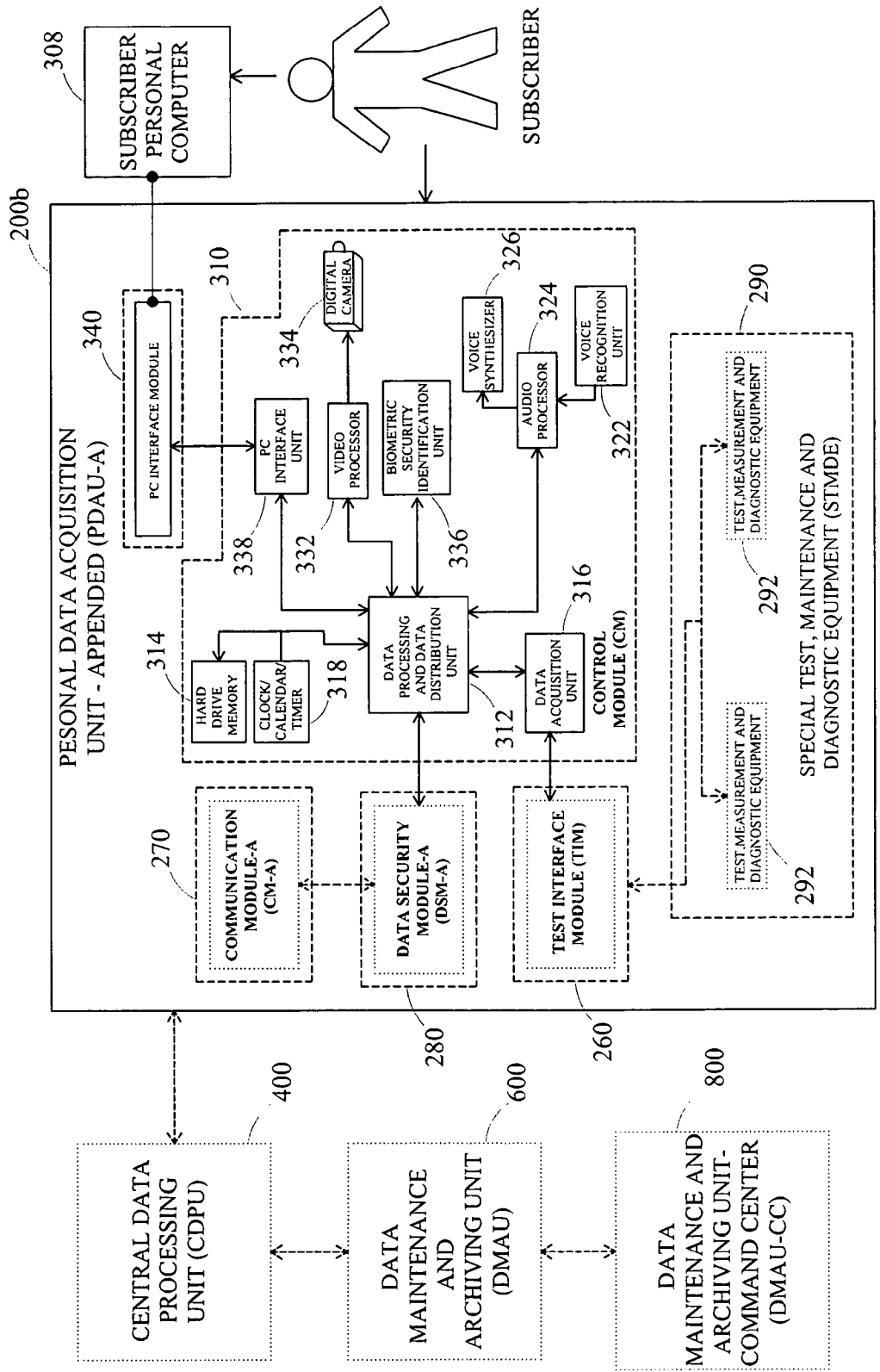
FIG. 7 is a block diagram illustrating components of a control module 310 of the personal data acquisition unit-appended 200b, according to an exemplary embodiment of the present invention.

As shown in FIG. 7, the CM 310 may have a data processing and data distribution unit 312 (also referred to as data processor 312), similar to the data processor 212 of the CDM; a memory or storage 314 coupled to the data processing and data distribution unit 312, similar to memory or storage 214 of the CDM 210; a data acquisition unit 316 coupled to the data processing and data distribution unit 312; a clock/calendar/timer unit 318 coupled to the data processing and data distribution unit 312; a PC interface unit 338 for communication with the PCIM 340, the PC interface unit is coupled to the data processing and data distribution unit 312; and a plurality of user interface components (software programs and hardware components) to support interaction with the subscriber through the subscriber's personal computer 308, the user interface components are coupled to the data processing and data distribution unit 312.

More specifically, the user interface components support the PDAU-A's 200b audio communication features, video communication features, data security features, and the like. These components are responsible for implementing sophisticated graphical-user-interface technology, enhanced audio and voice recognition capabilities, and advanced data security capabilities. The audio communication features include: an audio processor 324, coupled to the data processing and data distribution unit 312; a voice recognition unit 322, coupled to the audio processor 324; and a voice synthesizer 326, coupled to the audio processor for two way audio communication between the subscriber and the health maintenance system 100. The video communication features include: a video processor 332, coupled to the data processing and data distribution unit 312; and a digital camera 334, coupled to the video processor 332. The video communication features work in combination with the subscriber's personal computer 308 display/touch screen to communicate messages, image, alerts, instructions, reports, and general information. Some of the audio and video communication features of the CM 310 may be subject to capabilities of the subscriber's personal computer 308.

Access, through the PDAU-A 200b, to the health maintenance system 100 may be protected using a data security feature, more specifically, using a biometric security identification unit 336, coupled to the data processing and data distribution unit 312, similar to the biometric security identification unit 236. Data security feature also enables in marinating the privacy of the subscriber while using the health maintenance system 100. The biometric security identification unit 336 may include fingerprint scanners, retinal scanners, image scanners, voice recognition units (such as, the voice recognition unit 322), and the like. The PDAU-A 200b may have limited access is to the health maintenance system 100 due to the less secure nature of the PDAU-A 200b and the subscriber's personal computer 308.

The data presentation features of the PDAU-A 200b may be designed similar to and in-part interchangeable with, the PDAU-HS 200a. However, the PDAU-A 200b utilizes the subscriber's personal computer 308 to display the graphical material and to perform various audio interactions. Touchscreen capability may not be present but live buttons may be displayed that may be activated by a mouse 'click'.

The PCIM 340 may be capable of functioning as an interconnect between the PDAU-A 200b and the subscriber's personal computer 308. More specifically, the PCIM 340 provides the electronics and software necessary to transmit audio, video, and data between the PDAU-A 200b and the subscriber's personal computer 308. The PCIM incorporates the following features: wireless and cable transmission capability, system security (filters, firewalls, and the like); circuit protection; and high speed buses.

Additionally, the PDAU-A 200b may have an accessory kit including a set of components that may be used to interconnect and modify the subscriber's personal computer 308. Exemplary components in the accessory kit include, but are not limited to, interconnect cables, an operational software package, and interface circuit card assembly. The interconnect cables may be used to connect the PDAU-A 200b to the subscriber's personal computer 308. Cable connections are provided as an option, in lieu of a wireless connection. The operation software package may be loaded into the subscriber's personal computer 308, once the interface circuit card assembly has been installed. The operational software package permits the PDAU-A 200b and the subscriber's personal computer 308 to effectively interact, using a compatible operating system, and graphics/audio hardware and software applications. The interface circuit card assembly optimizes the electronic and software interactions between the PDAU-A 200b and the subscriber's personal computer 308. Also, the interface circuit card assembly incorporates system security features and graphic/audio enhancement features.

In another embodiment, the PDAU 200 may be in the form of a subscriber's personal computer installed with health maintenance system software. The health maintenance system software may be issued to individual subscribers. The health maintenance system software, stored on a CD, DVD, or other storage device, may be easily installed on a subscriber's personal computer having a standard operating system and high speed internet connection. The health maintenance system software includes special subscriber identification verification features, data security capabilities, internet connection features, health maintenance system log-on support, and communication features. These, in combination with features of the subscriber's personal computer, facilitate interacting with the subscriber's personal computer and the CDPU 400. A subscriber may assess the health maintenance system 100 from their home or office and then, among other things, check the status of their health condition, add new information, report on the progression of a condition and shop on health maintenance system 100.

Broadly, the function of the CDPU 400 maybe to interact with the subscriber through the PDAU 200. These interactions are generally transparent to the subscriber and tightly choreographed and synchronized. The CDPU 400 may be responsible for directing and controlling the data acquisition processes, assimilating subscriber inputs, analyzing the subscriber's inputs, developing health condition assessments, and offering personalized health strategies and services. In one embodiment, the CDPUs 400 are capable of performing the following functions: data acquisition; data analysis; health product customization and development; and condition monitoring.

The data acquisition function may be a collaborative effort between a CDPU 400 and a prescribed network of PDAUs 200 within a designated region of the CDPU 400. As used herein, PDAU 200 addresses the PDAU-HS 200a, PDAU-A 200b and certain features of a subscriber's personal computer with the health maintenance system software installed. The data acquisition parameters are established by the CDPU 400 and then transmitted to the PDAUs 200. The data acquisition function addresses the acquisition, organization, tracking, and distribution of a broad array of personal information and health related data. More specifically, data acquisition includes the identification of specific data element requirements, acquiring or collecting these data elements, and then compiling and structuring the data elements in a format that may be easily manipulated, correlated, and assessed.

Exemplary data categories include, but are not limited to, personal identification data, physical characteristics data, health profile data, family health history data, drug and vitamin/mineral supplement data, health baseline data, diet and nutritional data, environmental exposure data, and behavioral data.

The personal identification data comprises essential personal information that facilitates the identification of an individual and the establishment of core demographic characteristics. For example, the personal identification data includes name, address, residence history, age, gender, race, ethnicity, education, sexual preference, martial status, living arrangements, marital history, children, occupation, work history, home and work environments, travel history, military service history, genealogy, relationships, recreational activities and the like. Sensitive information, such as, name and street address, maybe segregated and coded for privacy and security.

The physical characteristics data includes height, weight, body fat ratio, body symmetry and dimensions, skin shade and texture, eye color, hair growth/color and texture, strength symmetry, endurance, coordination, posture, gait, nail growth and features, feet size, physical peculiarities, physical deformities, growths, blemishes, teeth and gums, flexibility, and the like. These characteristics are useful in establishing the subscriber's physical uniqueness as well as their membership in population groups that share certain characteristics.

The health profile data comprises a broad array of information pertaining to the subscriber's psychological and physiological characteristics and condition, medical history data, hazardous and toxic material exposure data, allergies data, disabilities, reproductive history, depression data, family (genealogy) health history data stress level data, mental condition data, current health conditions data, physical sensitivities and pain data, activity level and physical fitness data, illnesses history data, history of injuries data, chronic conditions data, visual acuity data, night vision data, hearing acuity data, reaction time data and the like. The health profile data also incorporates the results of quantitative tests including blood chemistry tests, breath analysis (i.e. laser absorption spectroscopy), medical imaging (i.e. x-rays, magnetic resonance imaging, lithotripsy, computed tomography, fluorescence spectroscopy, ultrasounds, thermographs, and others), photographic imaging, and other psychological, physical, and physiological tests originating with the health maintenance system 100 or imported from other sources. When necessary, the CDPU 400 may import health profile data (i.e. mammograms, x-rays, magnetic resonance images, blood tests, medical records and the like) from outside sources.

The family health history addresses the health conditions and unique characteristics of the subscriber's living and deceased blood relatives. The family health history data is comprised of personal description data, physical description data, physical characteristics, demographic data, occupational data, disabilities, behaviors, health and medical histories, and the like. The family history data collection includes names, birthdates, place of birth, number of children (including genders and birthdates), places of residency, health histories, ages at death, height, weight, physical and health peculiarities, chronic conditions, sensitivities/allergies, disease history, cause of death, health conditions at time of death, history of injuries, deformities, visual acuity, hearing acuity, mental condition and acuity, disabilities, occupations/professions, medication history (including diagnosis, treatments, test results, evaluations, and the like), reproductive histories, alcohol and drug usage, blood types, and other psychological, physical, physiological and behavioral details that would be useful in the identification of genetic characteristics and predispositions.

The drug and vitamin/mineral supplement data comprises a detailed history of prescription and non-prescription drugs, vitamin supplements, herbs, and mineral supplement usages. Included in the history may be the item description, dosage, frequency taken, date started, reason for taking, date stopped, reason for stopping, and observed effects, side effects, reactions, and the like.

The health baseline data may, in part, be derived from information compiled in previous databases including, the personal identification data, physical characteristics data and health profile data Certain key psychological characteristics (i.e. depression, confusion, neurosis and other like mental conditions or mental cognitive peculiarities), physical characteristics (i.e. height, weight, body fat ratio, posture, flexibility, mobility, hair growth, hair color, skin color/tone, eye color and the like), physiological characteristics (i.e. visual performance, hearing performance, blood pressure, heart rate, repertory rate, heart rhythm, blood chemistry, and other major organ system performance characteristics), and medical conditions that are recorded over an extended period of time. The resulting database will depict each characteristic separately and their respective performance values. Next, the data may be subject to a patterns-analysis, which identifies repetitive fluctuations in order to establish predictable patterns, ranges of fluctuation and rate of change. Where possible, certain pattern fluctuations are linked to predictable cycles, such as, time-of-day, seasons, and biological cycles. Next, the subscriber's physical, psychological, physiological and behavioral characteristics (including patterns) are assessed relative to an authoritative standards and norms of similar population groups. The resulting compilation of data becomes a baseline or reference-point to which new data, representing the latest health condition of the subscriber, may be compared. The comparison will indicate whether the new data is consistent with or deviates from the baseline. The deviations may be positive (improvements in a condition), negative (evidence of deterioration), or they may be evidence of a new condition or abnormality.

The diet and nutritional data (also referred to as diet and nutritional profile) systematically records the subscriber's dietary and nutritional intake and eating practices over time. For example, data may be obtained by periodically requesting information on what, how much, and when the subscriber ate and/or drank. The requests for information may target the time period of about 2 to about 8 hours preceding the request and the requests may be systematically timed so that every conscious hour may be eventually subjected to multiple requests for information. Next, the subscriber's food intake (including drinks and snacks) may be subjected to a comprehensive nutritional evaluation which establishes the nutritional value of the ingested substances including the amount and type of vitamins, minerals, calories, protein, carbohydrates, antioxidants, sodium, fats and the like. Each meal and snack (including drinks) is assessed and registered in order to construct a detailed, chronological image of the subscriber's dietary intake. This data may be subjected to pattern-analysis in order to identify repetitive patterns and associate fluctuations within the patterns to their influencing factors. The resulting diet and nutritional profile may be continuously updated in order to represent the subscriber's most current dietary intake. As an additional feature, specific food and drink descriptions and quantities consumed are documented and used to identify dietary preferences and predispositions.

The environmental exposure data consists of those environmental characteristics that describe both natural environmental considerations (i.e. natural occurrences such as outside air temperature, humidity, sunlight, naturally occurring toxic/hazardous emissions, terrain, rain, water temperature, and others), manmade or man influenced environments considerations (i.e. air conditioning, heating, ergonomics, lighting, pollution and contamination, traffic, and the like), and hazardous environments (i.e. intentional and unintentional manmade or man caused environmental considerations such as exposure to dangerous situations and dangerous substances such as nuclear materials, toxic or hazardous biological substances, and toxic or hazardous chemicals, and the like).

The behavior data (also referred to as behavior profile) documents a variety of behaviors that are known to affect wellness and longevity. To simplify behavior assessment, and, as used herein, 'behaviors' are strictly defined as the actions taken by a person to relax, deal with stress, and occupy free time. The behaviors, amount of time spent in these behaviors, and the degree or intensity in which the subscriber participates in a behavior may be registered. The behaviors may be divided into three general categories. The first category includes behaviors that involve taking a substance (alcohol, tobacco, drugs, food, coffee, and the like). The second category includes behaviors that require doing something (jogging, watching sports, gambling, watching TV, playing golf, conversations, sewing, and the like). The third category addresses coping impulses which include impulsive reactions to anger, affection, fear, confusion, and embarrassment. The data acquired may be subjected to a pattern-analysis to identify repetitive patterns and tendencies.

The data analysis function organizes and digests data and searches for correlations between the data elements themselves and between the data elements and reference materials (for example, medical encyclopedias, studies, prescription drug reference materials and the like). The data elements are evaluated individually and as a set or group. As a group, certain relationships may become evident and their cumulative effect may suggest a condition or abnormality that may not otherwise be recognized. Upon the discovery of a possible abnormality, the symptoms may be further assessed to identify probable causes and possible interventions. Also, the data analysis process may be programmed to detect patterns or trends that provide early indications of a condition that may require attention. When compiled and evaluated collectively, these data elements contribute to establishment of a 'health baseline' against which changes may be measured and the effectiveness or response to prescribed medical therapies may be evaluated. In one embodiment, for the health maintenance system 100, the subscriber's health conditions are continuously re-evaluated and the data may be sensitized in respect to age, gender, race, ethnicity, occupation, geographical location and psychological/physical/physiological characteristics. This sensitization significantly influences the analysis and may be reflected in the insightful and highly personalized services offered.

The data elements are subjected to five analytical processes: comparative analysis; patterns and trends analysis; reference data correlation; relative condition; abnormality detection.

In the comparative analysis process, the subscriber's individual health characteristic, or a group of their characteristics, may be compared against an authoritative standard. The authoritative standard may be tailored to reflect a similar population group including age, gender, race, ethnicity and geographical location. Also, the comparative analysis may be used to compare the subscriber's current health characteristics against their historical characteristics in order to detect changes.

In the patterns and trends analysis process, data may be mathematically assessed in order to calculate patterns and determine whether there is evidence of a trend. As used herein, 'patterns' are defined as measurements, values or events that fluctuate over time, in a predictable manner, within an established range. In some cases, patterns may be linked to regularly or irregularly occurring causes (i.e. high blood pressure after a long commute in heavy traffic, difficulty sleeping after a business trip or vacation, weight gain during a holiday, and the like). Trends are defined as directional deviations from an established pattern. Exemplary categories of information, addressed by the patterns and trends analysis process, includes but are not limited to, fluctuations in psychological, physical, physiological, and behavioral characteristic as well as the frequency and severity of specific illnesses and the frequency and severity of specific injuries. Other factors may also be incorporated into the patterns and trends analysis. These include recent diet, recent travel history, seasonal events, season, recent weather, changes in environment, marital relationships, vacations, recreational activities, and the like.

The reference data correlation process searches for meaningful relationships or correlations between the subscriber's unique health characteristics and authoritative sources that include demographic data, census data, health statistics, nutritional data, environmental pollutants and contaminants affects data, nuclear contamination affects data, hazardous/toxic biological substance exposure affects data, hazardous/toxic chemical exposure affects data, drug usage affects and toxicity data, and other health-related source materials. These correlations may greatly enhance the probability of linking the subscriber's abnormal psychological, physical, physiological, and behavioral characteristics to certain known conditions and ultimately to their causes and to recognized health behavior modifications and treatments.

The relative condition process continuously compares the subscriber's most recent psychological, physical, physiological, and behavioral characteristics against the authoritative standards and similar population groups in order to gauge the subscriber's relative condition. A variation of this process includes the comparison of the subscriber to a population group of centenarians that share certain key characteristics that may include the same gender, race, ethnicity, geographical region, and the like.

In the abnormality detection process, searches are performed for correlation between data elements that may suggest evidence of a condition or abnormality. The abnormality detection process may be designed to detect early evidence of an abnormality or unusual change in the subscriber's condition. In one embodiment, the abnormality detection comprises the following activities: abnormality screening, pattern deviation; behavioral changes; and adverse reaction detection. In abnormality screening, the subscriber's psychological, physical, and physiological characteristics may be continuously screened in order to identify those that fall outside of the authoritative standards or norms. In pattern deviation, current health characteristics may be screened against previous established ranges of fluctuation or patterns in order to identify deviations. Deviations consist of those most recent health characteristics that fall outside of the normal range of fluctuation and therefore suggest a change in the subscriber's condition. In behavioral changes, the subscriber's most recent behaviors and relationships are compared against previous behaviors and relationships in order to identify abnormal behavior, relative to authoritative standards or norms of a similar population group, and unusual changes or precipitating events that could affect or be affected by the subscriber's health condition. In adverse reaction detection, the subscriber's initial participation in a prescription drug program triggers an assessment of their health history. This assessment identifies evidence of any previous adverse reactions or side effects to the particular drug being used or similar drug. Also, subscribers that use prescription drugs have their psychological, physical, physiological, and behavioral characteristics closely monitored to detect early evidence of known adverse reactions and side effects.

The health product, service, program and health regime customization and development function may be initiated by an 'action-request' or as a 'deductive-response'. Action-requests may be submitted, by the subscriber, as a request for assistance or information. The deductive-response may be generated by a program, within the CDPU 400, and may be a recommendation to the subscriber in response to the program's assessment of new or existing data. In one embodiment, the health product development process involves two phases: categorization phase; and strategy and solution phase. The categorization phase involves the screening of data to identify key topics and subject matter which is then linked to at least one product, service, program, or regime category or combination of categories, based on the subscriber's identifying characteristics and condition The strategy and solution phase involves the identification of selectively complied product, service, program, or regime categories or combination of categories that target a particular condition, and further personalizing the strategy to be compatible with subscriber's current situation, environment, predispositions, and preferences.

The categorization phase may include but is not limited to the following categories: aging category, in-home care and support category, weight management category, behavior assessment and modification category, strength and endurance category, health condition monitoring and assessment category, childhood development category, mental cognition and acuity assessment category, chronic illness assessment and management/treatment category, medical condition assessment and treatment category, occupational health assessment and response category, food and beverage contamination effects and treatment category, medical treatment effectiveness monitoring category, pregnancy monitoring and management category, nutrition assessment and nutritional intervention strategy category, nuclear/biological/chemical exposure assessment and response category, environmental toxin exposure assessment and response category, common chemical exposure assessment and chemical affects treatment category, fertility and reproduction assessment and treatment category, sexual performance assessment and enhancement category, aging affects assessment and mitigation category, appearance assessment and enhancement category, drug affects monitoring and assessment category, endurance assessment and enhancement category, and the like.

The aging category may include the following features: appearance, hormone levels, strength, endurance/flexibility, visual performance, hearing performance, and mental cognition. The appearance feature addresses the skin condition, eye clarity, gait, muscle tone, hair and scalp condition, posture, teeth, gums, joint appearance, involuntary movement, and the like. The hormone level addresses hormonal imbalances caused by menopause and andropause as well as other hormonal conditions exasperated by age. The strength/endurance/flexibility addresses muscular strength, aerobic condition, muscular/skeletal flexibility, balance, gait, mobility, muscle mass, bone mass, and the like.

The in-home care and support category may include the following features: nutritional evaluation, personal hygiene and sanitation, hydration, grocery listings and acquisition, appointment reminder, sunlight exposure, eating habits, sleeping habits, activity and exercise, and the like.

The weight management category may include the following features: optimal weight, body mass index, fat ratio, weight control, and weight distribution. Further, the weight management category addresses metabolic assessment, diet and nutrition, exercise and behavior modification, and the like.

The behavior assessment and modification category may include the following features: alcohol and tobacco usage, eating habits sleeping habits, stress response, substance abuse, activity level, and the like.

The strength and endurance category may include the following features: aerobic conditioning, mobility, resistance training, body shaping, balance and coordination, posture, flexibility, and the like.

The condition monitoring process may be an essential intelligent surveillance activity that selectively tracks and registers certain subscriber psychological, physical, physiological, environmental, and behavioral characteristics. In one embodiment, the condition monitoring process comprises up-date monitoring and special monitoring. The up-date monitoring process may be activated whenever certain new health values or a change in a condition is entered into the system. Up-date monitoring may performed over a relatively short period of time and may be designed to verify a condition or detect deviations from the subscriber's personal norms, authoritative standards, and the population norms, as well as detect abnormalities. Special monitoring may be conducted over an extended period of time and may consist of many of the same features as the up-date monitoring. Special monitoring may incorporating the systematic tracking of certain predetermined psychological, physical, physiological, environmental, and behavioral characteristics in order to identify patterns, detect anomalies or collect data needed to better diagnose a condition.

Additionally, the CDPUs 400 are capable of performing the following functions: prognostics; health history data analysis; and health history archiving. In the prognostics process, a broad array of current and historical health and behavioral data elements is considered. These include age, gender, race, ethnicity, geographical location, current health data (including medical conditions and severity), health history data, family health history, known predispositions, activity level, relationships, historical rates of recovery and the like. Scientific and medical knowledge, authoritative standards and comparative assessments, to similar population groups, may be used in order to calculate the statistical probability that a situation or condition will improve, degrade, or remain static. More specifically this includes calculating the probable rate at which a certain condition will change. The accuracy of these projections may be enhanced as the subscriber's psychological, physical, and physiological characteristics are tracked over longer periods of time and as more detailed, accurate, and complete health historical and diagnostic data is made available. Also, the prognostics process may be used to project the rate of aging and predict the most probable ailments. This may be particularly important since these projections help establish intervention strategies that may prevent or mitigate some of their effects.

The data acquisition processes, of the CDPU 400, result in the compilation of important subscriber health histories that establishes the individual's condition and predispositions. Cumulatively, these health histories may establish local population patterns and trends. This information may then be assimilated by various algorithms, resident in the, CDPU 400, in order to establish and prioritize individual subscriber health monitoring priorities and criteria. The CDPUs 400 continuously collects the data as part of the subscriber profile development and updating process. Copies of certain data elements are transmitted to the DMAU 600 and DMAU-CC 800 for collective analysis and archiving. The DMAU 600 compares the health history inputs of each CDPU 400 against other CDPUs 400 within its region in order to establish or recalibrate the statistical parameters that make up the subscriber population norms. As part of this process, the DMAU 600 may identify regional peculiarities and abnormalities which are then transmitted to their respective CDPU 400 for further processing and dissemination to the subscriber. Certain types of cumulative health assessments (i.e. evidence of nuclear, biological or chemical contamination) may be sent to the authorized health authorities when appropriate. Also, the DMAU 600 maintains an archive copy of the subscriber's health history archive as long as an individual is an active subscriber. When needed to comply with laws, regulations or other requirements, the DMAU 600 may also store the subscriber's permanent health history archives once a subscriber is no longer an active member or is deceased.

The DMAU 600 may automatically forward certain health history data to the DMAU-CC 800 which may also analyze the cumulative data and compare the collective DMAU 600 health history inputs against each individual DMAU 600 input. In this way, the DMAU-CC 800 may identify deviations from the cumulative norm and continuously recalibrate the master resource databases to ensure they reflect the current situation. The DMAU-CC 800 may permanently archive the subscriber's health history without regard to subscriber status (active, inactive, or deceased). The subscriber, or an authorized subscriber designee, may request a copy of these health histories through their respective PDAU 200 and CDPU 400. This request will be forwarded to the DMAU-CC 800 for retrieval and response.

Figure 8:
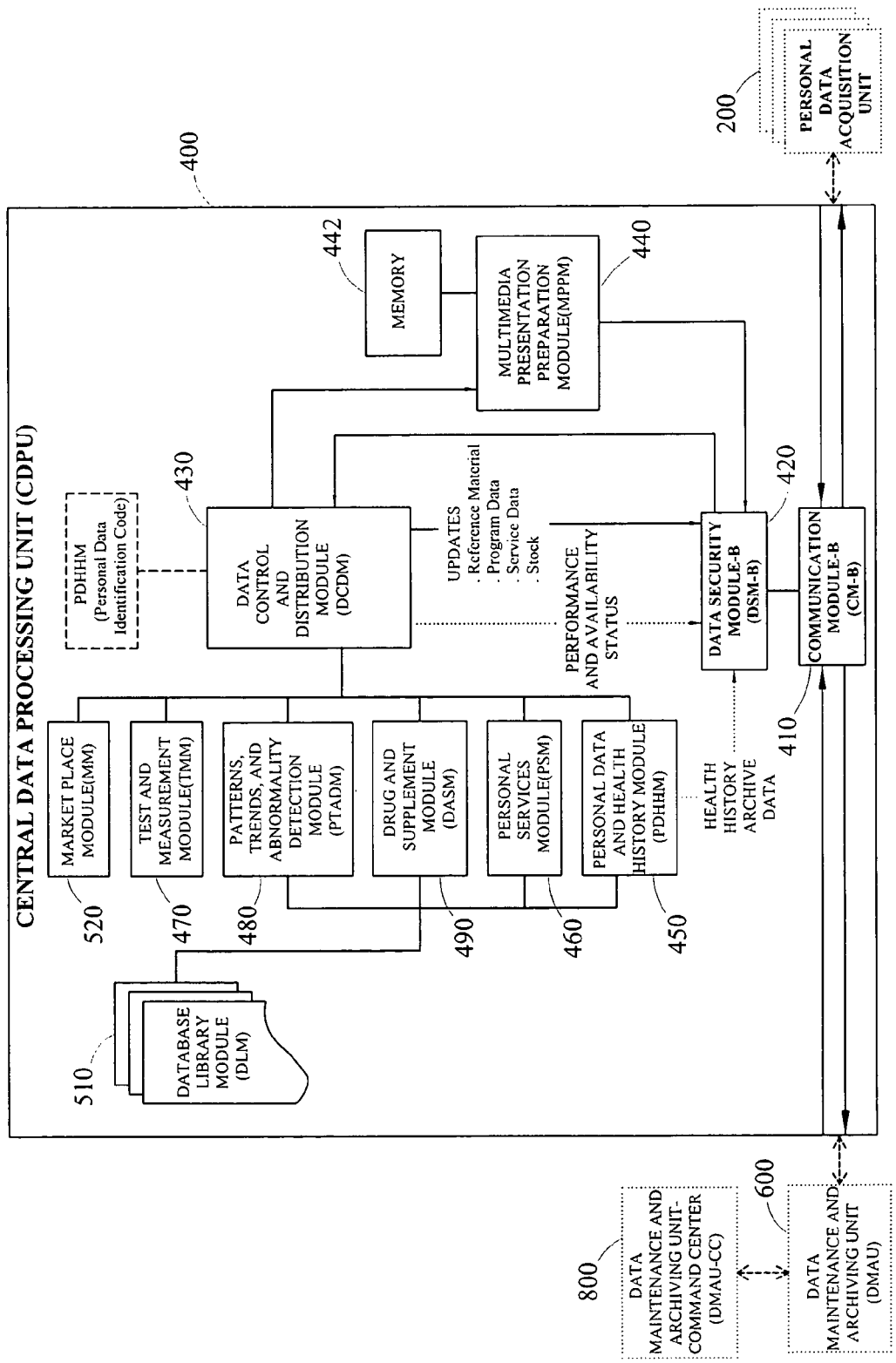
FIG. 8 is a block diagram of a central data processing unit 400, according to an exemplary embodiment of the present invention.

Referring to FIG. 8, the CDPU 400 comprises: a second communication module referred herein as a communication module-B (CM-B) 410; a second data security module, coupled to the CM-B 410, referred herein as a data security module-B (DSM-B) 420; a data control and distribution module (DCDM) 430 coupled to DSM-B 420; a multimedia presentation preparation module (MPPM) 440 coupled to DCDM 430; a personal data and health history module (PDHHM) 450 coupled to DCDM 430; a personal services module (PSM) 460, coupled to DCDM 430; a test and measurements module (TMM) 470 coupled to DCDM 430; a patterns, trends and abnormality detection module (PTADM) 480 coupled to DCDM 430; a drug and supplement module (DASM) 490 coupled to DCDM 430; a database library module (DLM) 510 coupled to the PTADM 480, DASM 490, PSM 460, and PDHHM 450; and a marketplace module (MM) 520 coupled to DCDM 430.

The CM-B 410 maybe responsible for facilitating communications between the CDPU 400 and its network of PDAUs 200, and the CDPU 400 and DMAU 600. The CDPU 400 may be generally centrally located within a geographical region and transmits and receives data over a suitable communications network (for example, high-speed internet, intranet connection, and the like). The CM-B 410 receives encrypted incoming data, verifies data origin and completeness, and then routes the data to the DSM-B 420 for decrypting. The DSM-B 420 routes outgoing encrypted data to the CM-B 410 which verifies data completeness and transmits it to the designated PDAU 200. Also, the CM-B 410 may be responsible for monitoring the communication network connections to verify operational status.

The DSM-B 420 may have numerous security and privacy related responsibilities which, among other things, include decrypting and encrypting data that may be transmitted from or to the PDAU 200 and DMAU 600. Also, the DSM-B 420 may be responsible for establishing internal subscriber privacy by segregating the subscriber identification (for example, name, address, and the like) from incoming messages and assigning a subscriber identification code. The subscriber's identification may be linked to the subscriber's identification code and stored separately in a secure and isolated database. The DSM-B 420 may remove the subscriber identification code and may re-establish the subscriber's identification for outgoing messages that are to be transmitted to the PDAU 200.

Figure 9:
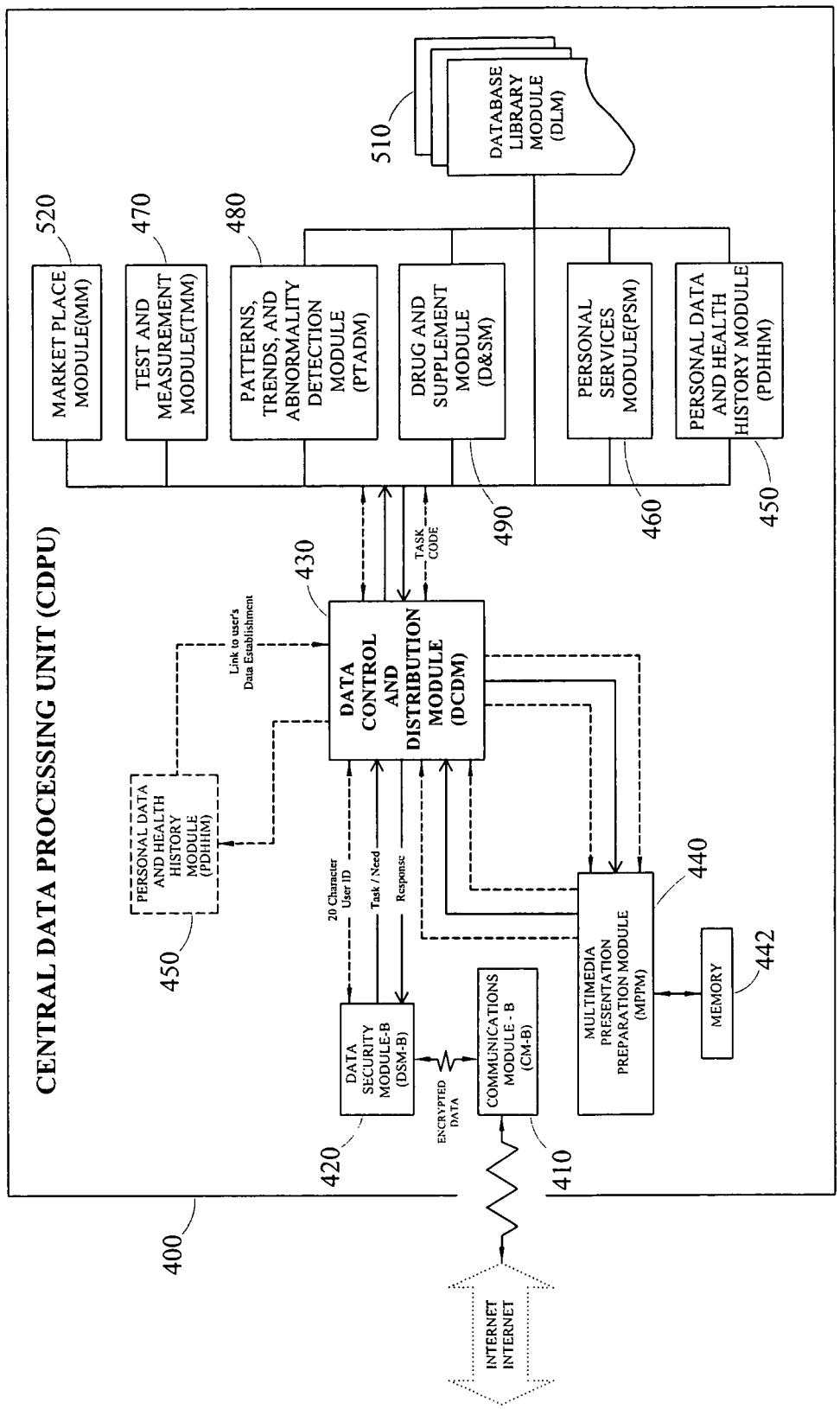
FIG. 9 is a block diagram illustrating functioning of a data control and distribution module 430 of the central data processing unit 400.

The DCDM 430 may be responsible for registering incoming actions know as tasks/needs, linking certain subscriber data to the actions, assigning task codes, distributing action assignments to at least one module of the CDPU 400, verifying responses and distributing outgoing responses (See FIG. 9).

The MPPM 440 interacts with the DCDM 430 by preparing outputs of the DCDM 430 for presentation to the subscriber. The MPPM 440 modifies the outgoing responses by compiling and organizing the material in a coherent presentational format including scripting and choreographing the moderator and tailoring graphics, vocabulary and syntax level, and the like. The responses are further processed to ensure material flow is logical and fluid When the multimedia conversion is completed, the MPPM 440 may route the presentation to the DCDM 430 for distribution to the PDAU 200 and the subscriber. The MPPM 440 may save a copy of the presentation material in a memory 442 (preferably a long-term memory) coupled with the MPPM 440. This permits later retrieval, reuse, and modification of the data.

The PDHHM 450 may be capable of acquiring, maintaining, analyzing, distributing and reporting-on a broad array of subscriber data. The data acquired includes the data categories described above, (i.e., personal identification data, physical characteristics data, health profile data, physiological characteristics data, family health history, drug and supplement data, prescription and non-prescription drug history data, diet and nutritional data, personal health baseline data, behavior data and the like). The PDHHM 450 may systematically organize the data to facilitate analysis, rapid cross-correlation and retrieval. As data is entered, programs within the PDHHM 450 collaborate with the PTADM 480 and subject the data to various analytical processes, including pattern and trend identification, abnormality detection, and relative condition assessment.

Figure 10:
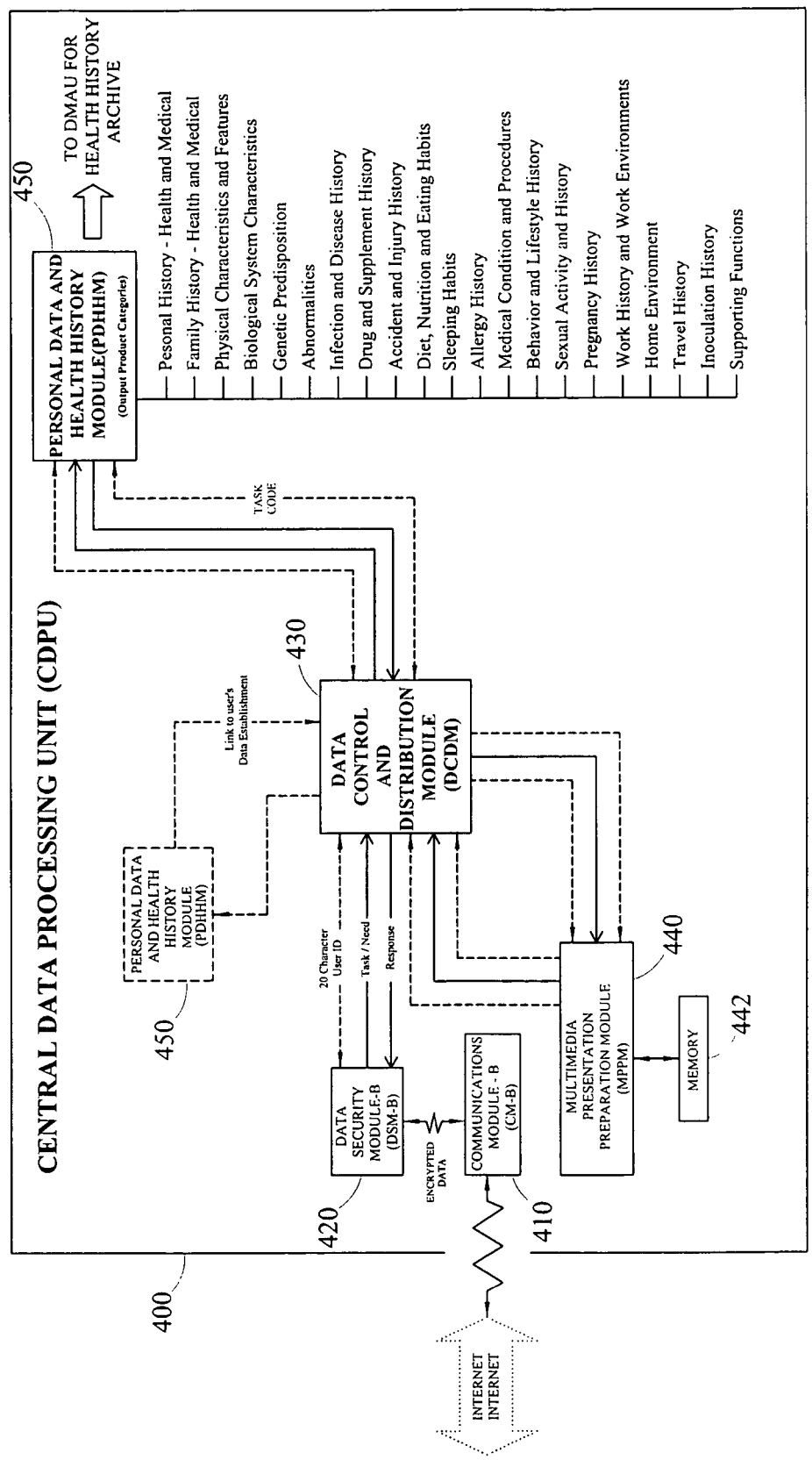
FIG. 10 is a block diagram illustrating output reports generated by a personal data and health history module 450 of the central data processing unit 400, according to an exemplary embodiment of the present invention.

The data analysis may be used to generate a plurality of reports (See FIG. 10). These reports are available in various formats and levels of technical detail. Among other things, the PDHHM 450 output reports offer the subscriber a comprehensive overview of their relative condition and provide early warning of any abnormalities that may be detected. As shown in FIG. 10, exemplary reports include, personal history-health and medical reports; family history-health and medical reports; physical characteristic and physical feature reports; biological system characteristics reports; genetic predispositions reports; abnormalities reports; infection and disease history reports; physiological conditions reports; drug and supplement history reports; accident and injury history reports; diet, nutrition, and eating habits reports; sleeping habits reports; allergy history reports; medical conditions, procedures and treatments reports; behavior and lifestyle history reports; sexual activity and sexual history reports; pregnancy history report; physical activity reports; work history and work environment reports; exposure to toxic nuclear, biological and chemical substances reports; exposure to occupational and environmental hazardous substance reports; home environment safety reports; travel history reports; maturation and aging reports; mental cognition and mental acuity reports; chronic condition monitoring reports; inoculation history report; supporting function report; and the like. Also, the PDHHM 450 compiles some of the subscriber health history data elements for periodic transmission to the DMAU 600.

The PSM 460 may be capable of assessing inputs from the subscriber and from other modules in order to establish the subscriber's condition and corresponding needs. Next, the PSM 460 may identify the skeletal health product, program, health service or/and health regime that most closely satisfy these needs. The health products may then be tailored to accommodate particular physical and physiological characteristics of the subscriber, as well as their predispositions and preferences (See FIG. 11). When implemented, a suite of CDPU 400 modules collaborate in monitoring the effectiveness of the health product. The PSM 460 may continuously assess this feedback and may introduce product modifications or updates that further enhance product effectiveness. Also, the monitoring may detect adverse reactions to a product which will trigger the PSM 460 to discontinue the product or dramatically modify the application.

Figure 11:
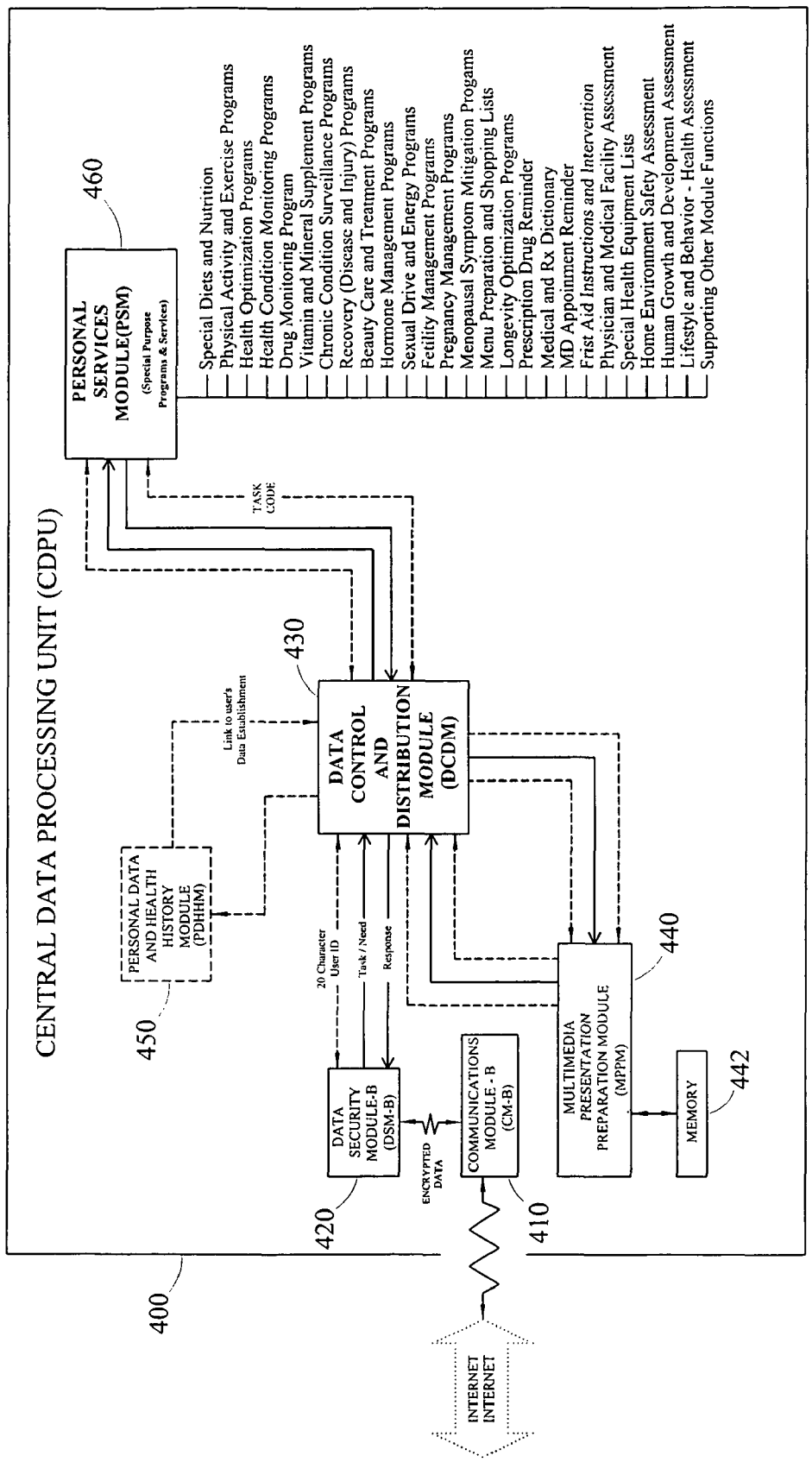
FIG. 11 is a block diagram illustrating health products provided by a personal services module 460 of the central data processing unit 400, according to an exemplary embodiment of the present invention.

As shown in FIG. 11, exemplary PSM 460 products include, but are not limited to, the health products, programs, services and regimes derived from a partial group consisting of special diet and nutrition programs; physical activity and exercise programs; health optimization programs; assisted living programs; health condition monitoring programs; drug monitoring programs; vitamin and mineral supplement programs; chronic condition surveillance programs; disease and injury recovery programs; beauty care and treatment programs; hormone management programs; sexual drive and energy programs; fertility management programs; pregnancy management programs, menopausal/andropause symptom mitigation programs; menu preparation and shopping programs; longevity optimization programs; prescription drug reminder programs; medical and Rx dictionary programs; MD appointment reminder programs; first aid instruction and intervention programs; physician and medical facility assessment programs; special health equipment lists; home environment safety assessment programs; human growth and development assessment programs; nuclear, biological and chemical decontamination and treatment programs; lifestyle and behavior-health assessment program; plus other health related products, programs, and services. The personal service module also supports the activities of other modules.

Figure 12:
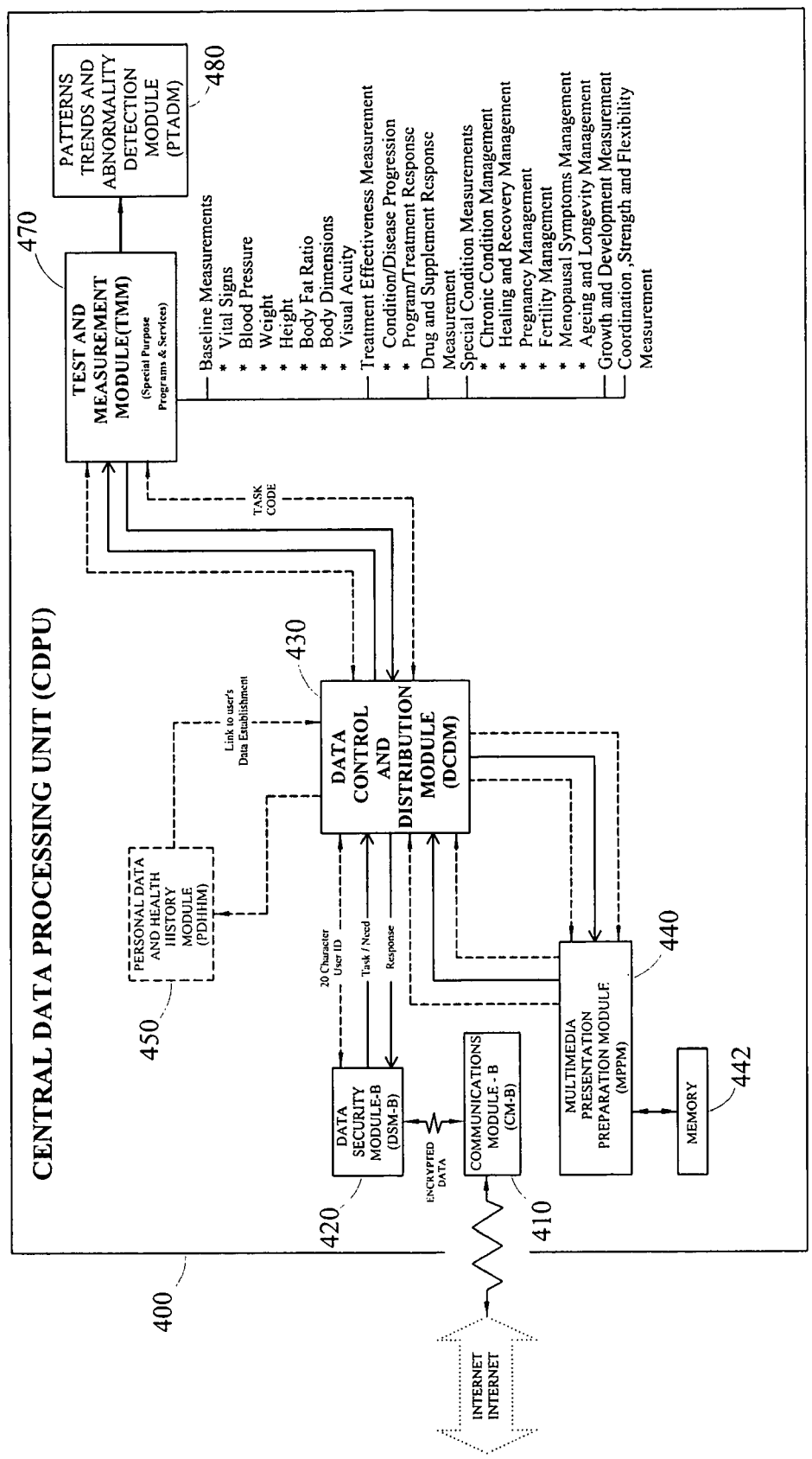
FIG. 12 is a block diagram illustrating measurement categories provided by a test and measurements module 470 of the central data processing unit 400, according to an exemplary embodiment of the present invention.

The TMM 470 may be capable of specifying and acquiring an array of physical and biological system measurements. As shown in FIG. 12, the measurements fall into the following categories: baseline measurement; treatment effectiveness measurements; drug and supplement response measurements; special condition measurements; growth and development measurements; coordination, strength and flexibility measurements; environmental toxicity measurements, and the like. The baseline measurements include vital signs, height, weight, blood pressure, body fat ratios, body dimensions, hearing acuity, visual acuity, sensation, and other standard physical and physiological measurements needed to establish the subscriber's baseline health and physical characteristics. The baseline measurement process may utilize a chronological series of measurements that are taken at predetermined times. When compiled, these measurements establish a dispersion pattern that constitutes the normal range within which the subscriber functions.

The treatment effectiveness measurements process acquires a specific set of psychological, physical, behavioral and/or physiological measurements that are directly and indirectly subject to the affects of a health maintenance system prescribed product/program or a physician-prescribed medicine or medical treatment. The measured values are compared against the subscriber's pre-treatment baseline and against authoritative standards in order to determine whether progress is being made. The measurements are also sensitized to detect symptoms of potential complications or adverse reactions that may be associated with the treatment and the subscriber's known sensitivities. The treatment effectiveness measurements include quantitative condition/disease rate-of-progression measurements; treatment side-effects, complications and adverse reactions measurements; treatment objectives and schedule achievement measurements; treatment application and adherence measurements; risk assessment measurements; comparative treatment assessment measurements; and the like.

The special condition measurements include chronic condition management; healing and recovery management; pregnancy management; fertility management; menopause/andropause symptom management, aging and longevity management, maturation management; weight management; dietary monitoring; sleep monitoring; physical activity monitoring, mental cognition and mental acuity monitoring; toxic nuclear, biological and chemical health effects exposure monitoring, monitoring of health effects resulting from exposure to hazardous materials; and the like. The special condition measurements relate to a set of measurements taken to monitor a stage of life, natural biological events, chronic condition and/or long-term disability in order to gauge the progress, complications or degradation that may be occurring. For example, aging and longevity management relates to set of measurements taken to assess the subscriber's fitness, psychological characteristics, physical characteristics, and physiological condition relative to their age while taking into consideration their gender, race, ethnicity and geographical location. The growth and development measurements relate to a set of measurements taken to assess a child's physical, physiological, and mental development relative to their age and taking into consideration their gender, race, ethnicity and geographical location.

The drug and supplement response measurements are selected from the group consisting of: drug/supplement side-effects, interactions, complications and adverse reaction measurements; drug/supplement objectives and schedule achievement measurements; drug/supplement dosage and schedule adherence measurements; drug/supplement risk assessment measurements; comparative drug/supplement assessment measurements; and the like.

The environmental toxicity measurements are selected from the group consisting of: toxic heavy-metal exposure measurements; environmental poisons exposure measurements; parasite exposure measurements; mildew and spore exposure measurements; infectious/poisonous-insect exposure measurements; infectious-animal exposure measurements; hazardous chemical exposure measurements; and the like.

Figure 13:
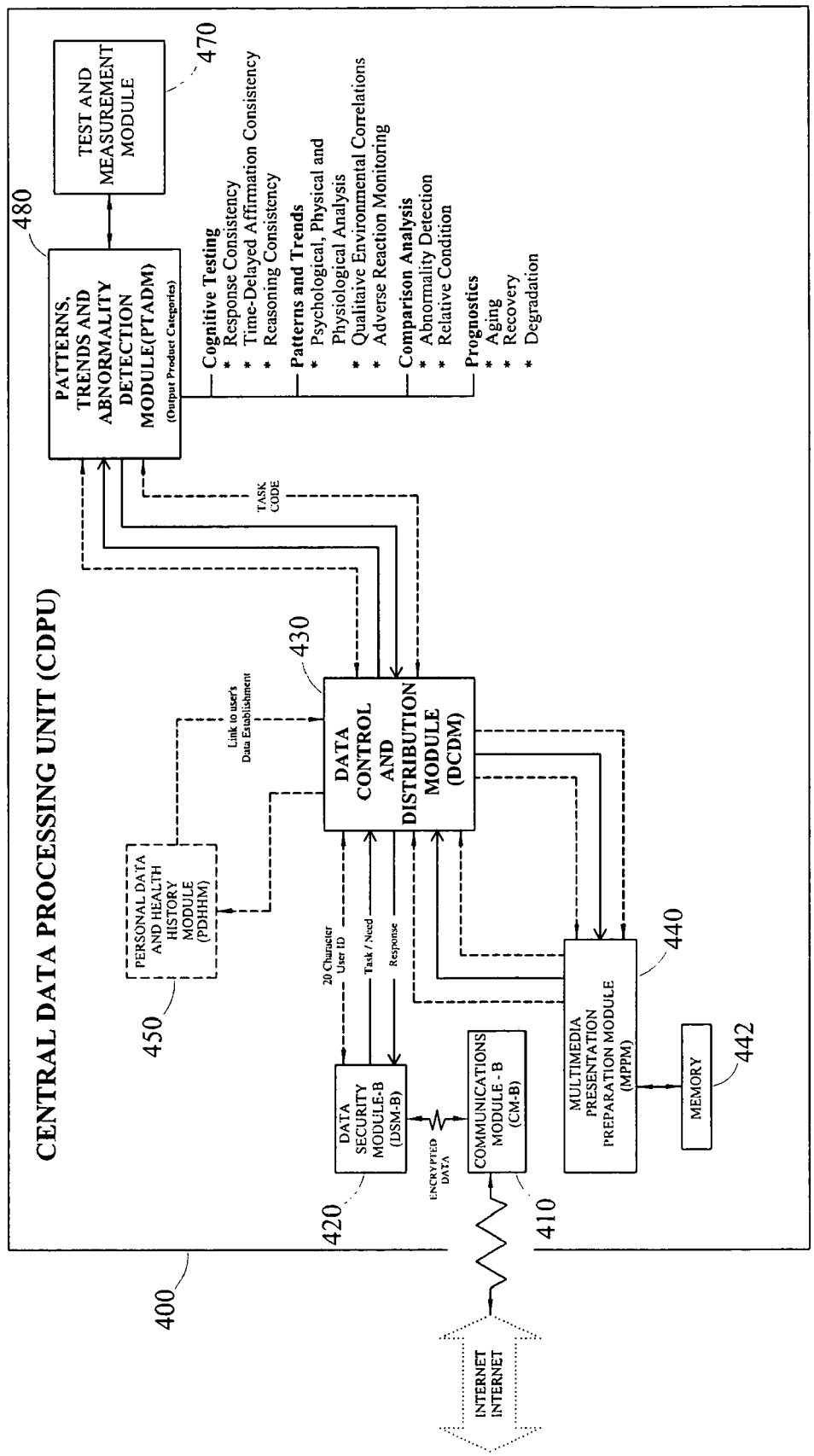
FIG. 13 is a block diagram illustrating analysis process categories of a patterns, trends, and abnormality detection module 480 of the central data processing unit 400, according to an exemplary embodiment of the present invention.

The TMM 470 does not directly analyze the measured data but forwards it to the PTADM 480 for analysis. The PTADM 480 may be capable of automatically collecting, recording, and analyzing a broad array of inputs provided by the PDHHM 450 and TMM 470. As shown in FIG. 13, the analysis process may be divided into four categories: cognitive testing (also known as cognition); patterns and trends analysis; comparison analysis; and prognostics.

As used herein, 'cognition' refers to human memory and reasoning. Cognition may be of particular interest since effectively interacting with the health maintenance system 100 requires exercising a number of basic cognitive skills. The interactions themselves may be considered as cognitive tests that are designed to detect comprehension, logic, and consistency (memory). The PTADM 480 collaborates with the PDHHM 450 to incorporate and monitor a set of specially formulated questions into the data acquisition process. The test questions are indistinguishable from other questions and use the same commonly used vocabulary and easily understood syntax. The question presentations have been standardized and the responses calibrated against those responses provided by a similar population group (e.g. same gender, age, race, ethnicity, educational level, geographical location, general health, and the like). The PTADM 480 monitors responses to these questions over time to gauge the subscriber's sustained acuteness.

In mental acuity and cognitive testing, the following methodologies may be applied: responsive consistency, time-delayed affirmation consistency; and reasoning consistency; mental fatigue tracking and comparison; word and graphic association and recognition; and the like. For responsive consistency, in one embodiment, the PTADM 480 may incorporate several sets of three similar straight-forward questions into various segments of the data acquisition process. The questions may be presented over a relatively short period of time. The PTADM 480 tracks the responses for consistency. If a statistically significant pattern of inconsistency detected, a similar sequence of questions may be presented to verify the observation. Once a cognition issue has been detected, the enhanced application of graphics may be included, syntax simplified and the presentation speed may be slightly slowed. Also, variables, such as, the volume of audible signals, particularly those of higher frequency, may be modulated to ensure the affects of hearing degradation and background noise are mitigated. The results of the test questions may be recorded for reference.

The time-delayed affirmation consistency focuses on the affirmation of current responses as compared to responses provided during a previous session with an extended period between sessions. The PTADM 480 constructs a special group of questions that clarify or expand-on previously supplied information. The subscriber's answers essentially affirm the initial responses by providing relatively simple supporting details, such as, timeframes, locations, and the like. The key exercise may be separating the initial query from the follow-up affirmation query by a meaningful period of time. The results of the test questions may be recorded for reference.

The reasoning consistency methodology focuses on basic mental reasoning. The PTADM 480 may formulate a set of similar questions that have two or more segments requiring a modest amount of judgment and logical deduction. The complexity of the questions may be minimized and would normally be indistinguishable from other questions. The elapsed time responding and the consistency of responses are recorded for reference. Reasoning consistency questions, as do non-test questions, offer inconclusive response options, such as, 'I don't know' or 'I don't understand'. The frequency of inconclusive test question responses and the ratio of inconclusive responses between test questions and not-test questions may be recorded for reference and result in modification of the presentation.

The cognitive testing responses are compiled and the results of each series of questions are assessed to determine whether patterns and trends are present. When peculiar changes in cognition or distinctive abnormalities are identified and verified, the subscriber may be encouraged to complete a special cognition test. The results of the cognition test may be standardized and may be produced as a report suitable for presentation to a physician, physiologist, or other health professional.

As shown in FIG. 13, the patterns and trends analysis may be divided into following categories: psychological, physical and physiological characteristics pattern and trend analysis; qualitative environmental pattern and trend correlations; and adverse reaction monitoring and pattern and trend association. In psychological, physical and physiological characteristics pattern and trend analysis, the PTADM 480 may systematically acquire, record, and analyze psychological, physical and physiological measurements provided by the TMM 470 and the PDHHM 450. The analysis establishes, among other things, the frequency distribution, standard deviation, and central tendencies of these measurements. The results may be then used to identify a predictable pattern that depicts the subscriber's normal condition including fluctuation within a given range. Once, patterns have been established and verified over a suitable period of time, new inputs may be analyzed to determine whether they are consistent with the pattern. New inputs that deviate from the usual pattern (outside of the normal range of fluctuation) may be tracked. If a series or string of deviations is detected, they are considered to be a trend and strongly suggest a change in the subscriber's normal condition. The deviations may indicate a positive or negative change. Negative changes may not be necessarily severe enough to indicate an abnormality, but may offer an early warning of movement towards a condition.

In qualitative environmental pattern and trend correlations, the PTADM 480 and PDHHM 450 collaborate to determine whether there are correlations between the quantifiable behavioral, physical and physiological patterns and situational/environmental conditions, such as, travel, eating pattern or diet change, tobacco usage, alcohol usage, marital status, family health, season, time of day, relocation, employment environment, social events, recreational activities, and the like. Once significant evidence of a correlation may have been established, the behavioral/physical/physiological condition pattern may be enhanced to incorporate the correlating events. At this point, new inputs may be monitored to determine whether they are consistent with the established patterns. If a string of deviations is detected, they are considered a trend and strongly suggest a change in the subscriber's normal condition. The deviations may indicate a positive or a negative change. Negative changes may not be necessarily severe enough to indicate an abnormality, but may offer an early warning of movement towards a condition.

In adverse reaction monitoring, the health maintenance system 100 recognizes that misdiagnosis, failure-to-diagnose, and medical errors occur and may often have serious, if not catastrophic, consequences. To ensure the subscriber and their physician are kept aware of the effects of a treatment; the health maintenance system 100 may assign a high priority to tracking certain psychological, physical, physiological, and behavioral characteristics. When a subscriber may have been medically diagnosed and may actively be treated for a condition or disease, the TMM 470 and PTADM 480 may be provided certain specific characteristics to track. These characteristics may be selected because they are known to provide the best indications of an adverse reaction or complication. These characteristics are recorded during or immediately following the medical treatment and then at predetermined intervals between treatments. The values are systematically compared against each other and against the subscriber's baseline condition prior to the commencement of treatment. Positive and negative deviations between the patterns may be registered. If the negative deviations (i.e. degradation in health) are sufficiently serious and/or represent a trend, the DCDM 430 may be prompted to immediately notify the subscriber and their physician. Also, the PTADM 480 systematically documents, assesses, and graphs subscriber vital signs directly corresponding to the approximate time of a medical treatment and the sequence of follow-up measurements in order to detect peculiarities between measurements and to compare the measurements to the subscriber's baselined vital signs. In this way, the vital sign deviations may receive particular attention and offer early-warning of adverse reactions that may be health threatening. Adverse reaction monitoring may be designed to quickly provide the subscriber and their physician with useful and accurate information so that informed and timely decisions can be made.

As shown in FIG. 13, the comparison analysis may be divided into following categories: abnormality detection; relative condition; and comparison of the subscriber's historical patterns and trends against current patterns and trends for detecting shifts or changes. In abnormality detection, the PTADM 480 may assess the subscriber's behaviors, psychological, physical, and physiological characteristics to determine whether the values fall outside a normal-range. As used herein, 'normal-range' may be determined by comparing the subscriber's characteristics to authoritative standards and those of a similar population group. Also, the correlations between the subscriber's current characteristics and historical characteristics may be assessed. A single peculiar characteristic may not indicate an abnormality by itself, but correlations between two or more characteristics may suggest the presence of an abnormality.

The subscriber's behavioral, psychological, physical, and physiological characteristics are subjected to comparative analysis to establish the subscriber's condition relative to those of similar population groups. Optionally, the subscriber's characteristics are compared against those of centenarians (i.e., people who have lived for hundred years or more) in order to identify those characteristics that are conducive to longevity and those that may suggest impairments to longevity.

In prognostics, the historical patterns and trends of particular behavioral, physical, physiological, psychological characteristics may be analyzed independently and in various collective configurations in order to establish the statistical probability that certain health related events or conditions will occur, remain static, degrade, or improve. The analysis may be enhanced by applying various weightings to a host of influencing factors that include but are not limited to existing medical conditions, condition severities, general health, mental conditions, physical fitness; attitude, family health histories, treatment effectiveness, rates of change in a condition, rates of recovery from previous conditions, as well as the age, gender, race, ethnicity, occupation, environmental considerations and the like. The prognostics process utilizes authoritative standards, medical research, nutritional research, studies, pharmaceutical data, case studies, and the like. Prognostics may become more detailed and accurate as more subscriber history data becomes available. When the prognostics efforts of the PTADM 480 result in a high level of confidence that a certain condition may appear, improve or worsen in the future, the DCDM 430 may be advised. The DCDM 430 may initiate the development of a personalized intervention strategy which may encourage behavioral modifications, physical conditioning, nutritional changes, and treatments (medical and non-medical) that offer the subscriber an array of health options that prioritizes and targets a particular condition while filly considering a host of other subscriber unique factors.

The DASM 490 may be capable of acquiring and analyzing subscriber data pertaining to their usage of prescription drugs, non-prescription drugs, vitamin supplements, herbal remedies and mineral supplements. This data may be given a high priority and may be acquired during the initial data acquisition interactions of the health maintenance system 100 (i.e. data interaction using the PDAU 200). The data may be maintained current through a regular updating process that involves systematic proactive and reactive queries. The focus of these activities may be to identify potential risks and safety issues, educate the subscriber, insure the correct administration of medications and recommend optimized vitamin and mineral usage that may be based on current nutritional and scientific knowledge. Such recommendation may be in the form of drug and supplement programs, services and products.

Figure 14:
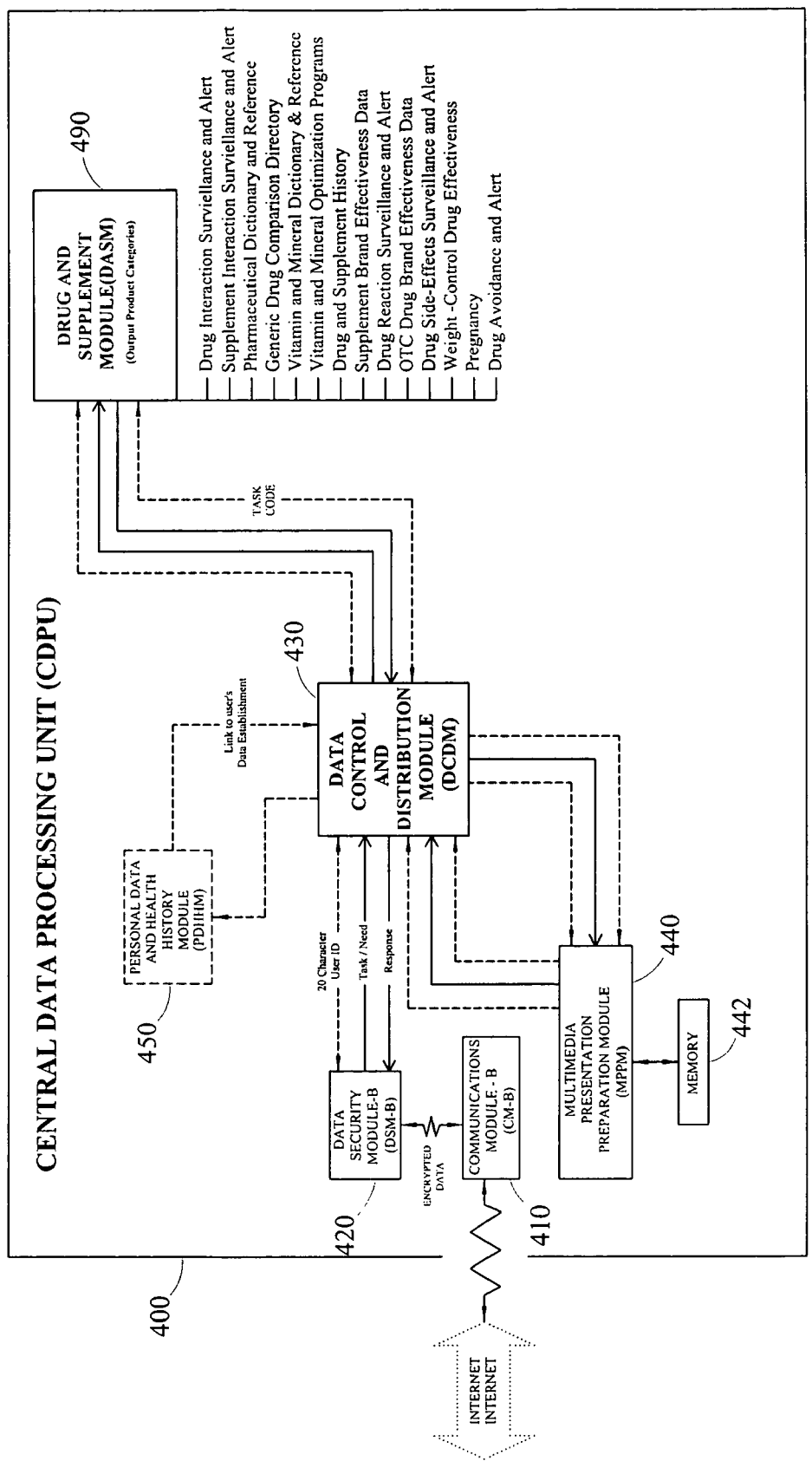
FIG. 14 is a block diagram illustrating drug and supplement output products of a drug and supplement module 490 of the central data processing unit 400, according to an exemplary embodiment of the present invention.

As shown in FIG. 14, the DASM 490 provides output product categories that address: drug interaction surveillance and alerts; supplement interaction surveillance and alerts; pharmaceutical dictionary and references; generic drug comparison directory, vitamin and mineral dictionary and references; vitamin and mineral optimization programs; drug and supplement history, supplement brand effectiveness data; drug reaction surveillance alerts; over the counter (OTC) drug brand effectiveness data; drug side effects surveillance alerts; weight-control drug effectiveness; drug avoidance during pregnancy, drug avoidance and alerts; and the like. In regard to drugs (i.e. prescription and nonprescription), the DASM 490 may offer drug interaction, reaction and side-effects surveillance and alert services (i.e. subscriber drug usage may be monitored in order to detect adverse and/or undesirable effects), drug cost and effectiveness comparisons and drug options, drug effects on other conditions (i.e. other subscriber conditions such as pregnancy, desire to conceive, nursing, allergies, and the like are assessed to determine whether the drug represents a danger or risk), drug affects on occupational performance (i.e. assess drug affects to determine whether a drug or combination of drugs represents a danger of degraded performance or a safety risk), drug administration surveillance and assessment (i.e. monitoring of drug's usage, including quantity and frequency, in order to assess whether the drug is properly being administered), and the like. In regard to vitamin and mineral supplement usage, the DASM 490 may monitor and assesses the subscriber's unique health conditions, nutritional needs, behaviors, and physical/physiological and psychological characteristics in order to establish the most effective vitamin/mineral supplement regime for a particular subscriber. It may also access current and historical supplement usage in order to identify particular patterns and trend indicating supplement administration issues (i.e. dosage, frequency taken, timing, and the like), imbalances, deficiencies, over usage, adverse reactions, side-effects, and the like. The DASM 490 may also monitor the subscriber's health to determine whether usage of a particular vitamin and/or mineral represents a risk to their health or complicates a condition or treatment. The DASM 490 may also reference authoritative standards/laboratory tests/scientific evaluations to assess the quality, purity, and rate of absorption of particular brands and types of supplements in order to ensure only the highest quality products are used and to alert subscribers to inferior and possible dangerous products. The DASM 490 may also be used to assess the interactions between drugs (prescription and nonprescription) and supplements to determine whether there is a risk of adverse interactions and side-effects. Whenever a health risk or possible complication is detected, the DASM 490 may issue an advisory or alert in order to notify the subscriber of the risks.

Also, the DASM 490 may provide various drug and supplement information to other modules of the health maintenance system 100 as supplemental data Such supplemental data may be used to develop products, such as, special diets, physical fitness programs, pregnancy management programs, chronic condition management programs, and the like.

The DLM 510 may be the information, resource and knowledge center of the health maintenance system 100. The DLM 510 comprises a highly integrated set of specially customized database modules which contain a wide assortment of reference materials that address a broad array of health subjects. At least one module of the CDPU 400 may be programmed with the capability of querying the DLM 510. Such modules construct their queries around standardized search-friendly formats. Each query may be assigned at least one search category which reflects core subject areas. Exemplary categories include, but are not limited to, organ system functions and abnormalities, characteristics of aging and longevity, diet and nutrition, cosmetics and cosmetic restoration, physical fitness, emergency first-aid intervention, drugs and supplements, medical and dental dictionary/encyclopedia, and childhood growth and development.

The database modules of DLM 510 may be hierarchically structured i.e., horizontally and vertically integrated. The horizontal integration permits queries to cross over to other categories at different tiers of investigation. A module of the CDPU 400, through which the query may be initiated, may be responsible for collaborating with other supporting modules to ensure that appropriate descriptive or supporting data may be provided to the DLM 510. This supporting data may consist of a subscriber descriptive data (i.e. gender, age, race, height, weight, physical features, body dimensions, physical fitness, etc.), health history data (i.e. physiological characteristics, psychological characteristics, physical deformities, libido, appetite, sleep patterns, allergies, chronic conditions, mental acuity, disabilities, pregnancy status, and the like), medical conditions and treatments (i.e. diagnosed condition, prescription drug usage, medical therapies, procedures, and the like), and non-prescription drug and supplement usage.

The database modules of DLM 510 may be initially constructed by the DMAU-CC 800 which may extract information from the group consisting of scientific research, dictionaries, encyclopedias, reports, case studies, medical studies, and other reference data pertaining to: anthropology, dermatology, cardiology, endocrinology, gastroenterology, gerontology, genealogy, gynecology, kinesiology, neurology, obstetrics, orthopedics, pharmacology, pathology, pediatrics, reproductively, fertility, otolaryngology optometry, ophthalmology, psychiatric, psychology, toxicology, radiation, epidemiology, dentistry, entomology, bacteriology, linguistics, and the like; census data, population health patterns and trends; weight management and diets; nutrition and eating patterns; vitamin and mineral supplements including application, dosage, toxicology, interactions, reactions and complications; human physical, psychological, psychological and behavioral maturation and development; demographic data; injury occurrences and recovery statistics; disease rate of recovery statistics; gender, age, race, ethnicity and geographical specific medical, dental and health risks; emergency medical and dental intervention and treatments; data pertaining to the detection and treatment of conditions caused by nuclear, biological and chemical exposure; occupational health and safety reference data; census data on aging and longevity, data pertaining to nutrition and diets associated with longevity, cosmetics reference data; cosmetic rejuvenation procedures and treatments reference data; environmental hazards detection reference data; data pertaining to the toxicity and hazards associated with commonly used substances; environmental exposure to heavy metals and other poisons; authoritative standards pertaining to normal and abnormal physical, psychological, physiological, and behavioral characteristics; reference data pertaining to the physical, psychological, physiological and behavioral characteristics of particular population groups; sexual performance reference data; fertility reference data; sleep pattern reference data; healing and recovery; physical fitness assessment reference data; disease detection and diagnosis reference data; microbial infection detection and treatment data; mental disorder reference data; stress management reference data; mental acuity and cognition assessment reference data; substance abuse reference data; and the like.

Once the database modules are developed by the DMAU-CC 800, they are distributed to the DMAUs 600 which translate and tailor the data, as required, and distribute the databases to their respective CDPUs 400. The DLM 510 may be programmed with specially designed search engines that are fully compatible with the database modules and complement the rapid search and correlation processes. Search programs in the DLM 510 locate and compile packets of information that are woven together to form responses.

Figure 15:
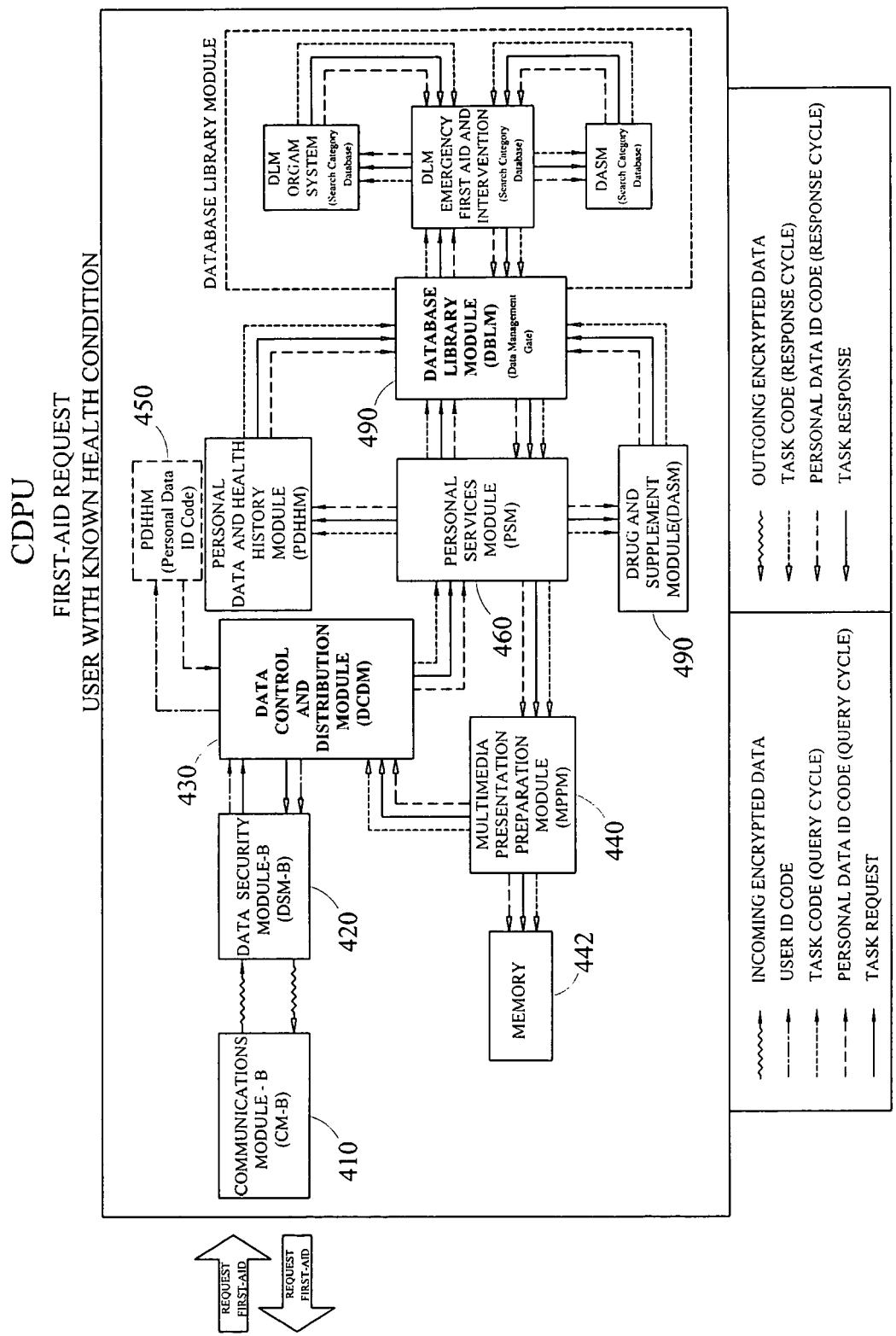
FIG. 15 is a block diagram illustrating a first aid request at the central data processing unit 400, according to an exemplary embodiment of the present invention.

For queries, such as, a request for first-aid assistance, the subscribers have only to address their emergency. The health maintenance system 100 may automatically locate and retrieve certain critical background information (drug allergies, current prescription drug usage, medical conditions, and the like) which may be forwarded to the DLM 510. FIG. 15 illustrates a first aid request at the CDPU 400. The first-aid intervention response generated by the DLM 510 may incorporate first-aid procedures, and procedures to address complications that may be associated with the subscriber's gender, age, race, ethnicity, religion, behavior, psychological/physical/physiological characteristics, medications, pre-existing conditions, and the like.

The MM 520 offers the subscribers an internet store site, more specifically known as a marketplace. The marketplace may be accessed through the PDAU 200, (i.e. through the PDAU-HS 200*a*, or the PDAU-A 200*b* in combination with a subscriber's personal computer), or a subscriber's personal computer installed with a health maintenance system software. The marketplace may offer the subscriber an opportunity to purchase items from a personalized array of health related products. The marketplace may offer personalized products (i.e. includes the offering of products that are likely to be of interest to the subscriber based on their demographics, health condition, medical condition, physical fitness, mental acuity, participation in health programs or activities, and the like). The marketplace may offer financial tracking data to allow the subscribers to monitor their procurements and to track certain spending patterns and trends. Additionally the marketplace monitors certain procurements such as prescription drugs, nonprescription drugs, vitamin supplements, mineral supplements, and the like. In those cases where one or more of these substances, being ordered, are know to cause a reaction or complication, the marketplace may alert the subscriber. In those cases where monitoring indicates reordering is appropriate, the marketplace may issue a reminder. In those cases where subscriber reorders indicate excessive use of a drug, the marketplace may issue a notification.

The MM 520 may interact with PTADM 480, DASM 490, PSM 460, and PDHHM 450 to identify particular products that may be most suited to the psychological, physical, physiological, and behavior characteristics of the subscriber as well as the geographical region they reside in.

The DMAU-CC 800 may be responsible for overall command and control of the DMAUs 600 and, consequentially, the performance and effectiveness of the health maintenance system 100. More specifically, the DMAU-CC 800 may continuously monitor the operational performance, availability, and effectiveness of each subordinate DMAU 600 and their respective CDPUs 400 and PDAUs 200. The DMAU-CC 800 may incorporate teams of specialized researchers that continuously review and update the database library reference materials and product solutions. Furthermore, the DMAU-CC 800 maybe responsible for assessing the cumulative subscriber health history information that is being compiled in a master health history archive* of the DMAU-CC 800.

Figure 16:
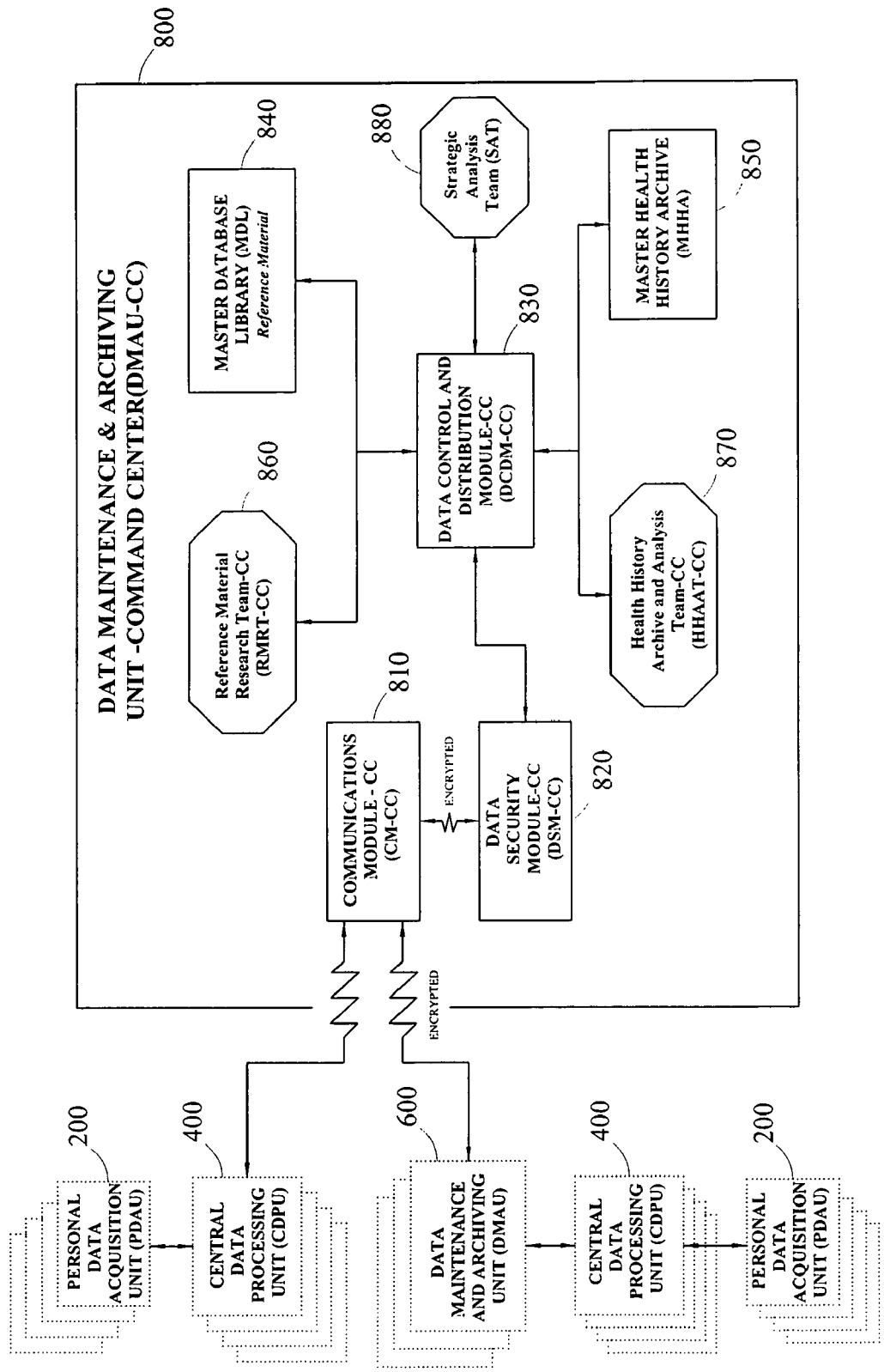
FIG. 16 is a block diagram of a data maintenance and archiving unit-command center 800, according to an exemplary embodiment of the present invention.

Referring to FIG. 16, in one embodiment, the DAMU-CC 800 comprises: five modules; two operational teams; and a strategy team. The modules include the following: a communication module-command center (CM-CC) 810; a data security module-command center (DSM-CC) 820 coupled to the CM-CC 810; a data control and distribution module-command center (DCDM-CC) 830 coupled to the DSM-CC; a master database library (MDL) 840 coupled to the DCDM-CC 830; and a master health history archive (MHHA) 850 coupled to the DCDM-CC 830. The operation teams include the following: a reference material research team coupled to the DCDM-CC 830 and the MDL 840, the reference material research team referred to as reference material research-CC (RMRT-CC) 860; and a health history archive and analysis team coupled to the DCDM-CC 830 and the MHHA 850, the health history archive and analysis team referred to as health history archive and analysis team-CC (HHAAT-CC) 870. The strategy team may be more specifically known as the strategic analysis team (SAT) 880.

The CM-CC 810 supports general internet, intranet and other communication modes as well as enterprise-to-enterprise communications between the DMAU-CC 800 and the DMAU 600. The DMAU-CC 800 may include certain DMAU functions. This means the DMAU-CC 800 may communicate with its subordinate DMAUs 600, as well as its own regional CDPUs 400. The enterprise-to-enterprise communications may be subjected to sender verification and specialized filtration parameters since sensitive data may be transmitted and the enterprise-to-enterprise channel may have greater access to certain core electronic files of DMAU 600 and DMAU-CC 800. The DMAU-CC 800 does not directly communicate with the subscribers. Any communion to or from system entities, other than the health maintenance system 100, may be routed through a separate channel that may be isolated from sensitive internal databases. The CM-CC 810 receives encrypted incoming data (See FIG. 16), establishes data origin, assigns the communication channel, and routes the data to the DSM-CC 820 for decrypting. Outgoing data may be routed to the DSM-CC 820 for encryption and then forwarded to the CM-CC 810 which verifies data completeness and destination. The data may be then transmitted to the designated CDPU 400 or DMAU 600. Also, the CM-CC 810 may be responsible for monitoring the internet/intranet or other modes connectivity to verify operational status and transmission quality.

The DSM-CC 820 maybe capable of performing a plurality of data security and privacy related functions including, but not limited to, decrypting and encrypting data, encoding and decoding subscriber identities, and compressing and decompressing data. The DSM-CC 820 may be specifically tuned to filter communications received from and transmitted to the subordinate DMAUs 600 and CDPUs 400. In this way, firewalls and anti-virus programs may be optimized. Non-sensitive e-mails may be transmitted via a separate channel and may be insulated from MDL 840, MHHA 850, and any other database library and health history archive.

The DCDM-CC 830 may be capable of registering (logging), dating, prioritizing, distributing, and tracking incoming and outgoing messages. A copy of incoming transmissions may be saved and 'response requirements' may be registered. When a sender designates 'REPLY REQUIRED BY (DATE)', the DCDM-CC 830 tracks the progression of the message through the system until a reply may have been registered If the registry is still open two working days prior to the reply required date, the DCDM-CC 830 may issue a reminder to the recipient. The reminders are recorded and include the elapsed time since received date. If no reply is registered by the due date, the DCDM-CC 830 will issue a 'RESPONSE LATE' notice each working day, until a reply is registered Outgoing replies are checked to verify addresses, prioritization, and response requirements. The reply registry is cleared (closed) and the elapsed time-to-respond is logged. The data may be then routed to the DSM-CC 820 for encrypting and compression, if required. The elapsed time-required-to-respond log may be preserved and periodically published as a way of addressing accountability and establishing skill and resource requirements. Note the internal data distribution is handled in a similar way. However, a 'TASK COMPLETED CONFORMATION REQUESTED' and 'TASK COMPLETED (DATE)' are added as options to the data send and reply process.

Also, the DCDM-CC 830 functions as an e-mail monitor. The number of e-mails received and sent by each staff person may be logged. Once a certain volume of e-mail is reached, the DCDM-CC 830 may trigger a prioritization mode which permits only high Priority and a limited number of previously cleared e-mails to be sent through. Furthermore, the DCDM-CC 830 may impose an e-mail respite for three consecutive hours each day. During the respite period, only emergency e-mail priority messages are sent through to staff and only emergency priority outgoing messages and/or high-priority overdue or late-responses are permitted to be sent out.

The MDL 840 contains the latest configuration of the health maintenance system 100, reference materials, studies, research, source data, strategies, regimes, and other products. In one embodiment, the data in MDL 840 may be organized into the following horizontally and vertically integrated database categories: organ system functions and abnormalities (including both normal and abnormal characteristics delineated by age, gender, race, ethnicity, geographical location, and the like); characteristics of aging and longevity (including both normal and abnormal aging characteristics specific to gender, race, ethnicity, geographical location, and the like); diet and nutrition (including diet and nutritional requirements and preferences specific to physical conditions, mental conditions, behaviors, age, gender, race, ethnicity, geographical location, occupation, and the like); cosmetics and cosmetic rejuvenation and restoration (includes the identification of normal and abnormal skin conditions and the non-invasive and invasive procedures, processes, and cosmetics, that are best suited for an individual based on their skin condition, age, gender, race, ethnicity, physical condition, medical condition, geographical location, and the like); physical fitness (includes normal and abnormal physical fitness performance as well as specific exercise techniques and regimens best suited to an individual based on their physique, health, age, gender, race, ethnicity, geographical location, and the like); emergency first-aid intervention, drugs and supplements; medical and dental dictionary/encyclopedia; childhood growth and development; demographic characteristics; and the like.

Each category is collaboratively linked to other related categories in order to identify the most suitable compilation of health strategies, regimens, procedures, and services that are tailored to age, gender and race as well as various combinations of health conditions, ethnicity, geographic location, and the like. The MDL 840 data may be subject to a continuous review process by the RMRT-CC 860 which may have content and configuration management authority for MDL 840. The subordinate DMAUs 600 are supplied the updated revisions of the MDL 840 and are responsible for translating and tailoring the data for use in their specific geographical territories.

Each CDPU 400 submits their subscribers' health histories and corresponding updates to their respective DMAUs 600, from which a copy is then forwarded to the DMAU-CC 800. The DMAU-CC 800 routs the health histories to the MHHA 850 there it is compiled and permanently stored. Copies of the individual health histories are made available for retrieval by the HHAAT-CC 870 and provided to subscriber or an authorized representative. Exemplary databases include, but are not limited to: personal identification characteristics database, physical characteristics database, physiological characteristics database, behavioral characteristics database, family health history database, subscriber health history database, disabilities and deformities database, illness and injuries database, chronic conditions database, medical condition and treatment history database, historical relative condition database, and the like. This data may be permanently retained in the MHHA 850 even though a subscriber may be inactive or deceased. Also, the HHAAT-CC 870 may be tasked with retrieving copies of certain subscriber health history information, for distribution to the subscriber or authorized subscriber designee, upon request.

The RMRT-CC 860 comprises a group of researchers and analysts that have specialties in at least one subject category addressed by the MDL 840. The RMRT-CC 860 researches and develops new or updated reference materials, products and process change recommendations for MDL 840. These recommendations may initially be subjected to review of a configuration control board (CCB) and, if approved, incorporated into the databases of MDL 840.

The RMRT-CC 860 may be assigned the following areas of responsibility: CDPU 400 and DMAU 600 products/service processes improvement, updates, change recommendations; source data screening; research and development; and HHAAT-CC 870 product and process improvements and change recommendations.

The RMRT-CC 860 processes and evaluates incoming CDPU 400 and DMAU 600 change recommendations. The CDPUs 400 and subordinate DMAUs 600 are chartered with the responsibility of documenting observed issues, such as, errors, discrepancies, unnecessary complications, inconsistencies, content deficiencies, and performance deficiencies. These issues are submitted to the RMRT-CC 860 for review and action. The RMRT-CC 860 may be responsible for reviewing each issue and determining whether changes in the database of MDL 840 are necessary. When a decision to proceed is made, the RMRT-CC 860 develops the updates, new content, processes, and other changes which are then submitted to the CCB for review and approval.

In source data screening, the RMRT-CC 860 may be responsible for the continuous compiling, screening, and assessing outside knowledge sources and source data to identify new and updated information that may be consistent with the objectives of the health maintenance system 100 and would benefit a subscriber of the health maintenance system 100. When new health information or insights become available, the RMRT-CC 860 adapts the data for incorporation into the reference material/database of MDL 840. This new or updated material is then submitted to the CCB for review and approval.

In research and development, the RMRT-CC 860 may be responsible for identifying research and development candidates that would improve the capabilities, effectiveness, efficiency and performance of MDL 840 and, more generally, the capabilities of the health maintenance system 100. The research and development recommendations may be subjected to a review and authorization process which may be responsible for selecting the most appropriate research and development candidates for implementation. When authorized to proceed, the RMRT-CC 860 may be tasked with implementing the research and development activities.

The HHAAT-CC 870 may have two areas of responsibility. First, the HHAAT-CC 870 may be responsible for monitoring and identifying certain shifts or changes in subscriber demographics or changes in health environments, health conditions, health behaviors, and the like. The monitoring process is both general in application as well as age, gender, race, ethnicity, geographic, and occupation oriented. The second area of responsibility includes evaluating a product's/service's effectiveness and identifying deficiencies. Once subscriber health or behavioral shifts have been detected or when product/service performance issues have been identified, they are routed to the RMRT-CC 860 for review and action. When certain particular subscriber health changes have been detected, suggesting a potentially hazardous level of exposure to contaminants or certain nuclear, biological or chemical substances, the HHAAT-CC 870 can issue an alert to appropriate health authorities.

The HHAAT-CC 870 may be responsible for authenticating requests to retrieve subscriber health history data and for initiating the retrieval process. The data retrieval authentication process may be divided into the following elements: subscriber data request; and third party authorized data requests. In the subscriber data request, active subscribers may request copies of their health history archive at any time. These requests are processed by the HHAAT-CC 870 which may verify the requestor's identity when the automated process is unable to do so. Once the requester's identity has been verified, the MHHA 850 is prompted to retrieve the data and supply it to the requestor. Inactive subscribers (i.e. inactive because they have discontinued the services of health maintenance system 100) may still receive their previously archived data on appropriate authentication of identity. In third party data requests, a subscriber can formally authorize the release of all or part of their data to a third-party, such as a medical institution, physician, emergency care facility, living blood relative, future descendent, and the like. Concurrently, the HHAAT-CC 870 will not release subscriber data to unauthorized entities unless legally ordered to do so by appropriate authorities. The HHAAT-CC 870 may facilitate the rapid set-up of the third-party data retrieval request authorization in cases of medical emergency. The health maintenance system 100, MHHA 850 can also function as a central depository for vast amounts of highly organized health history data. This data can be extremely important to a physician in an emergency situation. Therefore, the HHAAT-CC 870 and the MHHA 850 are designed to automatically accommodate emergency requests and provide rapid electronic responses seven days a week, twenty-four hours a day.

The analysis responsibilities of HHAAT-CC 870 include subjecting the data available in the MHHA 850 to various screening and analysis processes, including, but not limited to the following processes: patterns and trends analysis, comparative analysis, and product effectiveness analysis. In the patterns and trends analysis of MHHA 850 data, the HHAAT-CC 870 continuously monitors subscriber health history data to establish or update the aggregate subscriber patterns. As used herein, 'subscriber patterns' refer to the predictable ranges of the subscriber's health characteristics as recorded over time. As new subscriber data may be submitted and the accumulation of data grows, patterns become more established and predictable. However, under certain circumstances, fundamental changes may occur (for example, demographic, environmental, health conditions, health behaviors, and the like), in at least one geographical territory of DMAU 600, that cause patterns to permanently shift and gradually form new patterns. These change processes are referred to as trends. The HHAAT-CC 870 maybe sensitized to detect early signs of trends (or shifts). These trends may reflect significant situations that could be spreading and could have an impact on the health of the region. Early detection of trends also permits a rapid response on the part of the health maintenance system 100. Once trends are detected, the HHAAT-CC 870 designates the trend 'targeted' for immediate action and/or additional surveillance and research which results in the submission of trend reports to the RMRT-CC 860 for action. The designation 'targeted' are given high priority status, such that which can require it to be worked as soon as practicable.

In product effectiveness analysis, the HHAAT-CC 870 may be responsible for reviewing the product success rates based on subscriber data maintained in the MHHA 850. As used herein, 'products' refer to programs and services that are customized to meet specific subscriber needs. Such products comprise both standardized and personalized elements. The standardized elements comprise processes, procedures, practices, regimens, and strategies that are generally known to be effective and are based on fundamentally sound principles, authoritative standards, statistical evidence, scientific knowledge, and solid empirical observations. The personalized elements take into consideration the subscriber's mental acuity plus their psychological, behavioral, physical, and physiological characteristics, as well as gender, age, race, ethnicity, geographical location, and the like. When the standardized elements are sensitized to the personalized elements, they produce an optimized product that may specifically tailored to the unique characteristics of a specific person. In addition, the HHAAT-CC 870 screens the MHHA 850 data for indications that previously recommended products are proving to be less effective than expected. This condition may be termed as 'Failed to Meet Objective' (FMO). Once a statistically significant group of FMOs have been associated with a particular product, the product may be 'targeted' for additional research to determine whether it should be modified or deleted.

The SAT 880 may be responsible for collecting, integrating, interpreting, and analyzing information with the objective of evaluating the operational status, performance, and effectiveness of the health maintenance system 100 in order to identify new or underdeveloped opportunities to deliver more effective and comprehensive products and services. More specifically, the SAT 880 develops concepts, constructs strategies, planning documents, and proposals (including performance objectives, budgets, and schedules) for future system improvements, technology upgrades, software applications, business opportunities, and the like. The data categories available to SAT 880, including, but not limited to, objective effectiveness data categories, and system effectiveness data categories.

Information derived from the objective effectiveness data categories enables the SAT 880 to monitor and assess the cumulative success rate and failure rate, of programs and services, in meeting their predetermined objectives. Measuring the success or failure in reaching an objective may be useful in evaluating what works and what doesn't work To measure a product's/service's success in meeting objectives, the SAT 880 may acquire data from the MDL 840 and the MHHA 850. The MHHA 850 is populated with details pertaining to the application and administration of products and services offered by the CDPUs 400, which initially receive their source data, reference data, processes, and procedures from the DMAU-CC 800 through their respective DMAUs 600. The CDPUs 400 systematically assigns each an objective which, in turn, is divided into sequential elements that are quantifiable and significant in their own right. These elements can be referred to as steps or phases. Along with monitoring the objectives, the CDPU 400 monitors and responds to each of the objective's steps. The monitoring part consists of determining whether the step has been successfully completed The response part may be triggered when the subscriber fails to successfully complete a step. Responses include an assessment of the situation and recalibration of the CDPU 400 program responsible for developing the current solution. Once recalibrated, the program establishes a modified "path-forward" which can include changes to the current step and subsequent steps, as well as schedule adjustments. Periodically, the CDPU 400 submits an objective success rate summary and log of the program and service successes and failures to their respective DMAU 600. The DMAU 600 automatically monitors these inputs and compare the results to other CDPU 400 inputs in order to determine whether the failures are anomalies or systemic. The objective success rate summary log may be then amended to reflect the DMAU 600 findings and transmitted to the DMAU-CCs 800 and finally to the SAT 880. The SAT 880 compiles the DMAUs 600 input data and analyzes the cumulative data to identify which programs and services tend to succeed or fail, as well as what steps are most likely to require CDPU 400 intervention. This permits the SAT 880 to correlate successes and failures to subscriber characteristics.

Information derived from the system effectiveness data categories enable the SAT 880 to monitor the cumulative operational effectiveness of the health maintenance system 100. The major components of the health maintenance system 100 (includes the PDAU 200, CDPU 400, DMAU 600, and DMAU-CC 800) may be assigned specific quantifiable operational and performance objectives. These operational and performance objectives address the component's operational capabilities, status and the level of performance at the component level and the subsystem or module level. Each component monitors its operational capabilities and maintains a status of the availability of these capabilities. Certain components also monitor the system's level of operational performance to determine whether the operational performance objective is being met. The monitored data may be recorded in the operation objective summary log of their respective components and transmitted to the next higher system tier. The next higher tier compiles the data and compares it to other inputs to determine whether any of the detected failures-to-meet-operational-objectives are anomalies or systemic. The logs are then modified to reflect the findings and transmitted to the next higher component. This process may be repeated until the operational objective summary logs are transmitted to the SAT 880. The SAT 880 program compiles the operational objective summary log inputs and analyzes the cumulative data to identify which component and components subsystems tend to succeed or fail, and, at what rate. Influencing factors, causes and recovery time are incorporated into the operational objective summary log. Influencing factors/ causes may include operator error, equipment failure, environmental effects or acts of nature (e.g. weather, fire, floods, earthquake, etc.), illegal or inappropriate activities (e.g. theft, vandalism, sabotage, unauthorized modifications, etc.), and accidents or mistakes. Recovery time, meaning the speed at which the system may be restored to operational condition, is considered as an important measurement and may be tracked and recorded regardless of the cause of a failure.

The DMAUs 600 receives the updated reference materials, programs, and service data from the DMAU-CC 800, which is then translated (when required), tailored, and distributed to respective CDPUs 400. Also, the DMAU 600 may receive requests for copies of subscriber health history archive data. These requests may be initiated at the PDAUs 200 level and transmitted, through the CDPUs 400, to the DMAUs 600.

Figure 17:
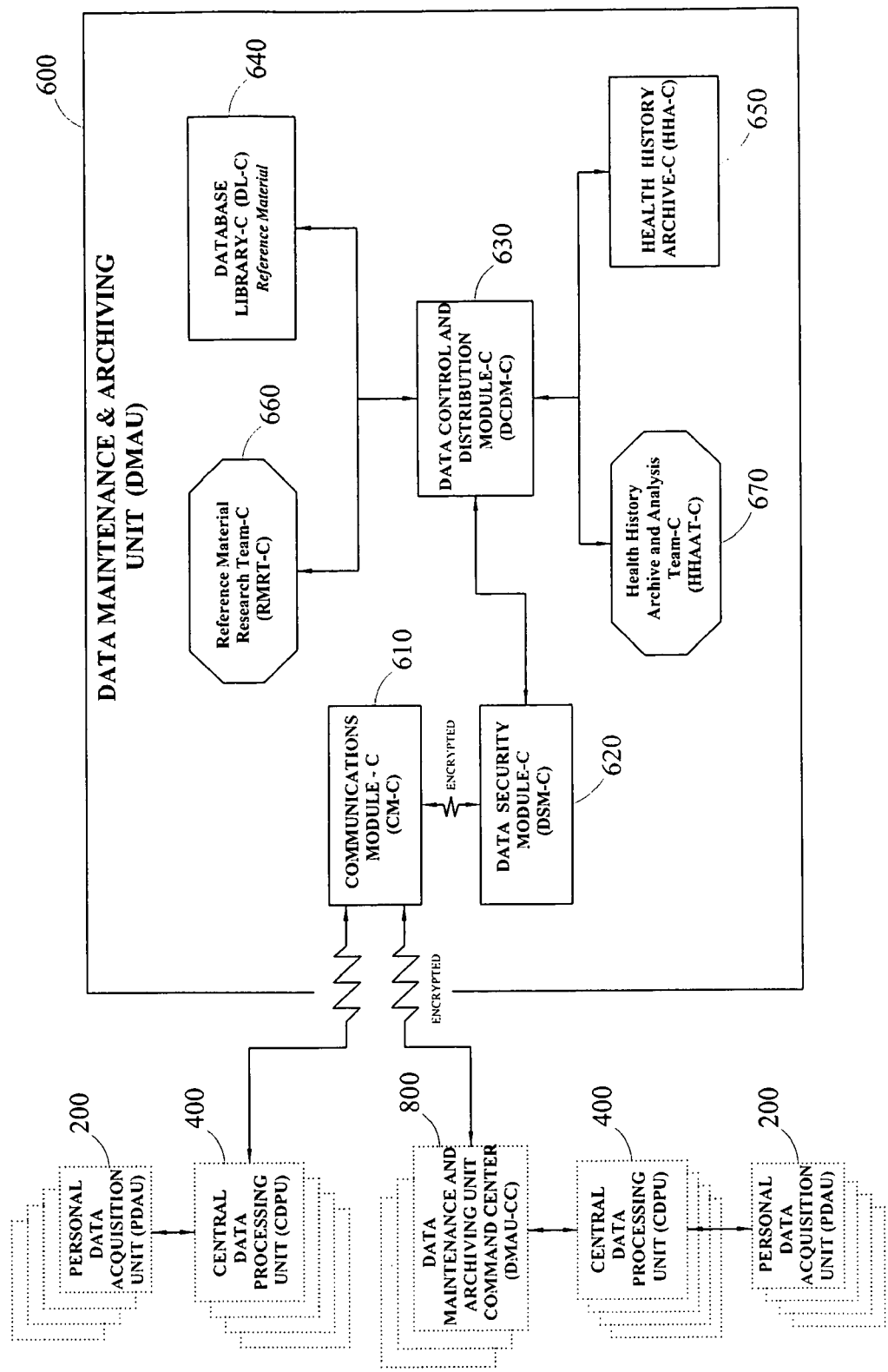
FIG. 17 is a block diagram of a data maintenance and archiving unit 600, according to an exemplary embodiment of the present invention.

Referring to FIG. 17, in one embodiment, the DAMU 600 comprises: five modules; and two operational teams. The modules include the following: a communication module-C (CM-C) 610; a data security module-C (DSM-C) 620 coupled to CM-C 610; a data control and distribution module (DCDM-C) 630 coupled to the DSM-C 620; a database library-C (DL-C) 640 coupled to the DCDM-C 630; and a health history archive-C (HHA-C) 650 coupled to the DCDM-C 630. The operational teams include the following: a reference material research team-C (RMRT-C) 660 coupled to the DCDM-C 630 and the DL-C 640; and a health history archive and analysis team-C (HHAAT-C) 670 coupled to the DCDM-C 630 and the HHA-C 650.

The CM-C 610 supports general communications (internet, intranet, telephone, satellite telephone, radio, and the like) and enterprise-to-enterprise communications between the DMAUs 600 and their CDPUs 400 and between the DMAUs 600 and the DMAU-CC 800. The enterprise-to-enterprise communications are subjected to sender verification and specialized filtration parameters since certain core databases may be transmitted and the enterprise-to-enterprise channel may have greater access to certain internal documentation of the DMAUs 600. The DMAUs 600 do not directly communicate with the subscribers but rather they communicate with respective CDPUs 400 and the DMAU-CC 800. The CM-C 610 receives encrypted incoming data, establishes data origin, assigns the communication channel, and routes the data to the DSM-C 620 for decrypting. Outgoing data may be routed to the DSM-C 620 for encryption and then forwarded to the CM-C 610, which verifies data completeness and destination. The outgoing data may be then transmitted to the designated CDPU 400 or DMAU-CC 800. Also, the CM-C 610 may be responsible for monitoring the communication modes connectivity and to verify operational status and transmission quality.

The DSM-C 620 may be capable of performing a plurality of data security and privacy related functions including, but not limited to, decrypting and encrypting data, encoding and decoding subscriber identities, and compressing and decompressing data. More specifically, the DSM-C 620 may be tuned to communicate between the DMAU 600 and its network of CDPUs 400 as well as between the DMAU 600 and the DMAU-CC 800. In this way firewalls, anti-virus programs, filters and the like may be optimized. Non-sensitive communications, including certain e-mails, are transmitted via a secure but separate channel and are insulated from any DL-C 640 and HHA-C 650.

The DCDM-C 630 maybe capable of registering (logging), dating, prioritizing, distributing, and tracking incoming and outgoing messages. Note that logging the sender, receiver, and the date and time the message is received and opened may be part of this process. A copy of incoming transmissions may be saved and 'response requirements' may be registered. When a sender designates 'REPLY REQUIRED BY (DATE)', the DCDM-C 630 tracks the progression message through the system until a reply may have been registered. If the registry is still open two working days prior to the reply-required-by-date, the DCDM-C 630 will issue a reminder to the recipient. The reminders are recorded and include the elapsed time since the time and date the message was received If no reply is registered by the due-date, the DCDM-C will issue a 'RESPONSE LATE' notice each working day, until a reply is registered. Outgoing replies are checked to verify addresses, prioritization, and response requirements. The reply registry may be cleared (recorded as closed) and the elapsed time-to-respond may be logged. The message may be then routed to the DSM-C 630 for encryption and compression, as required. The elapsed time-required-to-respond log may be preserved and periodically published as a way of addressing responsiveness and establishing correspondence skills and defining resource requirements. Note the internal data distribution may be handled in a similar way, however, a 'TASK COMPLETED CONFORMATION REQUESTED' and 'TASK COMPLETED (DATE)' may be added as options to the data-send and data-reply process.

Also, the DCDM-C 630 functions as the e-mail monitor. The number of e-mails received and sent by each staff person may be logged. Once a certain volume of e-mail is reached, the DCDM-C 630 trigger the Prioritization Mode which permits only High Priority and a limited number of previously cleared e-mails to be sent through. The DCDM-C also imposes an e-mail respite for between two and three (3) consecutive hours each day. During the respite period, only emergency e-mail priority messages are sent through to staff and only emergency priority outgoing messages and/or high-priority late-responses are permitted to be sent out.

The DL-C 640 contains the latest configuration of program data, service data and health strategies that may have been supplied by the DMAU-CC 800. In one embodiment, the data in DL-C 640 may be organized into the following databases: organ system functions and abnormalities (including both normal and abnormal characteristics delineated by age, gender, race, ethnicity, geographical location, etc.), characteristics of aging and longevity (including both normal and abnormal aging characteristics specific to gender, race, ethnicity, geographical location, etc.), diet and nutrition (including diet and nutritional requirements and preferences specific to physical conditions, mental conditions, behaviors, age, gender, race, ethnicity, geographical location, occupation, etc.), cosmetics and cosmetic restoration and rejuvenation (includes the identification of normal and abnormal skin conditions and the non-invasive and invasive procedures, processes, and cosmetic products that are best suited for an individual, based on their skin condition, age, gender, race, ethnicity, physical condition, medical condition, geographical location, etc.), physical fitness (includes normal and abnormal physical fitness performance as well as specific exercise techniques and regimens best suited to an individual based on their physique, health, age, gender, race, ethnicity, geographical location, etc.), emergency first-aid intervention, drugs and supplements, medical and dental dictionary/encyclopedia, childhood growth and development, demographic characteristics, and the like.

Each category contains unique reference materials, products, programs, services and strategies. The RMRT-C 660 may be responsible for translating (when required) and tailoring new DL-C 640 data to accommodate the language, social, and cultural peculiarities of their respective geographical territories. The revised data may be then retained in the DL-C 640 and copies transmitted to the CDPUs 400. When tailoring of the data is required, it is done in separate enhancement-modules that maybe easily linked to elements of the original core data in order to facilitate configuration management. Tailoring shall be limited to, among other things, emphasizing certain more acceptable behaviors or practices and deemphasizing others, sensitizing language and content to satisfy particular religious or cultural norms.

Each CDPU 400 submits their subscriber's health histories, and corresponding updates, to their respective DMAUs 600. The DMAU 600 retains active subscriber's data in the HHA-C 650 and transmits the most recent copies of both active and recent inactive subscriber data to the DMAU-CC 800. Once a subscriber is designated inactive, most of their data is removed from the HHA-C 650. However, when required by regional privacy laws, regulations, rules, and political/cultural norms, the DMAUs 600 may retain control over, and make available for retrieval, both active and inactive (including deceased) subscriber health history data. Otherwise, inactive subscriber data is permanently archived and maintained in the DMAU-CC's 800 MHHA 850.

The HHA-C 650 database may consist of the following data categories: personal identification data, physical characteristic data, physiological characteristic data, behavioral data, family health history data, subscriber health history data, subscriber medical history data, medical condition and treatment history data, historical relative condition data, disabilities and deformities data, illness and injuries data, chronic conditions data and the like.

Personal identification data may comprise of those characteristics that clearly distinguish one subscriber from another and establish demographic delineators as well as life style and life experiences. Personal identification data may include the subscriber's vital statistics including name, address, residence history, age, gender, race, ethnicity, education, sexual preference, martial status, living arrangements, marital history, children, occupation, work history, home and work environments, genealogy, relationships, recreational activities and the like. Also, the subscriber's travel history, military service, overseas residency, pets, and other information that may be useful in establishing a history of the subscriber's living arrangements and living environments may be collected under this category. Only the subscriber's coded name and address are identified in the HHA-C 650 database. The names/addresses that correlate to the code may be maintained separately by the DSM-C 620.

Physical characteristics data comprises features, attributes, peculiarities, deformities, body shape, body dimensions, and the like that physically establish the subscriber as a unique entity. Physical characteristics may include height, weight, body fat ratio, body symmetry and dimensions, skin shade, skin texture, eye color, hair growth, hair color, hair texture, strength symmetry, endurance, coordination, posture, gait, nail growth, nail features, feet size, physical peculiarities, physical deformities, growths blemishes, teeth and gum condition, flexibility, and the like.

Psychological characteristics address the subscriber's mental state and processes including emotions and behaviors. The physiological characteristics data address the normal and abnormal performance characteristics of the subscriber's organ systems. These may include data such as vital signs, cardiovascular system, respiratory system, nervous system, skin system, musculoskeletal system, blood system, digestive system, endocrine system, urinary system, reproductive system and combinations comprising at least one of the foregoing for establishing unique characteristics and performance that may include visual acuity, blood pressure, heart rate and rhythm, respiratory rate, blood oxygen level, cholesterol levels, estrogen level, hearing acuity and sensitivity, sensory perception, PSA level, insulin levels, mental clarity, responsiveness, gait, posture, balance, teeth and gum condition, skin abnormalities, inflammation, pain, discomfort, discharges and the like.

Behavioral data depict inherent and learned characteristics, such as, routines (including eating and sleeping routines), habits, personal discipline, patience, attitudes, aggressiveness, competitiveness, and addictions. These may include alcohol usage, tobacco usage, drug usage, gambling, nail biting, restlessness, socialization skills, and the like.

Family health history addresses both living and deceased blood relatives. Family health history provides identity data, psychological characteristics, physical characteristics, physiological characteristics, behaviors, health conditions, medical histories, occupations, marital status, children, educational level, peculiarities, deformities, and the like. More, particularly the family health history data addresses the group of information consisting of race, ethnicity, place of birth, residency history, health history, birth date, marital status/history, gender, height, sexual preferences, weight, body dimensions, reproductive history, vision, hearing, hair growth/texture/color, eye color, blood type, chronic conditions, allergies, disease history (including ages at time of detection), cause of death, age at death, health conditions at time of death, military service history, travel history, injuries, disabilities, occupations, hazardous/toxic materials exposure, medication history, medical treatments and procedures, reproductive histories, and the like.

The subscriber's health history addresses the subscriber's general wellness or well-being. These are recorded chronologically and divided into four general categorizes which include childhood health, adolescent health, adult health, and senior health. These categories address certain specifics such as growth and development, cognition, chronic conditions, activity levels, vital signs, health peculiarities, allergies, appetite, medical conditions, injuries, medical treatments and procedures, childbearing, vitality, robustness (i.e. susceptibility to infection, disease and injury as well as rates of recovery), libido, fertility, age-related degradation, mental acuity, and the like.

The subscriber's medical history includes details pertaining to medically diagnosed conditions which include diseases, infections, injuries, abnormalities, deformities, non-specific chronic ailments, and the like. The details may address the specific diagnosis, age at diagnoses, hospitalization history, medical procedures, treatments, therapies, prescription drug usage, drug allergies, treatment effectiveness, and the like. Also, the medical history may include a detailed chronological record of laboratory tests and diagnostic procedures.

The HHA-C 650 data maybe made available to the HHAAT-C 670 which may support the automated authorization and retrieval of subscriber health histories and the automated distribute certain copies of information to active subscribers and/or authorized third parties (i.e. emergency medical practitioners, personal physician, specialists, and the like). Also, the HHAAT-C 670 is responsible for supporting the automated screening of aggregate data to identify collection or documentation anomalies or irregularities. If these are detected, the HHAAT-C 670 initiates an investigation to determine the cause and make the necessary corrections. The HHA-C 650 corrections are immediately submitted to the DMAU-CC 800 for incorporation into the MHHA 850.

The RMRT-C 660 consists of specialized software programs and a group of researchers and analysts that have regional specialties in at least one of the categories addressed by the DL-C 640. The RMRT-C 660 may be assigned the following areas of responsibility: translation; tailoring, monitoring, and CDPU 400 change recommendations.

The DMAU-CC 800 periodically transmits updated copies of the master database library to the DMAUs 600. These materials may typically be developed in American English and it may be the responsibility of RMRT-C 660 to translate them into the language or dialect commonly used in the regions serviced by the respective CDPUs 400. Care is taken to make literal translations and not to change the meanings or inferences built into the original data.

Tailoring, of the translated data, may be necessary when the territory being served may have social or religious customs, doctrines, or belief-systems that conflict or are incompatible with materials in the MDL 840. The tailoring may also be applied to modify language usage in order to optimize subscriber comprehension. For example, it may be appropriate to tailor (change) certain wording and/or syntax when it is evident that the original way the material was presented may have consistently caused misunderstandings or confusion Tailoring may be stringently controlled to retain continuity with the original intent. Any modification to the original material may be done through separate enhancement modules which link back to, but do not alter, the original material. These translated materials and enhancement modules are maintained in the HHA-C 650.

In the monitoring process, the RMRT-C 660 monitors, assesses and then optimizes the operational performance and availability of their respective CDPUs. Regular status reports are submitted to the DMAU-CC 800 which analyzes the data in relationship to the aggregate of DMAUs 600 inputs. Hardware, software and process changes, resulting from the analysis, are supplied to the RMRT-C 660, which then implements the changes.

The CDPUs 400 perform automated monitoring and assessments of their own sub-systems and their respective PDAUs 200. Based on the conclusions derived from these assessments, the CDPUs 400 submit recommendations for change to their respective DMAUs 600 which may include modifications and updates that enhance or expand performance, effectiveness, and/or reliability of the reference data, hardware, software, processes, programs, and services related to or resident in the DLM 510. The RMRT-C 660 processes these inputs and implements those changes that are considered to be appropriate. Change recommendations requiring global or more comprehensive changes are forwarded to the DMAU-CC 800 for evaluation.

The HHAAT-C 670 may be responsible for acquiring subscriber health history data from their respective CDPUs. The incoming health history data files are screened to verify format compliance, completeness (i.e. incorporation of necessary identification characteristics and key data elements), and population trends/peculiarities. The subscriber health histories may then be stored in the HHA-C 650 and a copy of the data may be transmitted to the DMAU-CC 800 for further evaluation and permanent archiving. A subscriber or subscriber's authorized designee may request copies of their health history data through their respective CDPUs 400. When such a request is received, the HHAAT-C 670 program which may verify the status of the requester (i.e. active subscriber, inactive subscriber, subscriber designee) and may process the request in one of two ways. First, when a requester is determined to be an active subscriber and subscriber's identity has been authenticated, the HHAAT-C 670 program will process their request by retrieving and distributing the health history data. Second, when the requester is determined to be an inactive subscriber or a subscriber designee (i.e. some person or organization to whom the subscriber wishes to provide their data), the HHAAT-C 670 may process the request and transmit the request to the DMAU 600 for evaluation, authentication and action. The request may be logged by the DCDM-C 630 and the HHAAT-C 670 assigned the responsibility of processing the request which includes authenticating the identification of inactive subscribers, reviewing designee authorizations and authenticating the subscriber designee's identity, and performs certain retrieval pattern and trend assessments in order to determine whether any unusual or peculiar patterns or trends are depicted.

The analysis responsibilities of HHAAT-C 670 include subjecting the aggregate subscriber health histories, resident in the HHA-C 650, to various screening and analytical processes including, but not limited to patterns and trends analysis and product effectiveness analysis. In the patterns and trends analysis, the HHAAT-C 670 continuously screens the HHA-C 650 data to establish and update the aggregate health patterns that depicts certain unusual, peculiar and/or abnormal characteristics that apply to a group of subscribers, within a particular CDPU 400, or to a group of CDPUs 400. As new subscriber data is submitted and the accumulation of health history data grows, patterns become more established and predictable and deviations from these patterns or spikes are more easily detected. Early detection of certain deviations may be very useful in the detection of unusual health characteristics occurring in small subscriber groups. This quick detection and precise location of the affected population is particularly useful in identifying exposures to hazardous nuclear, biological and chemical substances that may otherwise go undetected. Under certain circumstances, fundamental changes may occur (i.e. demographic changes such as a growth or decrease in the number of older people per capita, environmental changes such as the reduction or increase in pollutants emitted by nearby industrial facilities, health conditions such as an improvement or degradation of prenatal care and childhood disease inoculation programs, health behaviors such as a notable reduction in smoking, and the like) that cause patterns to permanently shift and gradually form new patterns. These change processes are referred to as trends. The HHAAT-C 670 may be sensitized to detect early signs of trends (or shifts) since they can reflect significant changes that could be spreading and could have an impact on the health of the region. Early detection of spikes or deviations in normal health patterns, or more preeminent health shifts or trends may facilitate a rapid response on the part of the health maintenance system 100. Once spikes or deviations are detected, the HHAAT-C 670 designates the peculiarity 'targeted' for additional verification, refinement and RMRT-C 660 rapid response.

In product effectiveness analysis, the HHAAT-C 670 may be responsible for reviewing the DL-C 640 product's success rates, based on the evidence of effectiveness derived from the HHA-C 650. As used herein, 'products' refer to programs, services and health strategies that are customized to meet specific subscriber needs. Such products comprise both standard and personalized elements. The standardized elements comprise processes, procedures, practices, regimens, or strategies that are generally known to be effective. The personalized elements take into consideration the subscriber's physical and physiological characteristics, gender, age, race, ethnicity, population group, and the like. When the standard and personalized elements are combined, they produce an optimized product that may be tailored to the characteristics of a specific person. The HHAAT-C 670 screens the health histories, found in the HHA-C 650, for indications that recommended products are proving to be less effective than expected. This condition may be termed as 'Failed to Meet Objective' (FMO). Once a statistically significant group of FMOs have been associated with a particular product, the product may be 'targeted' for additional research, modification, or deletion.

Figure 18:
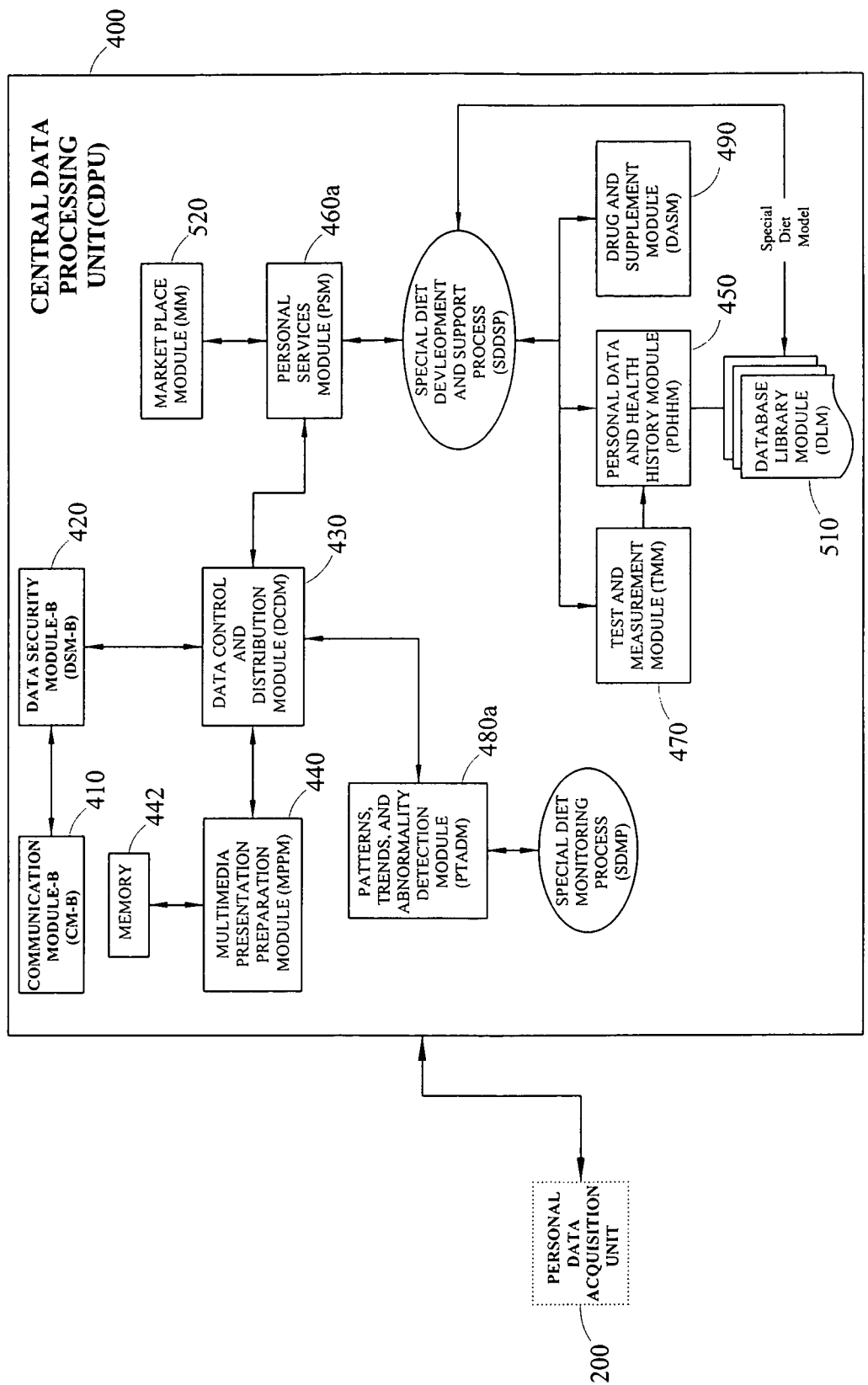
FIG. 18 is a block diagram of a central data processing unit 400 implementing a special diet program.

In one embodiment, the health maintenance system 100 provides a special diet program, incorporating specifically constructed dietary behavior and nutritional enhancement modification strategies that address weight management for general health, aesthetic, and therapeutic purposes. As shown in FIG. 18, the implementation of the special diet program involves CDPU 400 components that may be comprised of a CM-B 410; a DSM-B 420; a DCDM 430; MPPM 440;a PSM 460a—involving a special diet development and support process (SDDSP); a TMM 470; a PDHHM 450; a DASM 490; a DLM 510; a PTADM 480a—involving a special diet monitoring process (SDMP); a MM 520 and memory 442.

The development of a special diet program begins with the initiation of a special diet request, which may be transmitted to the CDPUs 400, through the PDAU 200, or originating in the CDPU 400. In the CDPU 400, the request is routed to the PSM 460a which may be responsible for administering special diet programs in collaboration with the supporting modules: the TMM 470, the PDHHM 450, the DASM 490 and the DLM 510 plus the special diet monitoring support provided by the PTADM 480a. In regard to special diets, the activities of the PSM 460a may be governed by a program known as the special diet development and support process or the SDDSP. The SDDSP acts to initiate and control certain supporting module functions in order to construct a special diet. Once the special diet program's construction is completed, certain basic parameters, established at the time of the special diet initiation, are verified by a program in the PSM 460a and the special diet may be submitted to the MPPM 440 for presentation enhancement. From MPPM 440, the special diet is transmitted to the subscriber's PDAU 200 through the DCDM 430, DSM-B 420 and the CM-B 410.

The SDDSP efforts may be divided into two operational phases. The first phase involves the selection of a suitable special diet model and the second phase involves the customization or personalization of the special diet model. The first phase or selection of a special diet model, takes into consideration the diet's objective or objectives (i.e. loose weight, gain weight, improve stamina, gain muscle, treat a specific nutritional deficiency, enhance the immune system, purge heavy metals from the body, reduce blood pressure, recover from an illness, and the like) plus certain other basic considerations, including, among other things, the subscriber's age, gender, race, ethnicity, geographical location. These considerations are used to identify diet models that are known to be the most effective in achieving the objectives when administered to a population group having the same or similar characteristics as the subscriber. The second phase comprises a two-part customization process. The first part takes into consideration certain subscriber medical/health conditions, blood type, mobility, activity level, allergies, disabilities, psychological characteristics, physical characteristics, physiological characteristics, behaviors, and the like that are known to influence the effectiveness or suitability of a particular dietary strategy. The second phase, of the customization process, includes the incorporation of certain subscriber preferences pertaining to how, what, where, and when food and drink is ingested.

In detail, the first phase of the SDDSP may elaborate on the objective or purpose of the diet. The first phase may include three general objective categories: weight management; special purpose (medical); and special purpose (nutrition). All three objective categories incorporate nutritional elements. However, the weight management and physical enhancement categories may integrate nutrition as an important supplemental factor while focusing on eating habits (i.e. where, when, amount, how frequently, and the like), type of food (i.e. caloric content, fat contents, carbohydrates, and the like), and the subscriber's activity level. The two medical and special purpose categories are highly focused on the promotion of nutrition as their primary strategy while integrating eating habits and other dietary behaviors as part of their implementation strategies. The special purpose category includes diets that may be selected to optimize growth and development, aesthetic characteristics (i.e. skin tone/appearance, muscular development, hair texture/color and appearance, nail growth and appearance, and the like), vitality (i.e. libido, energy, endurance, and the like), alertness and focus, aging, as well as alleviate or mitigate the adverse effects of certain specific disorders, behaviors, conditions, illnesses, injuries, medications, and medical treatments. Each of the three objective categories may be divided into subcategories and each subcategory objective may be constructed to incorporate regular progress monitoring capabilities which include checks that facilitate regular recalibration of progress expectations and/or modification (tweaking) of various elements of the diet.

The weight management objective category may include weight gain, weight maintenance, and weight loss subcategories. The weight management categories target a certain body weight and fat distribution as the primary objective. The weight management, special diet programs may facilitate gradual behavior and diet modifications which establish dietary and nutritional sensitivities and healthier eating habits that will extend beyond the prescribed schedule of the special diet program itself.

The special purpose (medical) objective includes subcategories that may address the unique nutritional deficiencies and imbalances that are the consequence or cause of an injury, disease, condition, disorder, and abnormality. Also, the effects of certain prescribed medications and medical treatments may be addressed. The special purpose (medical) objective category may focus on curative and therapeutic benefits of nutritional health, rather than weight management. The purpose of this category may be health-optimization and recovery-optimization, while countering or minimizing the adverse effects of certain medical treatments and drug therapies.

The special purpose (nutrition) objective include, among other things, growth and development, aging, physical fitness, psychological stress, and environmental stress mitigation subcategories. These subcategories focus on the body's nutritional needs as it responds to changes and/or stresses. There are three general types of influences on the body that affect the body's nutritional needs: natural/biological influences; environmental/situational influences; and physical conditioning/exertion. Natural/biological influences include those that are caused by biological changes in the body. These can include childhood growth and development, puberty, pregnancy, nursing, menopause, andropause, aging, and the like. Environmental/situational influences may include pollution, sun exposure, exposure to cold, hazardous materials exposure, sleep deprivation, travel/relocation, emotional stress, and the like. Physical conditioning/exertion influences can include physical stress on the body due to intense physical training. These activities may include muscular stress, joint stress, cardiovascular stress, and the like, usually associated with military training, resistance training, aerobic conditioning, yoga, sports, recreating, physical therapy and the like.

The SDDSP may activate and manage the following special diet support processes resident in the: DASM 490; PDHHM 450; TMM 470; and the DLM 510. Each of the special diet support processes contain own unique set of procedures that govern the actions of respective modules. The special diet support processes of DASM 490, PDHHM 450, and TMM 470 are primarily tasked with acquiring, organizing and distributing certain data elements specific to the subscriber's condition (i.e. physical, psychological, physiological, medical, and the like), behaviors, preferences, health history, and predispositions. The special diet support process, of DLM 510, may be responsible for compiling and analyzing the inputs of special diet support processes of other modules (i.e. DASM 490, PDHHM 450, and TMM 470) in order to identify a suitable special diet model and then customize the special diet model based on specific subscriber characteristics, condition, predispositions, preferences and the like.

The special diet support process, of the DASM 490, may include the acquiring and analysis of current and historical information pertaining to the subscriber's usage of prescription drugs, non-prescription drugs, herbs, and vitamin/mineral supplements. Also, the special diet support process may be responsible for identifying and retrieving the subscriber's history of drug allergies, drug interactions, and adverse drug reactions. Once these data elements are retrieved, they are transmitted to the DLM 510 special diet support process to tailor the special diet model.

The special diet support process of the PDHHM 450 may be responsible for acquiring and maintaining subscriber personal information and health histories. The SDDSP prompts the special diet support process, resident in the PDHHM 450, to systematically screen the databases of PDHHM 450 for certain specific subscriber data elements that includes identifying characteristics (i.e. age, gender, race and ethnicity and the like), health condition and behaviors (mental acuity, medial condition, physical characteristic, physiological condition, allergies, tobacco usages, alcohol usages, and the like), geographical location, preferences, predispositions, and the like. These data elements are then transmitted to the DLM 510 for the selection and tailoring of the special diet model.

The PSM 460a special diet support process screens the databases to verify that core physical, psychological, physiological, and behavioral data elements, necessary to select and tailor the special diet model, are present, complete and current. Once incomplete, missing or obsolete data elements are identified, they are listed, and routed to the TMM 470 special diet support process which then initiates the necessary data acquisition steps that may include: identifying the specific missing data requirements; formulating and submitting the data acquisition queries to the PDAU 200; tracking the PDAU's 200 data acquisition process; and compiling the data acquisition responses. The special diet support process, of the TMM 470, may be divided into two categories, quantitative data acquisition and qualitative data acquisition. Qualitative data queries address subjective materials such as the subscriber's mental attitude or disposition, comfort level, pain/discomfort level, hunger, fatigue, attitudes, preferences, and certain mental facilities. Quantitative data queries address objective queries that utilize test equipment, measurement devices, and/or laboratory tests to establish quantifiable results (i.e. blood pressure, heart rate, heart rhythm, respiratory rate, blood hormone levels, blood toxin levels, and the like). To better utilize qualitative data, the queries are structured in such a way as to gauge the responses (here after referred to as gauged qualitative data). For example, whenever a non-quantitative response is pursued, the subscriber will be queried in such a way as to quantify the response by acquiring the level or degree of severity that best describes the condition or situation.

The PDHHM's special diet support process outputs and DASM's special diet support process outputs are sent to the DLM's special diet support process for further analysis. The DLM special diet support process may have two primary functions which include the selection of a special diet process model and the tailoring of the model to fit the individual characteristics of the subscriber. The DLM's special diet support process culminates in the development of a highly personalized special diet program.

The selection of special diet model candidates may initially be focused on identifying those special diet models that achieve specific objectives (i.e. large amounts of weight loss, small amounts of weight loss, diets for health enhancement, diets for management of diabetes, diets for managing the effects of chemotherapy, and so on). This process may then be further refined by selecting special diet models that are known to be particularly effective in achieving the desired objectives in a specific population group that shares the same or similar subscriber characteristics such as age, gender, race, ethnicity, geographical area, occupation, religion, and the like. Now, one primary special diet model may be selected as well as one or more backup or alternative special diet models are selected.

Once a special diet model has been selected, the DLM special diet support process assesses the subscriber's behavioral (i.e. alcohol usage, tobacco usage, sleeping habits, etc.), psychological, physical, and physiological characteristics as well as certain current and previous allergies, medical conditions, use of medication, and medical treatments that could influence the effectiveness of the special diet model. The DLM special diet support process also assesses the subscribers eating habits, current and past dietary/nutritional intake, dietary preferences and aversions, vitamin and mineral supplement intake, non-prescription drug usage, living and working environments, family history, predispositions, and the like. The special diet model, or combination of special diet models, may then be customized to take into consideration the above-mentioned characteristics. Finally, the special diet model may be further customized by incorporating certain seasonal and geographic idiosyncrasy that would augment the model's effectiveness. The special diet information may thereafter forward to the MM 520, of the CDPU 400, where it may be used to tailor the products that will be made available for purchase.

To facilitate implementation and monitoring, the special diet programs may be divided into segments or phases which include the program initiation phase, several intermediate progress assessment phases, and a program termination phase. Each of the intermediate progress assessment phases may correspond to a progress audit performed by the special diet monitoring process. If the audit detects a condition known as "Failure to Complete Objective" (FCO), the special diet monitoring process (SDMP), of the PTADM 480, advises the DLM special diet support process (through the PSM's special diet development and support process). The DLM special diet support process then develops program and schedule contingencies that are immediately implemented into the next phase of the special diet program. The special diet tailoring, monitoring, and the contingency development processes may be fully computerized and requires processing data through multiple decision-gates that lead down different paths culminating in a highly personalized special diet solution that flexes as changes or unanticipated situations occur.

Certain subscriber behavioral, psychological, physiological, and medical conditions are designated "health-sensitive".

Particular attention may be paid to these conditions to ensure that they are effectively screened against the DLM 510 reference materials to identify dietary considerations or precautions that must to be observed. The dietary considerations or precautions are then incorporated into the special diet program as "core dietary elements" which means all other components of the special diet program must be compatible with these dietary elements.

The SDDSP, of PSM 460*a*, initiates the SDMP, of PTADM 480*a*, upon issuance or release of the special diet product, herein referred to as special diet program. The SDMP may be responsible for monitoring the effectiveness of the special diet program in meeting certain prescribed objectives. This process incorporates periodic audits which include critical and non-critical assessments of the subscriber's behavioral, psychological, physical, physiological condition. The critical assessment audit screens data for evidence of a peculiar, abnormality or adverse reactions. If such evidence is observed, the SDMP issues an ALERT and initiates an "intervention" which can consist of immediate cessation of the special diet program (in cases of quantifiable health risk) or, more likely, a prompting of the SDDSP to immediately construct and issue targeted readjustments or modifications of the special diet program The non-critical assessments focus on program effectiveness. Prescribed special diet program objectives are reviewed to determine whether adequate progress being made. In those cases where the subscriber fails to meet an objective, the SDMP issues an ADVISORY and the SDDSP may be prompted to make adjustments or modifications to the special diet program that would further enhance the subscriber's probability of success. The monitoring process may be computerized and includes continuous schedule adjustments and the tweaking or recalibration of special diet program objectives. The SDMP consists of four activities that include: subscriber input surveillance and data acquisition; data analysis; reporting; and intervention.

The subscriber input surveillance and data-acquisition activities may be used to systematically collect subscriber data pertaining to the behavioral, psychological, physical, and physiological affects the special diet program may be having on the subscriber.

Special diet programs may last from several days, months, or years. During this "active period" the subscriber will be expected to periodically interface with the health maintenance system 100 in regard to subjects other than the special diet. These interactions may result in the acquisition of additional behavioral, psychological, physical, physiological, and environmental data that may either influence the effectiveness of the special diet program or reflect the affects a special diet program may be having on the subscriber's condition. The SDMP may automatically monitor such interactions and may be programmed to detect certain particular characteristics and unusual or abnormal conditions. This information may be then recorded and routed to the SDMP data-analysis activity for further assessment.

The data acquisition activity of SDMP of PTADM 480*a* may be programmed to acquire, on a prescheduled basis, subscriber vital signs and certain psychological, physical, physiological, and behavioral characteristics. This data-acquisition process may be divided into two categories that include data-acquisition queries and data-acquisition tests/measurements. Data-acquisition queries are used to request gauged qualitative data that address subjective material such as the subscriber's mental disposition, sensitivity to pain/discomfort, environmental sensitivity, stress level, attitudes, preferences, and the like. The query process may be intelligently systematic, implying that the queries may be designed to first assess the general condition of the subscriber and the overall progress that is being made. Only when evidence of a peculiarity, abnormality or adverse reaction is present or there are indications that a subscriber may be failing to meet prescribed objectives, can the next tier of investigation be pursued. A feature of the SDMP is its ability to quantify the qualitative responses. This means the SDMP gauges the subscriber's responses relative to an authoritative standard or an established reference point and then assigns a quantitative value to the response. The data-acquisition, test and measurement queries are used to acquire quantitative data that address the psychological, physical and physiological condition of the subscriber as well as their responses or reactions to the special diet program. The intrusiveness of the test/measurement activities may be minimized and the procedures are implemented incrementally, meaning the subscriber may be initially subjected to only a minimal number of key test/measurement procedures. Once abnormalities or evidence of adverse reactions are found, the next tier of testing and measurement is pursued.

The data analysis activity involves the systematic assessment of data collected as part of the data acquisition activity. These data includes test and measurement results, query responses, and monitoring/surveillance data. The purpose of the data analysis activity is to determine whether to continue, modify or terminate the current special diet program. The data analysis activity also calculates the probable point-of-failure and the probability-of-success. The data analysis may involve a continuation decision that further includes three options. Each of these options may have unique triggering mechanisms and consequences. The subscriber's psychological, physical, and physiological characteristics are "baselined", by the SDDSP, to the time prior to the commencement of the special diet program, thereby, the subscriber's starting condition (including health history) becomes an integral part of the continuation decision. The baseline, or more specifically the subscriber's starting condition and corresponding ranges of fluctuation in their psychological, physical and physiological characteristics, may be compared against the subscriber's current characteristics in order to detect changes that could suggest adverse reactions to the special diet program and to evaluate the subscriber's progress, based on the prescribed objectives. Based on this comparative assessment of the subscriber's condition and his/her progress, there are three decision options available: continue the program; modify and continue the program; and terminate the program.

The continue-program-decision means the continuation of existing special diet program since no significant adverse reactions to the diet have been detected. In this case, the diet is achieving its prescribed objectives and there is no evidence that a modification to the diet would significantly enhance the diet's effectiveness. Along with the continue-program-decision, a status of the subscriber's progress may be routed through the PTADM 480*a* to the PDAU 200.

The modify-and-continue-program decision means the special diet program may continue once certain alterations are made to the program and/or schedule. These alterations are driven by one or more of the following circumstances: the existing special diet program may be no longer appropriate; the subscriber may be dissatisfied with certain aspects of the current special diet program and requests modifications be made; the subscriber may have made a reasonable effort to follow the special diet regime but has failed to achieve a significant number of the prescribed objectives; and the subscriber may have failed to achieve a sufficient number of the prescribed objectives because they have consistently failed to follow the diet's procedures. In all of these cases, the methodology, strategy, schedule and/or motivational features, used to implement the existing special diet program, will be subject to an assessment and potential modification The decision to terminate the program may include but is not necessarily limited to: a decision on the part of the subscriber to discontinue the special diet program; evidence that the special diet program may be causing serious physical, psychological, or physiological reactions or complications; and medical reasons to discontinue the special diet program.

The data analysis activity assesses the subscriber's historical project success-ratio and their patterns-of-execution (i.e. the level of self-motivation and ability to follow instructions and complete a task). This information, along with the progress measured in executing the current special diet program, may be key inputs used to calculate the subscriber's most probable point-of-failure and their overall probability-of-success. These calculations are provided to the reporting activity for dissemination.

The reporting activity may be responsible for taking the analysis outputs and developing status reports and disposition reports, as well as conveying success probabilities. These reports are routed to the SDDSP of PSM 460*a* for further action. Status and disposition reporting activities determine whether or how the subsequent phases of the special diet program will be implemented. The status and disposition reporting corresponds to the data analysis's continuation decision. And the success probability reporting addresses the most probable point-of-failure and the overall probability of success.

Reporting activity includes: continuation reporting; diet modification and continuation reporting; termination reporting, and point-of-failure and probability-of-success reporting.

Continuation reporting may be made once the data analysis activity has determined that continuation of the existing special diet program may be appropriate. The continuation reporting activity involves the construction of a status report that includes: status of the progress in completing the prescribed objectives; relative progress in comparison to a similar population group participating in a similar special diet program; and the recognition of progress or objective achievement to-date.

Diet modification and continuation reporting may be made once the data analysis activity may have determined that continuation of the existing special diet program may be appropriate, but modification of the configuration of existing special diet program may be necessary. The diet modification and continuation reporting activity results in the construction of a status and observation report that includes: status of progress in completing the current objectives; adverse reactions to the current diet; deficiencies of current diet; subscriber-recommended modifications; recognition of progress or achievement to-date; and relative progress in comparison to a similar population group participating in a similar special diet program.

Termination reporting may be made once the data analysis efforts determine that the special diet program should be terminated. The termination reporting activity results in the construction of a status and observation report that includes: status of progress completing the current objectives; adverse reactions or medical reasons that require diet termination; deficiencies in the current diet that require diet termination; subscriber requests diet termination; and recognition of progress or achievement to-date.

Point-of-failure and probability-of-success reporting may be made once the analysis activity calculates the ongoing most probable point-of-failure and the ongoing probability-of-success. The point-of-failure and probability-of-success reporting activity utilizes these calculations to tailor the recognition of achievement or motivational segment of the report, which may be forwarded on to the subscriber. In cases where history suggests the most probable point-of-failure may be approaching, the reporting activity intensifies requests for feedback and emphasizes encouragement and positive reinforcement. In cases where the ongoing probability-of-success calculation suggests a loss of momentum, stagnation, or regression, the reporting activity again intensifies its request for feedback, emphasizes progress made to-date, and offers encouragement and positive reinforcement. The structure and content of the encouragement and positive reinforcement messages maybe tailored to the subscriber's experience, value system, and character.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is understood that various omissions, substitutions of equivalents are contemplated as circumstance may suggest or render expedient, but is intended to cover the application or implementation without departing from the spirit or scope of the claims of the present invention.

What is claimed is:

1. A health maintenance system, comprising:
a plurality of computerized personal data acquisition units distributed over a geographical area, each personal data acquisition unit having hardware accessories and software that facilitates interface with a subscriber and the entry of patient demographic data including at least gender, age, race, diet, and geographical location, each personal data acquisition unit also having test and measurement equipment including at least one mechanical, electro-mechanical, optical or acoustic sensor configured to come in contact with the body of a patient so as to acquire patient physical data which, in combination with the patient demographic data comprises patient data;
a plurality of computerized central data processing units distributed over a geographical area, each central data processing unit being communicatively coupled to a designated network of the personal data acquisition units, each central data processing unit configured to:
  remotely manage interactions between each subscriber and the corresponding personal data acquisition unit,
  systematically collect cumulative patient data on multiple patients through the personal data acquisition units,
  organize, categorize and analyze the cumulative patient data,
  identify a specific patient condition for any one patient,
  determine and then transmit to the personal data acquisition unit at least one suggested health solution/treatment for the patient condition for the one patient,
  compile data on the one patient in the form of a health history archive,
  monitor the health of the one patient as he/she subsequently interacts with one of the personal data acquisition units to track the progression of the condition and gauge the effectiveness of the health solution/treatment, and transmit to the personal data acquisition unit any change in the suggested health solution/treatment for the patient condition for the one patient based on the step of monitoring, a plurality of data maintenance and archiving units each communicatively coupled to an assigned network of the central data processing units, and each being configured to:

collect cumulative patient data inputted by their assigned network of central data processing units analyze cumulative patient data to identify correlations and patient health patterns and trends, analyze cumulative patient data to assess the effectiveness and efficiency of prescribed solutions/treatments, and develop changes to reference resources based on the analysis of cumulative data, and communicate changes to their assigned central data processing units, a data maintenance and archiving unit-command center communicatively coupled to a network of the data maintenance and archiving units, the data maintenance and archiving unit-command center configured to:

collect cumulative patient data inputted by the network of data maintenance and archiving units, analyze the cumulative patient data to identify correlations, patterns and trends, add, delete and/or modify resource data including suggested health solution/treatment for various patient conditions based on the analysis of cumulative subscriber data received from the network of the data maintenance and archiving units, and monitor the cumulative patient responses and reactions to suggested health solution/treatments across the network of data maintenance and archiving units to ensure only safe, and effective and efficient health solutions/treatments are prescribed.

2. The health maintenance system of claim 1, wherein the personal data acquisition units, the central data processing units, the data maintenance and archiving units, and the data maintenance and archiving unit-command center are communicatively coupled to each other through a communication network comprising at least one of Internet, public switched telephone network, global system for mobile communications network, and general packet radio service network.

3. The health maintenance system of claim 1, wherein each personal data acquisition unit is a stand-alone personal data acquisition unit-health station having software and hardware components for facilitating interaction between the subscriber and the respective central data processing unit, the personal data acquisition unit-health station comprising a control and display module having
a data processing and data distribution unit,
a memory coupled to the data processing and data distribution unit, and
a plurality of user interface features for secure interaction with the subscriber, the user interface features coupled to the data processing and data distribution unit;

a first data security module coupled to the control and display module, the first data security module configured to:
compress and encrypt data transmitted to the central data processing unit, and
decompress and decrypt data transmitted from the central data processing data unit to the personal data acquisition unit-health station;

a first communication module coupled to the first data security module, the first communication module capable of facilitating communication between the personal data acquisition unit-health station and the central data processing data unit;

a test interface module coupled to the control and display module; and wherein the test and measurement equipment is coupled to the test interface module;

wherein the test interface module is capable of acquiring, processing and forwarding physical data to the control and display module.

4. The health maintenance system of claim 3, wherein the user interface features comprise audio communication features for two way audio communication between the subscriber and the health maintenance system;

video communication features for visual communication of images, messages, alerts, instructions, reports, and general information; and data security features for privacy and protection of data in the health maintenance system.

5. The health maintenance system of claim 4, wherein the audio communication features comprise an audio processor coupled to the data processing and data distribution unit;

a voice recognition unit coupled to the audio processor; and a voice synthesizer coupled to the audio processor.

6. The health maintenance system of claim 4, wherein the video communication features comprise a video processor coupled to the data processing and data distribution unit;

a touchscreen display coupled to the video processor; and a digital camera coupled to the video processor.

7. The health maintenance system of claim 4, wherein the data security features comprise a biometric security identification unit coupled to the data processing and data distribution unit, the biometric security identification unit capable of implementing a subscriber identification verification process for accessing the health maintenance system.

8. The health maintenance system of claim 7, wherein the biometric security identification unit comprises at least one of fingerprint scanners, retinal scanners, facial scanners, and voice recognition systems.

9. The health maintenance system of claim 4, wherein the user interface features further comprise a digitized moderator participating in audio and video communication with the subscriber.

10. The health maintenance system of claim 3, wherein the subscriber data is stored on an encrypted partition of the memory.

11. The health maintenance system of claim 3, wherein the control and display module further comprises a data acquisition unit coupled to the data processing and data distribution unit, the data acquisition unit capable of collecting and managing the physical data from the test interface module.

12. The health maintenance system of claim 3, wherein the personal data acquisition unit-health station further comprises a built-in-test function for testing and maintaining the health maintenance system in operating and non-operating conditions.

13. The health maintenance system of claim 3, wherein the first communication module functions as a first level of security for preventing unauthorized access of the personal data acquisition unit-health station through the communication network, and receipt of infected data from the respective central data processing unit or outside sources.

14. The health maintenance system of claim 13, wherein the first data security module functions as a second level of security for preventing unauthorized access of the personal data acquisition unit-health station by the central data processing unit, and receipt of infected data from the respective central data processing unit by the personal data acquisition unit-health station.

15. The health maintenance system of claim 3, wherein the test interface module comprises
a test interface electronics assembly capable of receiving, processing, and transmitting physical data to the control and display module; and
an interface panel assembly coupled to the test interface electronics assembly, the interface panel assembly providing electronic interface and connections between the test and measurement equipment and the test interface electronics assembly.

16. The health maintenance system of claim 15, wherein the interface panel assembly comprises a set of indicator lamps for providing the subscriber the operational status of the test and measurement equipment.

17. The health maintenance system of claim 15, wherein the test interface electronics assembly registers the date, time, and environmental conditions, for each test and measurement that is performed.

18. The health maintenance system of claim 3, wherein the test and measurement equipment is configured to detect and record physical characteristics using at least two of the following:
fat detectors monitoring the body fat ratio and fat distribution and enables establishing quantitative fat values and locations;
strength detectors associated with measurement devices and sensors for measuring resistance and detecting the force exerted by the body's various muscles and muscle group at certain points within a range of motion;
skin analyzers capable of detecting range of crucial skin conditions, skin abnormalities and related symptomatic information that enables in identifying the skin disorders, their probable causes, severity, progression and treatment options;
breath analyzers capable of identifying the presence of certain molecules and minute chemical markers or other traces of a condition, imbalance or malady;
body temperature sensors and scanners capable of detecting and measuring body temperature;
scales capable of measuring the subscriber's weight;
measuring devices capable of measuring the subscriber's height and body dimensions;
blood pressure monitors capable of monitoring blood pressure of the subscriber;
respiratory rate monitors capable of monitoring the respiratory rate;
heart rate monitors capable of monitoring the heart rate;
heart rhythm monitors capable of monitoring and deciphering heart rhythms;
blood oxygen analyzers capable of calculating relative percentage of hemoglobin saturated with oxygen during the arterial pulse;
saliva analyzers capable of detecting the presence of chemicals and biochemical imbalances;
vision analyzers capable of evaluating visual acuity, focus, light sensitivity, refraction, visual field, night vision and color vision acuity;
hearing analyzers capable of conducting pure tone tests, speech tests and middle ear tests;
hair analyzers capable of detecting the presence and concentration of drugs, chemical residues, biochemical imbalances, toxins, heavy metals, and radiation present in the body as well as vitamin and mineral deficiencies;
fingernail analyzers capable of fingernail scanning for detecting and analyzing fingernail chemical compositions and physical characteristics that indicate susceptibility to bone diseases and plurality of other conditions as well as for determining exposure to heavy metals and other poisons; and
blood chemistry analyzers for performing chemical analysis of blood samples.

19. The health maintenance system of claim 1, wherein the personal data acquisition unit is a personal data acquisition unit-appended used in combination with a subscriber's personal computer, the personal data acquisition unit-appended comprising a control module having
a data processing and data distribution unit,
a memory coupled to the data processing and data distribution unit, and
a plurality of user interface features coupled to the data processing and data distribution unit, the user interface features in combination with user interface features of the subscriber's personal computer capable of facilitating interactions with the subscriber;
a personal computer interface module coupled to the control module, the personal computer interface module capable of connecting the personal data acquisition unit-appended to the subscriber's personal computer;
a first data security module coupled to the control module, the first data security module configured to:
compress and encrypt data transmitted to the central data processing unit, and
decompress and decrypt data transmitted from the central data processing unit to the personal data acquisition unit-appended;
a first communication module coupled to the first data security module, the first communication module capable of facilitating communication between the personal data acquisition unit-appended and the central data processing unit; and
a test interface module coupled to the control module, the test interface module capable of acquiring, processing and forwarding physical data to the control module.

20. The health maintenance system of claim 19, wherein the control module further comprises a personal computer interface unit for communication with the personal computer interface module.

21. The health maintenance system of claim 19, wherein the control module further comprises a data acquisition unit coupled to the data processing and data distribution unit, the data acquisition unit capable of collecting the physical data from the test interface module.

22. The health maintenance system of claim 19, wherein the user interface features of the personal data acquisition unit-appended comprise
audio communication features used in combination with user interface features of the subscriber's personal computer capable of facilitating two way audio communication between the subscriber and the health maintenance system;

video communication features used in combination with user interface features of the subscriber's personal computer capable of facilitating visual communication of images, messages, alerts, instructions, reports, and general information; and data security features for maintaining subscriber's privacy and for protecting data in the health maintenance system.

23. The health maintenance system of claim 22, wherein the audio communication features comprise an audio processor coupled to the data processing and data distribution unit;

a voice recognition unit coupled to the audio processor; and a voice synthesizer coupled to the audio processor.

24. The health maintenance system of claim 22, wherein the video communication features comprise a video processor coupled to the data processing and data distribution unit, and a digital camera coupled to the video processor.

25. The health maintenance system of claim 22, wherein the data security features comprise a biometric security identification unit coupled to the data processing and data distribution unit, the biometric security identification unit implementing a subscriber identification verification process for accessing the health maintenance system.

26. The health maintenance system of claim 25, wherein the biometric security identification unit comprises at least one of fingerprint scanners, retinal scanners, facial image scanners, and voice recognition systems.

27. The health maintenance system of claim 19, wherein the personal data acquisition unit-appended further comprises a built-in-test function for testing, fault isolation and maintaining the health maintenance system while in operating and stand-by modes.

28. The health maintenance system of claim 19, wherein the first communication module functions as a first level of security for preventing unauthorized external access of the personal data acquisition unit-appended through the communication network, and receipt of infected data from the central data processing unit or external sources.

29. The health maintenance system of claim 28, wherein the first data security module functions as a second level of security for preventing unauthorized external access of the personal data acquisition unit-appended through the communication network, receipt of infected data from the central data processing unit or external sources, and scanning, encrypting and compressing transmitted data.

30. The health maintenance system of claim 19, wherein the test interface module comprises a test interface electronics assembly capable of receiving, processing, and transmitting physical data to the control module; and an interface panel assembly coupled to the test interface electronics assembly, the interface panel assembly providing electronic interface and connections between the test and measurement equipment and the test interface electronics assembly.

31. The health maintenance system of claim 30, wherein the interface panel assembly comprises a set of indicator lamps for providing the subscriber the operational status of the test and measurement equipment.

32. The health maintenance system of claim 30, wherein the test interface electronics assembly registers the date, time, and environmental conditions for each test and measurement that is performed.

33. The health maintenance system of claim 19, wherein the test and measurement equipment is configured to detect and record physical characteristics using at least two of the following:

fat detectors monitoring the body fat ratio and fat distribution and enables establishing quantitative fat values and locations;

strength detectors associated with measurement devices and sensors for measuring resistance and detecting the force exerted by the body's various muscles and muscle group at certain points within a range of motion;

skin analyzers capable of detecting range of crucial skin conditions, skin abnormalities and related symptomatic information that enables in identifying the skin disorders, their probable causes, severity, progression and treatment options;

breath analyzers capable of identifying certain molecules and minute chemical markers or other traces of a condition or malady;

body temperature sensors and scanners capable of detecting and measuring body temperature;

scales capable of measuring the subscriber's weight;

measuring devices capable of measuring the subscriber's height and body dimensions;

blood pressure monitors capable of monitoring blood pressure of the subscriber;

respiratory rate monitors capable of monitoring the respiratory rate;

heart rate monitors capable of monitoring the heart rate;

heart rhythm monitors capable of monitoring and deciphering heart rhythms;

blood oxygen analyzers capable of calculating relative percentage of hemoglobin saturated with oxygen during the arterial pulse;

saliva analyzers capable of detecting the presence of chemicals and biochemical imbalances;

vision analyzers capable of evaluating visual acuity, focus, refraction, visual field, light sensitivity, night vision and color vision acuity;

hearing analyzers capable of conducting pure tone tests, speech tests and middle ear tests;

hair analyzers capable of detecting the presence and concentration of drugs, chemical residues, toxins, heavy metals, biochemical imbalances and radiation present in the body as well as vitamin and mineral deficiencies;

fingernail analyzers capable of fingernail scanning for detecting and analyzing fingernail chemical compositions and physical characteristics that indicate susceptibility to bone diseases and plurality of other conditions as well as for determining exposure to heavy metals and other poisons; and blood chemistry analyzers for performing chemical analysis of blood samples.

34. The health maintenance system of claim 19, wherein the subscriber's personal computer comprises at least one of desktops, laptops, tablets and personal digital assistants.

35. The health maintenance system of claim 1, wherein the personal data acquisition unit is a subscribers' personal computer installed with a health maintenance system software, the health maintenance system software comprising subscriber identification verification features, data security features, log-on support for accessing the health maintenance system, and communication features working in combination with communication features of the subscriber's personal computer for interacting with the subscriber and for facilitating communication between the subscriber's personal computer and the central data processing unit.

36. The health maintenance system of claim 35, wherein the health maintenance system software is stored on a CD, DVD or similar data storage devices.

37. The health maintenance system of claim 35, wherein the subscriber's personal computer comprises at least one of desktops, laptops, tablets and personal digital assistants.

38. The health maintenance system of claim 1, wherein analyzing the cumulative patient data comprises subjecting the cumulative patient data to an analytical process comprising at least one of comparative analysis, patterns and trends analysis, reference data correlation, relative condition process, risk analysis, and abnormality detection.

39. The health maintenance system of claim 38, wherein comparative analysis comprises comparing the patient's behavioral, psychological, physical and physiological characteristics against those of a similar population group and against authoritative standard data.

40. The health maintenance system of claim 38, wherein information categories for patterns and trends analysis comprises detection and assessment of at least one of psychological characteristic fluctuations; physical characteristic fluctuations, physiological characteristic fluctuations; frequency and severity of illness; frequency and severity of injuries; prescription drug usage type, frequency, and dosage; substance usage fluctuations; and behavior fluctuations for establishing patterns and identifying trends.

41. The health maintenance system of claim 38, wherein sources for reference data correlation comprises at least one of medical journals, studies, medical research papers, health and medicine textbooks, medical treatment research data, health related literature, demographic data, census data, health statistics, fertility/reproductive data, sexual performance enhancement data, health and race data, health and gender data, health and ethnicity data, vitamin and mineral supplement data, medical treatments and therapies data, immunization data, childhood development data, microbial infection research and data, parasitical infections and research data, epidemiology data, nutritional data, dietary data, sleep disorder data, longevity enhancement data, substance abuse data, environmental toxicity data, pharmaceutical data, occupational health data, occupational hazards data, food and drink bacterial contamination data, kinesiology data, detection and treatment of nuclear/biological/chemical exposure data, first aid data, maturation and aging data, cosmetic rejuvenation data, civil defense data, psychology research data, and mental acuity test data.

42. The health maintenance system of claim 38, wherein the relative condition process comprises subjecting patient's behavioral, psychological, physical, and physiological characteristics to a statistical comparative analysis to rank the patient's behavioral, psychological, physical, and physiological characteristics data, relative to those in a similar population group.

43. The health maintenance system of claim 38, wherein the abnormality detection process comprises an activity comprising at least one of
screening of behavioral, psychological, physical and physiological characteristics against authoritative standards and those of a similar population group for detecting abnormalities, screening of behavioral, psychological, physical and physiological patterns for detecting deviations from the patient's normal patterns, screening of monitored data for detecting indications of adverse reactions or peculiarities that would indicate an abnormal condition; and screening of patient interactions with the health maintenance system for detecting abnormal responses.

44. The health maintenance system of claim 1, wherein each central data processing unit also is configured to develop and customize at least one of the health product, program, service and health regime for the subscriber comprising:

a categorization phase involving the screening of patient data for identifying at least one most suitable product, service, program or regime category or combination of categories, based on the patient's identifying characteristics and condition, and a strategy and solution phase involving identification of selectively compiled products, programs services, and regimes that target a particular condition, and further personalizing the strategy for customizing the products, programs, services and regimes to be compatible with the patient's current condition, preferences, predispositions and situations.

45. The health maintenance system of claim 44, wherein the categorization phase includes selecting categories comprising at least one of aging category, in-home care and support category, weight management category, health condition monitoring and assessment category, medical condition assessment and treatment category, childhood development category, behavior assessment and modification category, mental cognition and acuity assessment category, chronic illness assessment and management/treatment category, occupational health assessment and response category, food and beverage contamination affects and treatment category, medical treatment effectiveness monitoring category, pregnancy monitoring and management category, nutritional assessment and nutritional intervention strategy category, nuclear/biological/chemical exposure assessment and response category, environmental toxin exposure assessment and response category, common chemical exposure assessment and chemical affects treatment category, fertility and reproduction assessment and treatment category, sexual performance assessment and enhancement category, aging affects assessment and mitigation category, skin, hair and teeth/gums appearance, assessments and enhancements category, drug affects monitoring and assessment category, endurance assessment and enhancement category and the posture, gait, strength, flexibility, robustness, mobility musculoskeletal assessment and enhancement strategy category.

46. The health maintenance system of claim 1, wherein the central data processing units are also configured to perform prognostics involving the calculation of statistical probability, of a change in a condition, by considering the patient's age, gender, race, ethnicity, geographical location, current health condition(s), health history data, family health history, robustness, historical rates of recovery from illness and injury, known predispositions and behaviors, scientific knowledge, known treatment effectiveness, case studies, condition progression in similar population groups, and medical research.

47. The health maintenance system of claim 1, wherein the central data processing units are also configured to analyze patterns and trends of the cumulative patient health histories, temporarily archive individual health histories, and make copies of health histories available to their respective patient and the patient's designee including emergency medical personnel.

48. The health maintenance system of claim 1, wherein each central data processing unit comprises:
a second communication module configured to:
facilitating communications between the central data processing unit and the personal data acquisition units within the designated network of the central data processing unit, and
facilitating communications between the central data processing unit and a data maintenance and archiving unit that exchanges data with the central data processing unit and monitors the performance and operational availability of the central data processing unit;
a second data security module coupled to the second communication module, the second data security module configured to:
compress and encrypt data transmitted to the personal data acquisition unit and the data maintenance and archiving unit, and
decompress and decrypt data received from the personal data acquisition unit and the data maintenance and archiving unit;
a data control and distribution module coupled to the second data security module, the data control and distribution module capable of registering incoming actions, linking certain subscriber data to the actions, assigning action codes, distributing action assignments to at least one module of the central data processing unit, verifying responses and distributing outgoing responses;
a multimedia presentation preparation module coupled to the data control and distribution module and to the second data security module, the multimedia presentation preparation module compiles and organizes the material in a presentational format including scripting the digitized moderator, choreographing material as well as tailoring graphics, vocabulary and syntax level;
a personal data and health history module coupled to the data control and distribution module, the personal data and health history module capable of acquiring, maintaining, analyzing, and generating at least one report based on the subscriber's personal data and health history;
a personal services module coupled to the data control and distribution module, the personal service module capable of assessing inputs from the subscriber and from other modules, of the central data processing unit, for establishing, among other things, the subscriber's: demographics (i.e. age, gender, race, ethnicity, geographic location, occupation, education, marital status, children, religion, etc.); physical, physiological, and psychological characteristics; behaviors and attitudes; health/medical condition(s); health, medical and dietary patterns and trends; nutrition, lifestyle, and preferences for identifying corresponding needs, and further identifying at least one health product, program, health service and health regime for meeting the subscriber's needs;
a test and measurement module coupled to the data control and distribution module, the test and measurements module capable of specifying and acquiring a plurality of measurements from a partial group comprising physical, visual, physiological, biochemical, chemical, bacterial, viral, fungal, nuclear, electromagnetic spectral, thermal, electrical and biological measurements;
a patterns, trends, and abnormality detection module coupled to the data control and distribution module, the patterns, trends, and abnormality detection module capable of automatically collecting, recording, and analyzing a plurality of inputs provided by the personal data and health history module and the test and measurements module for identifying patterns, trends and abnormalities;
a drug and supplement module coupled to the data control and distribution module, the drug and supplement module capable of acquiring and analyzing the subscriber's prescription drug, non-prescription drug, vitamin supplement, mineral supplement and herbal usage for identifying their complications, interactions, reactions and side effects as well as identifying one or more safe drug, supplement or other remedy that effectively meets the particular needs of the subscriber,
a database library module coupled to the patterns, trends, and abnormality detection module, drug and supplement module, personal service module and personal data and health history module, the database library module comprising a plurality of databases having authoritative standards and reference materials addressing a plurality of health subjects; and
a marketplace module coupled to the data control and distribution module, the test and measurement module, patterns, trend and abnormality detection module, drug and supplement module, personal services module, personal data and health history module and the database library module, the market module offering the subscriber an online store having a plurality of procurable health products tailored to the subscriber's unique demographics including age, gender, race, ethnicity, geographic location, occupation, education, marital status, children, religion, physical characteristics, physiological characteristics, psychological characteristics, medical/health condition(s), and corresponding needs.

49. The health maintenance system of claim 48, wherein the report generated by the personal data and health history module comprises at least one of personal history- health and medical report; family history-health history and medical report; physical characteristics and features report; biological system characteristics report; genetic predispositions report; abnormalities report; infection and disease history report; physiological conditions reports, drug and supplement history report; accident and injury history report; diet, nutrition, and eating habits report; sleeping habits report; allergy history report; medical conditions, procedures and treatments reports; behavior and lifestyle history report; sexual activity and sexual history reports; pregnancy history report; physical activity reports; work history and work environment reports; exposure to toxic nuclear, biological and chemical substances reports; exposure to occupational and environmental hazardous substance reports; home environment safety reports; travel history reports; maturation and aging reports; mental cognition and mental acuity reports; chronic condition monitoring reports; inoculation history reports; and supporting function reports.

50. The health maintenance system of claim 48, wherein the personal service module, in collaboration with the data base library, identifies and enhances the health products, programs, services and health regimes from a partial group comprising at least one of special diet and nutrition programs; physical activity and exercise programs; exercise equipment optimization; health optimization programs; medical condition management programs; assisted living programs; health condition monitoring programs; drug monitoring programs; prescription drug and nonprescription drug selection; medical treatment monitoring programs; vitamin and mineral supplement programs; vitamin supplement selection; mineral supplement selection; chronic condition surveillance programs; disease and injury recovery programs; beauty care and treatment programs; beauty care products; hormone management programs; sexual performance programs; occupational safety programs; fertility management programs; pregnancy management programs, menopausal/andropause symptom mitigation programs; menu preparation and shopping programs; longevity optimization programs; prescription drug reminder programs; medical and Rx dictionary programs; MD appointment reminder programs; first aid instruction and intervention programs; physician and medical facility assessment programs; special health equipment lists; home environment safety assessment programs; human growth and development evaluation programs; nuclear, biological and chemical decontamination and treatment programs; and lifestyle and behavior-health assessment program.

51. The health maintenance system of claim 48, wherein test and measurement module acquires a plurality of measurements from a partial group comprising physical, visual, physiological, biochemical, chemical, bacterial, fungal, viral, nuclear, electromagnetic spectral, thermal, electrical and biological measurements for developing a plurality of assessments, comprising at least one of physical, psychological and physiological assessment; treatment effectiveness assessment; drug and supplement response assessment; environmental toxicity assessment; condition monitoring assessment; growth and development assessment; coordination, physical fitness, strength and flexibility assessment.

52. The health maintenance system of claim 48, wherein the patterns, trends, and abnormality detection module incorporates processes comprising at least one of: mental acuity and cognitive assessment; patterns and trends analysis; comparison analysis, and prognostics.

53. The health maintenance system of claim 52, wherein the mental acuity and cognitive assessment comprises a methodology comprising at least one of response consistency, response time-delay tracking and comparison; reasoning consistency; mental fatigue tracking and historical comparison; and word and graphic association and recognition.

54. The health maintenance system of claim 52, wherein the patterns and trends analysis comprises at least one of behavior, psychological, physical and physiological characteristics pattern and trend analysis; biological cycle pattern and trends; qualitative environmental pattern and trend correlations; adverse reaction monitoring and pattern and trend association.

55. The health maintenance system of claim 52, wherein the comparison analysis comprises at least one of: pattern, trend and health characteristic comparisons to authoritative standards and reference materials for assessing health conditions and detecting abnormalities; pattern, trend and health characteristic comparisons to those of similar population groups for assessing health conditions and detecting abnormalities; comparisons of subscriber's health patterns and trends and health condition to those of similar population groups and authoritative standards in order to establish subscriber's relative condition and rate of maturation or aging; and comparisons of specific condition characteristics and patterns and trends against authoritative standards, reference materials and similar population groups in order to diagnose the condition and establish condition severity, progression and rate of recovery.

56. The health maintenance system of claim 52, wherein the prognostics comprises at least one of: medical condition diagnosis and stage of development; health history assessment and comparison to authoritative standards and those of similar population groups; maturation and aging progression assessment and comparison to authoritative standards and to those of similar population groups; recovery or healing progression assessment and comparison to authoritative standards and to those of similar population groups; physical, psychological and physiological degradation progression assessments and comparisons to authoritative standards and similar population groups; family health history assessments and comparisons to authoritative standards and similar population groups; injury or illness history assessment and comparisons to authoritative standards and those of similar population groups; frequency and severity of injury and illness relative to the norm for a similar population group; physical fitness relative to the norm for a similar population group; emotional condition relative the norm for a similar population group; and medical history assessment and comparison to authoritative standards and similar population groups.

57. The health maintenance system of claim 48, wherein the drug and supplement module interacts with other modules for collecting data comprising at least one of: drug usage reaction, interaction and complication surveillance and assessment; abnormal drug response detection and alerts; vitamin and mineral supplement usage reaction, interaction and complication surveillance and assessment; abnormal vitamin and mineral supplement response detection and alert; health monitoring for detecting drug and/or supplement avoidance conditions; prescription drugs comparisons to generic drugs; subscriber health abnormality correlations to vitamin and/or mineral imbalances; prescription and nonprescription subscriber drug usage history and effectiveness assessments; vitamin and mineral usage history and effectiveness assessments; personalized drug and supplement therapies for hormone imbalances; personalized vitamin and mineral supplements regimes for long term health maintenance and optimized longevity; vitamin and mineral supplement brand comparisons; drug allergy symptom surveillance; pregnancy precautions drug and supplement avoidance and alerts; personalized drug and supplement regimes for safe and effective weight management; personalized drug substitution strategies; personalized drug and supplement strategies for purging toxins and poisons; nutritional assessments to determine vitamin and mineral imbalances in infants and children; drug and supplement treatment strategies for specific exposures to toxic nuclear, biological and chemical substances; drug and supplement treatment strategies for specific exposures to toxic environmental substances; and drug and supplement treatment strategies for occupational exposure to specific toxic or hazardous substances.

58. The health maintenance system of claim 48, wherein the marketplace module provides plurality of health products to be purchased from a partial group including products based on subscriber's demographics including age, gender, race, ethnicity, educational level, religion, geographical location, marital status, children, occupation, health condition, medical condition and treatments, physical fitness, mental acuity, participation in prescribed health programs, behaviors including alcohol and tobacco usage and recreational activities.

59. The health maintenance system of claim 1, wherein the data maintenance and unit archiving unit-command center comprises
a communication module-command center capable of facilitating communication between the data maintenance and archiving unit-command center and the data maintenance and archiving units;

a data security module-command center coupled to the communication module-command center, the data security module-command center configured to:
  compress and encrypt data transmitted to the data maintenance and archiving units, and
  decompress and decrypt data transmitted from the data maintenance and archiving units to the data maintenance and archiving unit-command center;
a data control and distribution module-command center coupled to the data security module-command center, the data control and distribution module-command center capable of registering, dating, prioritizing, distributing, and tracking incoming and outgoing messages;
a master database library coupled to the data control and distribution module-command center, the master database library comprising latest configuration of the health maintenance system's reference materials, and models of health products, programs, services and regimes;
a master health history archive coupled to the data control and distribution module-command center, the master health history archive comprising a permanent, centralized health history database archive of each subscriber and a compilation of personal health histories that are analyzed for identifying population patterns and trends;
a health history archive and analysis team which interacts with the data control and distribution module-command center and the master health history archive, the health history archive and analysis team capable of
  supporting the authentication of requests to retrieve archived data,
  supporting the expediting of data retrieval process,
  compiling cumulative archived health history data for identifying population peculiarities, patterns and trends, and
  assessing the adequacy, effectiveness and performance of the master health history archive;
a reference material research team which interacts with the data control and distribution module-command center and the master database library, the reference material research team capable of
  researching and developing new references new reference material recommendations,
  source data screening for verifying authenticity and credibility of the source data,
  reviewing data maintenance and archiving unit change recommendations,
  reviewing the health history archive and analysis team's reference material change recommendations, and
  assessing the adequacy, effectiveness and performance of the master database library's source data, reference materials, products, programs, services, and regimes; and
a strategic analysis team interacts with the data control and distribution module-command center, the reference material research team, and the health history archive and analysis team, the strategic analysis team capable of collecting, interpreting, analyzing and integrating data with the objective of evaluating the operational status, effectiveness, and performance of the health maintenance system and detecting peculiarities and abnormalities as well as recognizing undeveloped opportunities for further enhancing the health maintenance system.

60. The health maintenance system of claim 59, wherein the health history databases of the master health history archive include a group of subscriber personal identification characteristics comprising at least one of fixed personal identification characteristics such as date of birth, gender, race, ethnicity, sexual preference; flexible personal identification characteristics such as current and past names, addresses, marriages, children, education, occupations including descriptions of work and hazardous materials exposure, and military service; physical characteristics and description; historical health patterns and trends; family heath history; travel history; medical conditions and treatments including prescription and nonprescription drugs; psychological and physiological characteristics and relative condition including test and measurement results; physical fitness; abnormalities, disabilities and deformities; mental cognition and acuity; inoculations; behaviors including drugs, alcohol and tobacco usage.

61. The health maintenance system of claim 59, wherein the health history archive and analysis team is further capable of analyzing the data of master health history archive by using analytical processes selected from the group consisting of patterns and trend analysis of master health history archive, health product performance and effectiveness analysis, and combinations comprising at least two of the foregoing.

62. The health maintenance system of claim 1, wherein each data maintenance and archiving unit comprises:
  a communication module capable of facilitating communication between the data maintenance and archiving unit and the central data processing units within the assigned network of the data maintenance and archiving unit, and between the data maintenance and archiving unit and the data maintenance and archiving unit-command center;
  a data security module coupled to the communication module, the data security module capable of
    compressing and encrypting data transmitted to the data maintenance and archiving units-command center and the central data processing units, and
    decompressing and decrypting data received from the data maintenance and archiving unit-command center and the central data processing units;
  a data control and distribution module coupled to the data security module, the data control and distribution module capable of registering, dating, prioritizing, distributing, and tracking incoming and outgoing messages;
  a database library coupled to the data control and distribution module, the database library comprising the latest configuration of the health maintenance system, reference data, and health products, programs services and regimes;
  a health history archive coupled to the data control and distribution module, the health history archive comprising at least one of fixed personal identification characteristics such as date of birth, gender, race, ethnicity, sexual preference; flexible personal identification characteristics such as current and past names, addresses, marriages, children, education, occupations, and military service; physical characteristics and description; family heath history; travel history; medical conditions and treatments including prescription and nonprescription drugs; psychological and physiological performance and condition including test and measurement results; physical fitness; disabilities and deformities; mental cognition and acuity; inoculations; and behaviors including drugs, alcohol and tobacco usage;
  a reference material and research team that interacts with the data control and distribution module and the database library, the reference material and research team capable of translating, and tailoring database library materials for accommodating the language, social, and culture peculiarities of a geographical territory, and monitoring the performance and capabilities of the database library as well as reviewing the central data processing unit change recommendations; and a health history archive and analysis team that interacts with the data control and distribution module and the health history archive, the health history archive and analysis team capable of acquiring, processing and archiving subscriber health history data received from the central data processing units within the assigned network of the data maintenance and archiving unit.

63. The health maintenance system of claim 1, wherein for implementing a special diet program each central data processing unit comprises a first communication module coupled to the first data security module, the first communication module capable of facilitating communication between the personal data acquisition unit-health station and the central data processing data unit;

a second communication module capable of facilitating communications between the central data processing unit and the personal data acquisition units within the designated network of the central data processing unit, and the central data processing unit and the data maintenance and archiving unit monitoring the performance and operational availability of the central data processing unit;

a second data security module coupled to the first communication module, the second data security module configured to:

compress and encrypt data transmitted to the personal data acquisition unit, and decompress and decrypt data transmitted from the personal data acquisition unit to the central data processing unit;

a data control and distribution module coupled to the second data security module, the data control and distribution module capable of registering incoming actions, linking subscriber data to the actions, assigning action codes, distributing action assignments to at least one module of the central data processing unit, and distributing responses;

a multimedia presentation preparation module coupled to the data control and distribution module and to the second data security module, the multimedia presentation preparation module compiling and organizing the material in a presentational format including scripting the moderator, tailoring graphics, vocabulary and syntax level;

a personal data and health history module coupled to the data control and distribution module, the personal data and health history module capable of acquiring, maintaining, analyzing, and generating at least one report based on the subscriber's personal and health history data;

a personal services module coupled to the data control and distribution module, the personal services module capable of assessing inputs from the subscriber and from other modules of the central data processing unit to establish the subscriber's demographics, physical/physiological/psychological characteristics, behaviors, attitudes, lifestyle, patterns and trends, health/medical condition, preferences, and corresponding needs in order to identify at least one health product for the subscriber, the personal services module having a special diet development and support process configured to:

select a special diet model, and customize the special diet model to produce a special diet program;

a test and measurement module coupled to the data control and distribution module, the test and measurements module capable of specifying and acquiring a plurality of physical and physiological measurements as well as monitoring the progression of the special diet program;

a patterns, trends, and abnormality detection module coupled to the data control and distribution module, the patterns, trends and abnormality detection module capable of automatically collecting, recording, and analyzing a plurality of inputs provided by the personal data and health history module and the test and measurement module, the patterns, trends, and abnormality detection module having a special diet monitoring process capable of calculating the effectiveness of the special diet program;

a drug and supplement module coupled to the data control and distribution module, the drug and supplement module configured to:

acquire and analyze the subscriber's prescription drug, non-prescription drug, vitamin supplement, and mineral supplement usage, and identify at least one drug and supplement product that is best suited for the subscriber;

a database library module coupled to the patterns, trends, and abnormality detection module, drug and supplement module, personal services module and personal data and health history module, the database library module comprising a plurality of databases having reference materials addressing a plurality of health subjects; and a marketplace module coupled to the data control and distribution module, the marketplace module offering to the subscriber an online store having a plurality of personalized health products to be purchased.

64. The health maintenance system of claim 1, wherein the personal data acquisition unit is a stand-alone personal data acquisition unit-health station having a package of software and hardware components for facilitating interaction between the subscriber and the respective central data processing unit, the personal data acquisition unit health station comprising a control and display module having a data processing and data distribution unit, a hard drive memory coupled to the data processing and data distribution unit, and a plurality of user interface features for interaction with the subscriber, the user interface features coupled to the data processing and data distribution unit;

a first data security module coupled to the control and display module, the first data security module configured to:

compress and encrypt data transmitted to the central data processing unit, and decompress and decrypt data transmitted from the central data processing unit to the personal data acquisition unit-health station;

a first communication module coupled to the first data security module, the first communication module capable of facilitating communication between the personal data acquisition unit-health station and the central data processing unit;

a test interface module coupled to the control and display module; and wherein the test and measurement equipment is coupled to the test interface module;

wherein the test interface module is capable of acquiring, processing and forwarding physical data to the control and display module.

65. The health maintenance system of claim 1, wherein the personal data acquisition unit is a personal data acquisition unit-appended (PDAU-A) used in combination with a subscriber's personal computer, the PDAU-A comprising a control module having
a data processing and data distribution unit,
a hard drive memory coupled to the data processing and data distribution unit, and
a plurality of user interface features coupled to the data processing and data distribution unit, the user interface features in combination with user interface features of the subscriber's personal computer for interacting with the subscriber;
a personal computer interface module coupled to the control module, the personal computer interface module capable of connecting the personal data acquisition unit-appended to the subscriber's personal computer;
a first data security module coupled to the control module, the first data security module configured to:
compress and encrypt data transmitted to the central data processing unit, and
decompress and decrypt data transmitted from the central data processing unit to the personal data acquisition unit-appended;
a first communication module coupled to the first data security module, the first communication module capable of facilitating communication between the personal data acquisition unit-appended and the central data processing unit; and
a test interface module coupled to the control module and the test and measurement equipment, the test interface module configured to acquire, process and forward physical data to the control module.

66. The health maintenance system of claim 1, wherein the personal data acquisition unit is a subscribers' personal computer installed with a health maintenance software, the health maintenance software comprising subscriber identification verification features,
data security features,
log-on support for the health maintenance system, and
communication features in combination with communication features of the subscriber's personal computer for interacting with the subscriber and for facilitating communicating between the subscriber's personal computer and the central data processing unit.

67. The health maintenance system of claim 1, wherein the personal data acquisition units, the central data processing units, the data maintenance and archiving units, and the data maintenance and archiving unit-command center are communicatively coupled to each other through a communication network comprising at least one of Internet, public switched telephone network, global system for mobile communications network, and general packet radio service network.

68. The health maintenance system of claim 1,
wherein the data maintenance and archiving units are further configured to monitor performance, effectiveness and reliability of the central data processing units.

69. The health maintenance system of claim 1, wherein the subscriber is the patient.

70. A health maintenance system, comprising:
a plurality of computerized stand-alone personal data acquisition unit-health stations (PDAU-HS) distributed over a geographical area, each PDAU-HS having hardware accessories and software that facilitates interface with a subscriber and the entry of patient demographic data including at least gender, age, race, diet, and geographical location, each PDAU-HS also having test and measurement equipment including at least one mechanical, electro-mechanical, optical or acoustic sensor configured to come in contact with the body of a patient so as to acquire patient physical data which, in combination with the patient demographic data comprises patient data;
a plurality of computerized central data processing units distributed over a geographical area, each central data processing unit being communicatively coupled to a designated network of the PDAU-HS and being configured to remotely manage interactions between each subscriber and the corresponding PDAU-HS, wherein each central data processing unit is further configured to:
systematically collect cumulative patient data on multiple patients through the PDAU-HS,
organize, categorize and analyze the cumulative patient data,
identify a specific patient condition for any one patient,
determine and then transmit to the PDAU-HS at least one suggested health solution/treatment for the patient condition for the one patient,
compile data on the one patient in the form of a health history archive,
monitor the health of the one patient as he/she subsequently interacts with one of the PDAU-HS to track the progression of the condition and gauge the effectiveness of the health solution/treatment, and
transmit to the PDAU-HS any change in the suggested health solution/treatment for the patient condition for the one patient based on the step of monitoring,
wherein each PDAU-HS further includes:
a control and display module having:
a data processing and data distribution unit,
a memory coupled to the data processing and data distribution unit, and
a plurality of user interface features for secure interaction with the subscriber, the user interface features coupled to the data processing and data distribution unit;
a first data security module coupled to the control and display module, the first data security module configured to:
compress and encrypt data transmitted to the respective central data processing unit, and
decompress and decrypt data transmitted from the respective central data processing data unit to the PDAU-HS;
a first communication module coupled to the first data security module, the first communication module configured to facilitate communication between the PDAU-HS and the respective central data processing data unit;
a test interface module coupled to the control and display module, and
wherein the test and measurement equipment is coupled to the test interface module, and
wherein the test interface module is configured to acquire, process and forward patient data to the control and display module,
a plurality of data maintenance and archiving units each communicatively coupled to a network of the central data processing units and being configured to:

monitor performance, effectiveness and reliability of the central data processing units, collect cumulative patient data inputted by the network of central data processing units, analyze cumulative patient data to identify correlations and patient health patterns and trends, analyze cumulative patient data to assess the effectiveness and efficiency of prescribed solutions/treatments, and develop changes to reference resources based on the analysis of cumulative data, and communicate changes to the central data processing units, a data maintenance and archiving unit-command center communicatively coupled to a network of the data maintenance and archiving units, the data maintenance and archiving unit-command center configured to:

collect cumulative patient data inputted by the network of data maintenance and archiving units, analyze the cumulative patient data to identify correlations, patterns and trends, add, delete and/or modify resource data including suggested health solution/treatment for various patient conditions based on the analysis of cumulative subscriber data received from the network of the data maintenance and archiving units, and monitor the cumulative patient responses and reactions to suggested health solution/treatments across the network of data maintenance and archiving units to ensure only safe, and effective and efficient health solutions/treatments are prescribed.

71. The health maintenance system of claim 70, wherein the subscriber is the patient.

72. A health maintenance system, comprising:

a plurality of computerized personal data acquisition units distributed over a geographical area, each personal data acquisition unit having hardware accessories and software that facilitates interface with a subscriber and the entry of patient demographic data including at least geographical location, personal identification data, physical characteristics data, health profile data, physiological characteristics data, drug and supplement data, prescription and non-prescription drug history data, diet and nutritional data, personal health baseline data, and behavior data, each personal data acquisition unit also having test and measurement equipment including at least one mechanical, electro-mechanical, optical or acoustic sensor configured to come in contact with the body of a patient so as to acquire patient physical data which, in combination with the patient demographic data comprises patient data;

a plurality of computerized central data processing units distributed over a geographical area, each central data processing unit being communicatively coupled to a designated network of the personal data acquisition units and being configured to:

remotely manage interactions between each subscriber and the corresponding personal data acquisition unit, identify a specific patient condition for any one patient, determine and then transmit to the personal data acquisition unit at least one suggested health solution/treatment for the patient condition for the one patient, compile data on the one patient in the form of a health history archive, monitor the health of the one patient as he/she subsequently interacts with one of the personal data acquisition units to track the progression of the condition and gauge the effectiveness of the health solution/treatment, transmit to the personal data acquisition unit any change in the suggested health solution/treatment for the patient condition for the one patient based on the step of monitoring, systematically collect cumulative patient data on multiple patients through the personal data acquisition units, and organize, categorize and analyze the cumulative patient data, wherein determining and then transmitting to the personal data acquisition unit at least one suggested health solution/treatment for the patient condition for the one patient includes referencing the organized, categorized and analyzed cumulative patient data, a data maintenance and archiving unit communicatively coupled to a network of the central data processing units and being configured to:

monitor performance, effectiveness and reliability of the central data processing units, collect cumulative patient data inputted by the network of central data processing units, analyze cumulative patient data to identify correlations and patient health patterns and trends, analyze cumulative patient data to assess the effectiveness and efficiency of prescribed solutions/treatments, and develop changes to reference resources based on the analysis of cumulative data, and communicate changes to the central data processing units, a data maintenance and archiving unit-command center communicatively coupled to a network of the data maintenance and archiving units, the data maintenance and archiving unit-command center configured to:

collect cumulative patient data inputted by the network of data maintenance and archiving units, analyze the cumulative patient data to identify correlations, patterns and trends, add, delete and/or modify resource data including suggested health solution/treatment for various patient conditions based on the analysis of cumulative subscriber data received from the network of the data maintenance and archiving units, and monitor the cumulative patient responses and reactions to suggested health solution/treatments across the network of data maintenance and archiving units to ensure only safe, and effective and efficient health solutions/treatments are prescribed.

73. The health maintenance system of claim 72, wherein the personal identification data comprises at least two of name, address, residence history, age, gender, race, ethnicity, education, sexual preference, marital status, living arrangements, marital history, children, occupation, work history, home and work environments, travel history, military service history, genealogy, relationships, behaviors and recreational activities.

74. The health maintenance system of claim 72, wherein the physical characteristics data comprises at least two of height, weight, body fat ratio, body symmetry and dimensions, skin shade, skin texture, eye color, hair growth, hair color, hair texture, strength symmetry, endurance, coordination, posture, gait, nail growth, nail features, hand and finger shape, feet and toe shape and size, physical peculiarities, physical deformities, growths, blemishes, teeth and gum condition, posture and flexibility.

75. The health maintenance system of claim 72, wherein the health profile data comprises at least two of hazardous and toxic material exposure data, psychological and physiological characteristics, physical performance, abnormalities, health history data, allergies data, medical history and treatment data, stress level data, disabilities, reproductive history, robustness, current health conditions data, activity level and mobility data, history of illnesses data, history of injuries data, rate of recovery mental acuity and cognition data, chronic conditions data, and family health history data.

76. The health maintenance system of claim 72, wherein the physiological characteristics data depicts the quantitative measurements of performance, functionality and condition of organ systems of the body comprising at least one of cardiovascular system, respiratory system, nervous system, skin system, musculoskeletal system, blood system, digestive system, endocrine system, urinary system, reproductive system as well as combinations comprising at least two of the foregoing.

77. The health maintenance system of claim 72, wherein the drug and supplement data comprises at least two of current and past usage of prescription and non-prescription drugs, vitamin supplements, herbs, mineral supplements, treatments, enemas, remedies, topical lotions, ointments, dies, tints, skin peels, and cosmetics usages.

78. The health maintenance system of claim 72, wherein the diet and nutritional data includes systematically recording the subscriber's dietary and nutritional intake including food descriptions and methods of preparation, drink descriptions, quantity ingested, food and drink preferences, frequency ingested, and eating practices and patterns over time.

\* \* \* \* \*